United States Patent
Han et al.

(10) Patent No.: US 6,506,889 B1
(45) Date of Patent: Jan. 14, 2003

(54) RAS SUPPRESSOR SUR-8 AND RELATED COMPOSITIONS AND METHODS

(75) Inventors: Min Han, Boulder, CO (US); Derek Sieburth, Boulder, CO (US)

(73) Assignee: University Technology Corporation

(*) Notice: Subject to any disclaimer, the term of this patent is extended or adjusted under 35 U.S.C. 154(b) by 0 days.

(21) Appl. No.: 09/081,149

(22) Filed: May 19, 1998

(51) Int. Cl.[7] .............................................. C07H 21/02
(52) U.S. Cl. .................... 536/23.1; 536/23.1; 536/24.1; 536/24.3; 536/23.5; 435/320.1; 435/325; 435/69.1; 435/7.1; 435/183; 435/6; 435/221; 530/350; 530/300; 514/9; 514/44; 436/63
(58) Field of Search ............................. 536/23.1, 24.1, 536/24.3, 23.5; 435/6, 320.1, 325, 69.1, 7.1, 183, 221; 530/300, 350; 436/63; 514/44, 9

(56) References Cited

U.S. PATENT DOCUMENTS

| | | | |
|---|---|---|---|
| 4,650,764 A | 3/1987 | Temin et al. | 435/240 |
| 4,683,195 A | 7/1987 | Mullis et al. | 435/6 |
| 4,683,202 A | 7/1987 | Mullis | 435/91 |
| 4,797,368 A | 1/1989 | Carter et al. | 435/320 |
| 4,861,719 A | 8/1989 | Miller | 435/236 |
| 4,873,191 A | 10/1989 | Wagner et al. | 435/172.3 |
| 4,946,778 A | 8/1990 | Ladner et al. | 435/69.6 |
| 4,965,188 A | 10/1990 | Mullis et al. | 435/6 |
| 4,980,289 A | 12/1990 | Temin et al. | 435/235 |
| 5,068,175 A | 11/1991 | Prashad | 435/6 |
| 5,124,263 A | 6/1992 | Temin et al. | 435/240.2 |
| 5,139,941 A | 8/1992 | Muzyczka et al. | 435/172.3 |
| 5,399,346 A | 3/1995 | Anderson et al. | 424/93.21 |
| 5,443,956 A | 8/1995 | Carney | 435/7.23 |
| 5,459,127 A | 10/1995 | Felgner et al. | 514/7 |
| 5,580,859 A | 12/1996 | Felgner et al. | 514/44 |
| 5,582,995 A | 12/1996 | Avruch et al. | 435/71 |
| 5,589,466 A | 12/1996 | Felgner et al. | 514/44 |
| 5,591,582 A | 1/1997 | Bos et al. | 435/6 |
| 5,645,988 A | 7/1997 | Van de Woude et al. | 435/6 |
| 5,721,104 A | 2/1998 | Chen et al. | 435/7.1 |
| 5,739,027 A | 4/1998 | Kamb | 435/240.2 |
| 6,171,815 B1 * | 1/2001 | Au-Young et al. | |

FOREIGN PATENT DOCUMENTS

| | | |
|---|---|---|
| EP | 178 220 | 1/1992 |
| EP | 185 573 | 5/1992 |
| EP | 488 528 | 11/1995 |
| EP | 453 242 | 8/1996 |
| WO | WO 84/03564 | 9/1984 |
| WO | WO 89/07150 | 8/1989 |
| WO | WO 90/02806 | 3/1990 |
| WO | WO 90/08832 | 8/1990 |
| WO | WO 91/16457 | * 10/1991 |
| WO | WO 91/18088 | 11/1991 |
| WO | WO 92/05263 | 4/1992 |
| WO | WO 93/03367 | 2/1993 |
| WO | WO 93/09239 | 5/1993 |
| WO | WO 94/12649 | 6/1994 |
| WO | WO 94/21807 | 9/1994 |
| WO | WO 94/26914 | 11/1994 |
| WO | WO 94/28152 | 12/1994 |
| WO | WO 94/28938 | 12/1994 |
| WO | WO 95/02697 | 1/1995 |
| WO | WO 95/07358 | 3/1995 |
| WO | WO 95/18863 | 7/1995 |
| WO | WO 95/21931 | 8/1995 |
| WO | WO 96/15244 | 5/1996 |
| WO | WO 96/17823 | 6/1996 |
| WO | WO 96/22378 | 7/1996 |
| WO | WO 96/25508 | 8/1996 |
| WO | WO 97/19194 | 5/1997 |
| WO | WO 97/21820 | 6/1997 |

OTHER PUBLICATIONS

Wilson et al., Nature, vol. 368, pp. 32–38, Mar. 3, 1994.*
Waterston et al., Nature Genetics, vol. 1, pp. 114–123, May 1992.*
Selfors et al., PNAS, vol. 95, pp. 6903–6908, Jun. 1998.*
Sternberg et al., Cell, vol. 95, pp. 447–450, Nov. 1998.*
The *C. elegans* Sequencing Constorium, Science, vol. 282, pp. 2012–2017, Dec. 1998.*
Sieburth et al., Cell, vol. 94, pp. 119–130, Jul. 1998.*
Alignments.*
Alignments: Wigler et al., WO/91/16457, Oct. 31, 1991.*
Waterston et al. (Nature Genetics, vol. 1, pp. 114–123, May 1992.*
Wilson et al. (Nature, vol. 368, pp. 32–38, Mar. 3, 1994.*
Patent Publication RD 37105 A.
Anderson and Young, Quantitative Filter Hybridization, in *Nucleic Acid Hybridization* [1995].
Beard et al., "Transcription Mapping of Mouse Adenovirus Type 1 Early Region 3," *Virol.* 175:81–90 [1990].
Beitel et al., "The *Caenorhabditis elegans* gene lin–1 encodes an ETS–domain protein and defines a branch of the vulval induction pathway," *Genes Dev.* 9:3149–3162 [1995].
Bender et al., "Evidence that the Packaging Signal of Moloney Murine Leukemia Virus Extends into the gag Region," *J. Virol.* 61:1639–1646 [1987].
Bernstein et al., "Gene Transfer with Retrovirus Vectors," *Genet. Eng.* 7:235–261 [1985].
Bradley et al., "Formation of Germ–Line Chimaeras From Embryo–Derived Teratocarcinoma Cell Lines," *Nature* 309:255–258 [1984].
Brinster et al., "Factors Affecting the Efficiency of Introducing Foreign DNA into Mice by Microinjecting Eggs," *Proc. Natl. Acad. Sci. USA* 82:4438–4442 [1985].

(List continued on next page.)

Primary Examiner—Karen Cochrane Carlson
Assistant Examiner—Hope A. Robinson

(57) ABSTRACT

The present invention relates to Ras suppressors, in particular the Ras suppressor SUR-8. The present invention provides isolated nucleotide sequence encoding SUR-8, isolated SUR-8 peptides, antibodies that specifically bind SUR-8, methods for the detection of SUR-8, methods for producing SUR-8 transgenic animals, non-human animals expressing SUR-8, and methods for screening compounds for the ability to alter SUR-8 associated signal transduction.

12 Claims, 26 Drawing Sheets

OTHER PUBLICATIONS

Chamberlin and Sternberg, "The lin–3/let–23 pathway mediates inductive signalling during male spicule development in *Caenorhabditis elegans*," Development 120:2713–2721 [1994].

Chamberlin et al., "New RNA Polymerase from *Escherichia coli* Infected with Bacteriophage T7," Nature 228:227–231 [1970].

Church et al., "Three genes of the MAP kinase cascade, mek–2, mpk–1/sur–1 and let–60 ras, are required for meiotic cell cycle progression in *Caenorhabditis elegans*," *Development* 121:2525–2535 [1995].

Clark et al., "The *Caenorhabditis elegans* Locus lin–15, a Negative Regulator of a Tyrosine Kinase Signaling Pathway, Encodes Two Different Proteins," Genetics 137:987–997 [1994].

Cole et al., in *Monoclonal Antibodies and Cancer Therapy*, "The EBV–Hybridoma Technique and its Application to Human Lung Cancer," Alan R. Liss, Inc., pp. 77–96 [1985].

Cote et al., "Generation of Human Monoclonal Antibodies Reactive with Cellular Antigens," Proc. Natl. Acad. Sci. U.S.A. 80:2026–2030 [1983].

Curiel et al., "High–Efficiency Gene Transfer Mediated by Adenovirus Coupled to DNA–Polylysine Complexes," Hum. Gene Ther. 3:147–154 [1992].

Dickson et al., "Raf functions downstream of Ras1 in the Sevenless signal transduction pathway," Nature 360:600–603 [1992].

Erlich (ed.), *PCR Technology*, Stockton Press [1989].

Evans et al., "Establishment in Culture of Pluripotential Cells from Mouse Embyros," Nature 292:154–156 [1981].

Felgner and Ringold, "Cationic Liposome–Mediated Transfection," Science 337:387–388 [1989].

Felgner et. al., "Lipofection: A Highly Efficient, Lipid–Mediated DNA–Transfection Procedure," Proc. Natl. Acad. Sci. U.S.A. 84:7413–7417 [1987].

Ferguson et al., "A genetic pathway for the specification of the vulval cell lineages of *Caenorhabditis elegans*," Nature 326:259–267 [1987].

Field et al., "Mutations of the Adenylyl Cyclase Gene That Block RAS Function in *Saccharomyces cerevisiae*," Science 247:464–467 [1990].

Gossler et al., "Transgenesis by Means of Blastocyst–Derived Embryonic Stem Cell Lines," Proc. Acad. Sci. USA 83:9065–9069 [1986].

Graham and van der Eb, "A New Technique for the Assay of Infectivity of Human Adenovirus 5 DNA," Virol. 52:456–467 [1973].

Graham, "Covalently closed circles of human adenovirus DNA are infectious," EMBO J., 3:2917–2922 [1984].

Graham et al., "Characteristics of a Human Cell Line Transformed by DNA from Human Adenovirus Type 5," J. Gen. Virol. 36:59 [1977].

Gutch et al., "The *Caenorhabditis elegans* SH2 domain–containing protein tyrosine phosphatase PTP–2 participates in signal transduction during oogenesis and vulval development," Genes Dev. 12:571–585 [1998].

Han and Sternberg, "Analysis of dominant–negative mutations of the *Caenorhabditis elegans* let–60 ras gene," Genes Develop. 5:2188–2198 [1991].

Han et al., "*C. elegans* lin–45 raf gene participates in let–60 ras–stimulated vulval differentiation," Nature 363:133–140 [1993].

Harlow and Lane, *Antibodies: A Laboratory Manual*, Cold Spring Harbor Laboratory Press, Cold Spring Harbor, NY.

Haskell and Bowen, "Efficient Production of Transgenic Cattle by Retroviral Infection of Early Embryos," Mol. Reprod. Dev. 40:386–390 [1995].

Hogan et al., in *Manipulating the Mouse Embryo*, Cold Spring Harbor Laboratory Press, Cold Spring Harbor, N.Y. [1986].

Huang et al., "The lin–15 Locus Encodes Two Negative Regulators of *Caenorhabditis elegans* Vulval Development," Mol. Biol. Cell 5:395–412 [1994].

Huse et al., "Generation of a Large Combinatorial Library of the Immunoglobulin Repertoire in Phage Lambda," Science 246:1275–1281 [1989].

Jaenisch, "Transgenic Animals," Science 240:1468–1474 [1988].

Jaenisch, "Germ Line Integration and Mendelian Transmission of the Exogenous Moloney Leukemia Virus," Proc. Natl. Acad. Sci. USA 73:1260–1264 [1976].

Jahner et al., "De novo methylation and expression of retroviral genomes during mouse embryogenesis," Nature 298:623–628 [1982].

Jahner et al., "Insertion of the Bacterial gpt Gene Into the Germ Line of Mice by Retroviral Infection," Proc. Natl. Acad. Sci. USA 82:6927–6931 [1985].

Kacian et al., "A Replicating RNA Molecule Suitable for a Detailed Analysis of Extracellular Evolution and Replication," Proc. Natl. Acad. Sci. USA 69:3038–3042 [1972].

Kaplitt et al., "Expression of a Functional Foreign Gene in Adult Mammalian Brain Following in Vivo Transfer via a Herpes Simplex Virus Type 1 Defective Viral Vector," Mol. Cell. Neurosci. 2:320–330 [1991].

Katz and McCormick, "Signal transduction from multiple Ras effectors," Curr. Opin. Genet. Dev. 7:75–79 [1997].

Kimble, "Alterations in Cell Lineage following Laser Ablation of Cells in the Somatic Gonad of *Caenorhabditis elegans*," Dev. Biol. 87:286–300 [1981].

Kobe et al., "The leucine–rich repeat: a versatile binding motif," Trends Biochem. Sci. 19:415–421 [1994].

Köhler and Milstein, "Continuous Cultures of Fused Cells Secreting Antibody of Predefined Specificity," Nature 256:495–497 [1975].

Kornfeld et al., "The ksr–1 Gene Encodes a Novel Protein Kinase Involved in Ras–Mediated Signaling in *C. elegans*," Cell 83:903–913 [1995].

Kornfeld et al., "The *Caenorhabditis elegans* gene mek–2 is required for vulval induction and encodes a protein similar to the protein kinase MEK," Genes Dev. 9:756–768 [1995].

Kornfeld, "Vulval development in *Caenorhabditis elegans*," Trends Genet. 13:55–61 [1997].

Kozbor et al., "The Production of Monoclonal Antibodies from Human Lumphocytes," Immunol. Today 4:72–79 [1983].

Kuo et al., "Efficient Gene Transfer Into Primary Murine Lymphocytes Obviating the Need for Drug Selection," Blood 82:845–852 [1993].

La Salle et al., "An Adenovirus Vector for Gene Transfer into Neurons and Glia in the Brain," Science 259:988–990 [1993].

Lebkowski et al., "Adeno–Associated Virus: a Vector System for Efficient Introduction and Integration of DNA into a Variety of Mammalian Cell Types," Mol. Cell. Biol. 8:3988–3996 [1988].

Levrero et al., "Defective and nondefective adenovirus vectors for expressing foreign genes in vitro and in vivo," *Gene* 101:195–202 [1991].

Machy, et al., "Gene transfer from targeted liposomes to specific lymphoid cells by electroporation," *Proc. Natl. Acad. Sci. U.S.A.*, 85:8027–8031 [1988].

Mann et al., "Construction of a Retrovirus Packaging Mutant and Its Use to Produce Helper–Free Defective Retrovirus," *Cell* 33:153–159 [1983].

Markowitz et al., "A Safe Packaging Line for Gene Transfer: Separating Viral Genes on Two Different Plasmids," *J. Virol.* 62:1120–1124 [1988].

Marshall, "MAP kinase kinase kinase, MAP kinase kinase and MAP kinase," *Curr. Opin. Genet. Dev.* 4:82–89 [1994].

McCormick, BioTechnol., 3:689 [1985] Reference could not be obtained at this the present time. Applicant will provide copies of the reference upon Examiner's request.

McCormick, "How receptors turn Ras on," *Nature* 363:15–16 [1993].

Mello et al., "Efficient gene transfer in C. elegans: extrachromosomal maintenance and integration of transforming sequences," *EMBO J.* 10:3959–3970 [1991].

Miller and Rosman, "Improved Retroviral Vectors for Gene Transfer and Expression," *BioTechniques* 7:980–990 [1992].

Moodie et al., "Complexes of Ras.GTP with Raf–1 and Mitogen–Activated Protein Kinase Kinase," *Science* 260:1658–1661 [1993].

Robertson et al., "Germ–line Transmission of Genes Introduced into cultured Pluripotential Cells by Retroviral Vector," *Nature* 322:445–448 [1986].

Rodriquez–Viciana et al., "Role of Phosphoinositide 3–OH Kinase in Cell Transformation and Control of the Actin Cytoskeleton by Ras," *Cell* 89:457–467 [1997].

Sambrook et al., *Molecular Cloning: A Laboratory Manual*, Cold Spring Harbor Press, NY, pp. 7.39–7.52, 9.31–9.58 [1989].

Samulski et al., "A Recombinant Plasmid from Which an Infectious Adeno–Associated Virus Genome Can Be Excised in Vitro and Its Use to Study Viral Replication," *J. Virol.* 61:3096–3101 [1987].

Samulski et al., "Helper–Free Stocks of Recombinant Adeno–Associated Viruses: Normal Integration Does Not Require Viral Gene Expression," *J. Virol.* 63:3822–3828 [1989].

Smith and Johnson, "Single–step purification of polypeptides expressed in *Escherichia coli* as fusions with glutathione S–transferase," *Gene* 67:31–40 [1988].

Stewart et al., "Expression of Retroviral Vectors in Transgenic Mice Obtained by Embryo Infection," *EMBO J.* 6:383–388 [1987].

Stratford–Perricaudet et al., "Widespread Long–term Gene Transfer to mouse Skeletal Muscles and Heart," *J. Clin. Invest.* 90:626–630 [1992].

Sundaram and Han, "The C. elegans ksr–1 Gene Encodes a Novel Raf–Related Kinase Involved in Ras–Mediated signal Transduction," *Cell* 83:889–901 [1995].

Sundaram et al., "A Ras–mediated signal transduction pathway is involved in the control of sex myoblast migration in *Caenorhabditis elegans*," *Development* 122:2823–2833 [1996].

Suzuki et al., "Leucine–rich repeats and carboxyl terminus are required for interaction of yeast adenylate cyclase with RAS proteins," *Proc. Natl. Acad. Sci.* 87:8711–8715 [1990].

Therrien et al., "KSR, a Novel Protein Kinase Required for RAS Signal Transduction," *Cell* 83:879–888 [1995].

Ulmer et al., "Heterologous Protection Against Influenza by Injection of DNA Encoding a Viral Protein," *Science* 259:1745–1748 [1993].

White et al., "Multiple Ras Functions Can Contribute to Mammalian Cell Transformation," *Cell* 80:533–541 [1995].

Williams et al., "Introduction of Foreign Genes Into Tissues of Living Mice by DNA–coated Microprojectiles," *Proc. Natl. Acad. Sci. U.S.A.* 88:2726–2730 [1991].

Wilson et al., "Hepatocyte–directed Gene Transfer in Vivo Leads to Transient Improvement of Hypercholesterolemia in Low Density Lipoprotein Receptor–deficient Rabbits," *J. Biol. Chem.* 267:963–967 [1992].

Wu and Han, "Suppression of activated Let–60 Ras protein defines a role of *Caenorhabditis elegans* Sur–1 MAP kinase in vulval differentiation," *Genes Dev.* 8:147–159 [1994].

Wu and Wallace, "The Ligation Amplification Reaction (LAR)–Amplification of Specific DNA Sequences Using Sequential Rounds of Template–Dependent Ligation," *Genomics* 4:560–569 [1989].

Wu and Wu, "Receptor–Mediated in Vitro Gene Transformation by a Soluble DNA Carrier System," *J. Biol. Chem.* 262:4429–4432 [1987].

Wu and Wu, "Receptor–Mediated Gene Delivery and Expression in Vivo," *J. Biol. Chem.* 263:14621–14624 [1988].

Yochem et al., "Ras is Required for a Limited Number of Cell Fates and Not for General Proliferation in *Caenorhabditis elegans*," *Mol. Cell Biol.* 17:2716–2722 [1997].

Clark et al., "C. elegans cell–signalling gene sem–5 encodes a protein with SH2 and SH3 domains," *Nature* 356:340–344 [1992].

Claudianos & Campbell, "The Novel Flightless–I Gene Brings Together Two Gene Families, Actin–Binding Proteins Related to Gelsolin and Leucine–Rich–Repeat Proteins Involved in Ras Signal Transduction," *Mol. Biol. Evol.* 12:405–414 [1995].

Cutler and Morrison, "Mammalian Raf–1 is activated by mutations that restore Raf signaling in Drosophila," *The EMBO Journal* 16:1953–1960 [1997].

Han and Sternberg, "let–60, a Gene That Specifies Cell Fates during C. elegans Vulval Induction, Encodes a ras Protein," *Cell* 63:921–931 [1990].

Hara and Han, "Ras farnesyltransferase inhibitors suppress the phenotype resulting from an activated ras mutation in *Caenorhabditis elegans*," *Proc. Natl. Acad. Sci. USA* 92:3333–3337 [1995].

Hughes et al., "Suppression of Integrin Activation: A Novel Function of a Ras/Raf–initiated MAP Kinase Pathway," *Cell* 88:521–530 [1997].

Lackner et al., "A MAP kinase homolog, mpk–1, is involved in ras–mediated induction of vulval cell fates in *Caenorhabditis elegans*," *Genes & Development* 8:160–173 [1994].

Masuelli and Cutler, "Increased Expression of the Ras Suppressor Rsu–1 Enhances Erk–2 Activation and Inhibits Jun Kinase Activation," *Molecular and Cellular Biology* 16:5466–5476 [1996].

Pawson, "Conviction by genetics," *Nature* 356:285–286 [1992].

Pelech, "Signalling pathways: Kinase connections on the cellular intranet," *Curr. Biol.* 6:551–554 (1996).

Singh and Han, "sur–2, a novel gene, functions late in the let–60 ras–mediated signaling pathway during *Caenorhabditis elegans* vulval induction," *Genes & Development* 9:2251–2265 [1995].

Sundaram and Han, "Control and integration of cell signaling pathways during *C. elegans* vulval development," *BioEssays* 18:473–480 (1996).

Therrien et al., "KSR modulates signal propagation within the MAPK cascade," *Genes & Development* 10:2684–2695 [1996].

Wu et al., "MEK–2, a *Caenorhabditis elegans* MAP kinase kinase, functions in Ras–mediated vulval induction and other developmental events," *Genes & Development* 9:742–755 (1995).

Xing et al., "The protein kinase KSR interacts with 14–3–3 protein and Raf," *Curr. Biol.* 7:294–300 (1997).

Zhang et al., "Kinase Suppressor of Ras Is Ceramide–Activated Protein Kinase," *Cell* 89:63–72 (1997).

Sieburth et al., "SUR–8, a Conserved Ras–Binding Protein with Leucine–Rich Repeats, Positively Regulates Ras–Mediated Signaling in *C. elegans*," *Cell* 94:119–130 (1998).

* cited by examiner-

Consensus:

```
   Hs SUR-8      P . . I G . L . . L . . L . L . . N . L . . L
   Ce SUR-8      P . . I G . L . . L . . L . L . . N . L . . L
   yeast A.C.    P . . α . . L . . L . . L . L . . N . α . . α
```

```
                        1                    10                  20  24
                        |                    |                   |   |
L R R 10    323-346    P E S L L S S L V K L N S L T L A R N C F Q L Y
L R R 11    347-370    P V G G P S Q F S T I Y S L N M E H N R I N K I
L R R 12    371-394    P F G I F S R A K V L S K L N M K D N Q L T S L
```

Consensus:

```
   Hs SUR-8      P . G α . S . . . . L . S L N M . + N . α . . α
   Ce SUR-8      P . G α α . . α . . α . T α N α . . N E L . . α
```

FIGURE 4

FIGURE 8
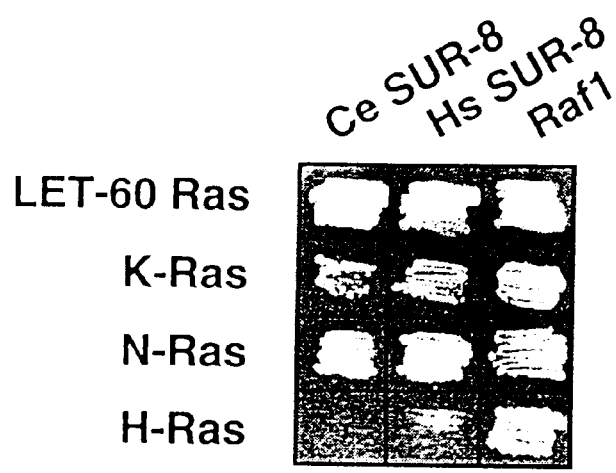
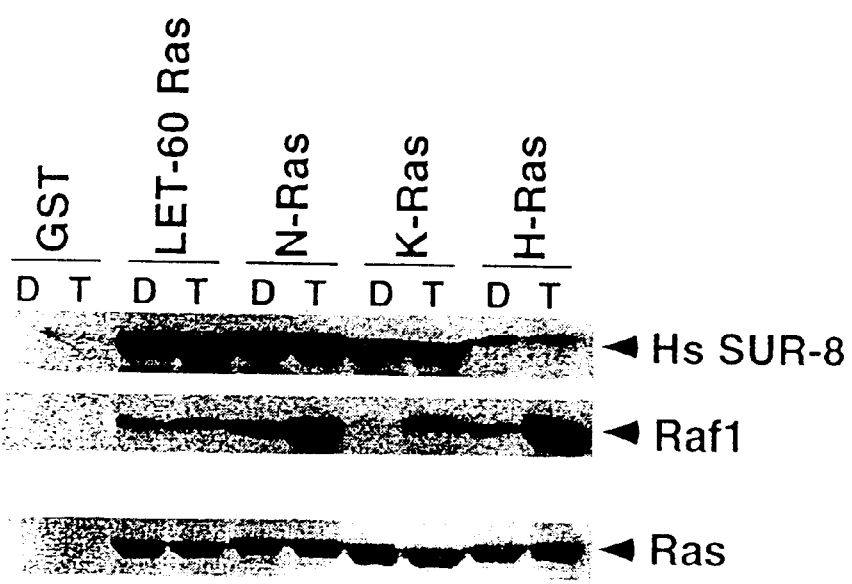

*C. elegans sur-8* cDNA and predicted amino acid sequence

```
     ATGGAGACATCGAAGGAGTTCGAATTCCGTCCGGCCAAGGAGACGTCACGCTCCAAGAGT
   1 ---------+---------+---------+---------+---------+---------+ 60
     TACCTCTGTAGCTTCCTCAAGCTTAAGGCAGGCCGGTTCCTCTGCAGTGCGAGGTTCTCA
```
a    M  E  T  S  K  E  F  E  F  R  P  A  K  E  T  S  R  S  K  S

```
     CCCGGTGGAATCGTCGGAAGACTTTCGAATTTTGCGCGAAACAAGGCGAGGCATTCGTTG
  61 ---------+---------+---------+---------+---------+---------+ 120
     GGGCCACCTTAGCAGCCTTCTGAAAGCTTAAAACGCGCTTTGTTCCGCTCCGTAAGCAAC
```
a    P  G  G  I  V  G  R  L  S  N  F  A  R  N  K  A  R  H  S  L

```
     AGTGAAAAAGGTTCAAATTCGGTTGGTGGAAGTGGTGGAGCAGGTTTTGATAAACCGAGA
 121 ---------+---------+---------+---------+---------+---------+ 180
     TCACTTTTTCCAAGTTTAAGCCAACCACCTTCACCACCTCGTCCAAAACTATTTGGCTCT
```
a    S  E  K  G  S  N  S  V  G  G  S  G  G  A  G  F  D  K  P  R

```
     AAGGACCTCCTAAAAGAATTTCACAAATGCAAAGAGGCGCAGGATCAGAGATTAGATTTG
 181 ---------+---------+---------+---------+---------+---------+ 240
     TTCCTGGAGGATTTTCTTAAAGTGTTTACGTTTCTCCGCGTCCTAGTCTCTAATCTAAAC
```
a    K  D  L  L  K  E  F  H  K  C  K  E  A  Q  D  Q  R  L  D  L

```
     AGCTCAATCGAGATCACGAGCATTCCGTCGCCGATCAAAGAGCTCACACAGCTGACAGAA
 241 ---------+---------+---------+---------+---------+---------+ 300
     TCGAGTTAGCTCTAGTGCTCGTAAGGCAGCGGCTAGTTTCTCGAGTGTGTCGACTGTCTT
```
a    S  S  I  E  I  T  S  I  P  S  P  I  K  E  L  T  Q  L  T  E

```
     TTGTTCTTGTACAAGAACAAGTTGACGTGCTTGCCAACGGAAATAGGTCAACTGGTGAAT
 301 ---------+---------+---------+---------+---------+---------+ 360
     AACAAGAACATGTTCTTGTTCAACTGCACGAACGGTTGCCTTTATCCAGTTGACCACTTA
```
a    L  F  L  Y  K  N  K  L  T  C  L  P  T  E  I  G  Q  L  V  N

```
     CTCAAGAAACTTGGTCTCTCTGAAAATGCGCTTACATCTCTTCCGGATTCACTTGCTTCT
 361 ---------+---------+---------+---------+---------+---------+ 420
     GAGTTCTTTGAACCAGAGAGACTTTTACGCGAATGTAGAGAAGGCCTAAGTGAACGAAGA
```
a    L  K  K  L  G  L  S  E  N  A  L  T  S  L  P  D  S  L  A  S

```
     CTGGAATCACTGGAAACATTGGATTTACGGCACAACAAGTTGACAGAGGTTCCATCGGTC
 421 ---------+---------+---------+---------+---------+---------+ 480
     GACCTTAGTGACCTTTGTAACCTAAATGCCGTGTTGTTCAACTGTCTCCAAGGTAGCCAG
```
a    L  E  S  L  E  T  L  D  L  R  H  N  K  L  T  E  V  P  S  V

```
     ATTTACAAAATCGGGTCGCTCGAAACATTATGGCTGAGGTACAATCGAATTGTGGCAGTT
```

FIG. 9A

```
                 ---------+---------+---------+---------+---------+---------+
         481                                                                    540
                 TAAATGTTTTAGCCCAGCGAGCTTTGTAATACCGACTCCATGTTAGCTTAACACCGTCAA a              I  Y  K  I  G  S  L  E  T  L  W  L  R  Y  N  R  I  V  A  V  -

GACGAACAAATTGGAAATCTGTCAAAATTGAAAATGTTGGATGTTCGTGAGAATAAGATT
         541     ---------+---------+---------+---------+---------+---------+  600
                 CTGCTTGTTTAACCTTTAGACAGTTTTAACTTTTACAACCTACAAGCACTCTTATTCTAA a              D  E  Q  I  G  N  L  S  K  L  K  M  L  D  V  R  E  N  K  I  -

CGAGAGTTACCATCTGCAATTGGAAAACTGACGTCACTGGTTGTGTGTCTTGTCTCTTAT
         601     ---------+---------+---------+---------+---------+---------+  660
                 GCTCTCAATGGTAGACGTTAACCTTTTGACTGCAGTGACCAACACACAGAACAGAGAATA a              R  E  L  P  S  A  I  G  K  L  T  S  L  V  V  C  L  V  S  Y  -

AATCATTTAACACGGGTTCCTGAAGAAATCGGTGACTGCCATTCCCTGACTCAACTCGAT
         661     ---------+---------+---------+---------+---------+---------+  720
                 TTAGTAAATTGTGCCCAAGGACTTCTTTAGCCACTGACGGTAAGGGACTGAGTTGAGCTA a              N  H  L  T  R  V  P  E  E  I  G  D  C  H  S  L  T  Q  L  D  -

CTTCAACACAACGACCTCTCAGAACTACCGTACTCAATAGGAAAACTCGTGAATCTTGTT
         721     ---------+---------+---------+---------+---------+---------+  780
                 GAAGTTGTGTTGCTGGAGAGTCTTGATGGCATGAGTTATCCTTTTGAGCACTTAGAACAA a              L  Q  H  N  D  L  S  E  L  P  Y  S  I  G  K  L  V  N  L  V  -

CGAATCGGAATTCGATACAATAAGATTCGATGTATTCCAAGTGAATTGGAAAGTTGTCAG
         781     ---------+---------+---------+---------+---------+---------+  840
                 GCTTAGCCTTAAGCTATGTTATTCTAAGCTACATAAGGTTCACTTAACCTTTCAACAGTC a              R  I  G  I  R  Y  N  K  I  R  C  I  P  S  E  L  E  S  C  Q  -

CAGCTCGAGGAATTTATTGTAGAGAGCAATCATTTGCAATTACTACCGCCAAACCTGCTC
         841     ---------+---------+---------+---------+---------+---------+  900
                 GTCGAGCTCCTTAAATAACATCTCTCGTTAGTAAACGTTAATGATGGCGGTTTGGACGAG a              Q  L  E  E  F  I  V  E  S  N  H  L  Q  L  L  P  P  N  L  L  -

ACAATGCTTCCAAAAATCCACACAGTGAATCTCTCACGGAACGAGTTGACTGCATTCCCG
         901     ---------+---------+---------+---------+---------+---------+  960
                 TGTTACGAAGGTTTTTAGGTGTGTCACTTAGAGAGTGCCTTGCTCAACTGACGTAAGGGC a              T  M  L  P  K  I  H  T  V  N  L  S  R  N  E  L  T  A  F  P  -

GCAGGCGGACCTCAACAATTTGTGTCCACAGTCACAATTAATATGGAACACAATCAGATT
         961     ---------+---------+---------+---------+---------+---------+  1020
                 CGTCCGCCTGGAGTTGTTAAACACAGGTGTCAGTGTTAATTATACCTTGTGTTAGTCTAA a              A  G  G  P  Q  Q  F  V  S  T  V  T  I  N  M  E  H  N  Q  I  -

TCAAAGATTCCAATCGGAATATTCTCGAAAGCAACACGATTAACAAAACTGAATTTGAAG
```

FIG. 9B

```
       1021 ---------+---------+---------+---------+---------+---------+ 1080
            AGTTTCTAAGGTTAGCCTTATAAGAGCTTTCGTTGTGCTAATTGTTTTGACTTAAACTTC a        S  K  I  P  I  G  I  F  S  K  A  T  R  L  T  K  L  N  L  K   -

GAAAATGAGCTGGTCTCGTTGCCTTTGGACATGGGATCTTGGACATCAATCACCGAGCTC
       1081 ---------+---------+---------+---------+---------+---------+ 1140
            CTTTTACTCGACCAGAGCAACGGAAACCTGTACCCTAGAACCTGTAGTTAGTGGCTCGAG a        E  N  E  L  V  S  L  P  L  D  M  G  S  W  T  S  I  T  E  L   -

AATCTCTCCACAAATCAATTGAAAGTTTTGCCAGAAGATATCGAAAAACTTGTGAATCTG
       1141 ---------+---------+---------+---------+---------+---------+ 1200
            TTAGAGAGGTGTTTAGTTAACTTTCAAAACGGTCTTCTATAGCTTTTTGAACACTTAGAC a        N  L  S  T  N  Q  L  K  V  L  P  E  D  I  E  K  L  V  N  L   -

GAAATCCTTGTGCTGTCCAACAATCAACTGAAAAAGCTTCCAAATCAAATAGGAAATCTC
       1201 ---------+---------+---------+---------+---------+---------+ 1260
            CTTTAGGAACACGACAGGTTGTTAGTTGACTTTTTCGAAGGTTTAGTTTATCCTTTAGAG a        E  I  L  V  L  S  N  N  Q  L  K  K  L  P  N  Q  I  G  N  L   -

AATAAACTCCGCGAGCTGGATCTCGAGGAAAATGAATTGGAGACCGTTCCAACTGAAATC
       1261 ---------+---------+---------+---------+---------+---------+ 1320
            TTATTTGAGGCGCTCGACCTAGAGCTCCTTTTACTTAACCTCTGGCAAGGTTGACTTTAG a        N  K  L  R  E  L  D  L  E  E  N  E  L  E  T  V  P  T  E  I   -

GGATTTTTACAACATCTTACGAAACTGTGGGTTCAGTCAAACAAGATTTTGACTCTACCA
       1321 ---------+---------+---------+---------+---------+---------+ 1380
            CCTAAAAATGTTGTAGAATGCTTTGACACCCAAGTCAGTTTGTTCTAAAACTGAGATGGT a        G  F  L  Q  H  L  T  K  L  W  V  Q  S  N  K  I  L  T  L  P   -

AGATCCATTGGAAATTTGTGTTCGCTTCAAGATTTGCGATTGGGAGAGAACAATTTGACA
       1381 ---------+---------+---------+---------+---------+---------+ 1440
            TCTAGGTAACCTTTAAACACAAGCGAAGTTCTAAACGCTAACCCTCTCTTGTTAAACTGT a        R  S  I  G  N  L  C  S  L  Q  D  L  R  L  G  E  N  N  L  T   -

GCGATTCCCGAGGAAATTGGCCACCTCGACTCATTGAAATCTCTATACCTCAACGACAAC
       1441 ---------+---------+---------+---------+---------+---------+ 1500
            CGCTAAGGGCTCCTTTAACCGGTGGAGCTGAGTAACTTTAGAGATATGGAGTTGCTGTTG a        A  I  P  E  E  I  G  H  L  D  S  L  K  S  L  Y  L  N  D  N   -

TCCTCTCTTCACAATTTGCCATTTGAGTTGGCACTGTGCCAATCGCTTGAAATAATGTCA
       1501 ---------+---------+---------+---------+---------+---------+ 1560
            AGGAGAGAAGTGTTAAACGGTAAACTCAACCGTGACACGGTTAGCGAACTTTATTACAGT a        S  S  L  H  N  L  P  F  E  L  A  L  C  Q  S  L  E  I  M  S   -

ATCGAAAACTCTCCACTTTCTCAGATTCCACCTGAAATCACTGCTGGTGGTCCTTCACTT
```

FIG. 9C

```
1561 ---------+---------+---------+---------+---------+---------+ 1620
     TAGCTTTTGAGAGGTGAAAGAGTCTAAGGTGGACTTTAGTGACGACCACCAGGAAGTGAA
``` a      I  E  N  S  P  L  S  Q  I  P  P  E  I  T  A  G  G  P  S  L  -

```
     GTGATACAATATCTTAAAATGCAAGGTCCCTATCGAGGAGTTGTGATGAATTCTCAATAA
1621 ---------+---------+---------+---------+---------+---------+ 1680
     CACTATGTTATAGAATTTTACGTTCCAGGGATAGCTCCTCAACACTACTTAAGAGTTATT
``` a      V  I  Q  Y  L  K  M  Q  G  P  Y  R  G  V  V  M  N  S  Q  *  -

FIG. 9D human *sur-8* cDNA and predicted amino acid sequence

```
       ATGAGTAGTAGTTTAGGAAAAGAAAAAGACTCTAAAGAAAAAGATCCCAAAGTACCATCA
    1  ------------+----------+----------+----------+----------+----------+  60
       TACTCATCATCAAATCCTTTTCTTTTTCTGAGATTTCTTTTTCTAGGGTTTCATGGTAGT a       M   S   S   S   L   G   K   E   K   D   S   K   E   K   D   P   K   V   P   S   -

GCCAAGGAAAGAGAAAAGGAGGCAAAAGCCTCTGGAGGTTTTGGGAAAGAGAGCAAAGAA
   61  ------------+----------+----------+----------+----------+----------+  120
       CGGTTCCTTTCTCTTTTCCTCCGTTTTCGGAGACCTCCAAAACCCTTTCTCTCGTTTCTT a       A   K   E   R   E   K   E   A   K   A   S   G   G   F   G   K   E   S   K   E   -

AAAGAACCTAAGACCAAAGGGAAAGATGCCAAAGATGGAAAGAAGGACTCCAGTGCTGCC
  121  ------------+----------+----------+----------+----------+----------+  180
       TTTCTTGGATTCTGGTTTCCCTTTCTACGGTTTCTACCTTTCTTCCTGAGGTCACGACGG a.      K   E   P   K   T   K   G   K   D   A   K   D   G   K   K   D   S   S   A   A   -

CAACCAGGGGTGGCATTTTCAGTTGACAATACGATCAAACGGCCAAACCCAGCACCTGGG
  181  ------------+----------+----------+----------+----------+----------+  240
       GTTGGTCCCCACCGTAAAAGTCAACTGTTATGCTAGTTTGCCGGTTTGGGTCGTGGACCC a       Q   P   G   V   A   F   S   V   D   N   T   I   K   R   P   N   P   A   P   G   -

ACTAGAAAAAAATCCAGCAATGCAGAGGTGATTAAAGAGCTCAACAAATGCCGGGAAGAG
  241  ------------+----------+----------+----------+----------+----------+  300
       TGATCTTTTTTTAGGTCGTTACGTCTCCACTAATTTCTCGAGTTGTTTACGGCCCTTCTC a       T   R   K   K   S   S   N   A   E   V   I   K   E   L   N   K   C   R   E   E   -

AATTCAATGCGTTTGGACTTATCCAAGAGATCTATACACATATTGCCATCATCAATCAAA
  301  ------------+----------+----------+----------+----------+----------+  360
       TTAAGTTACGCAAACCTGAATAGGTTCTCTAGATATGTGTATAACGGTAGTAGTTAGTTT a       N   S   M   R   L   D   L   S   K   R   S   I   H   I   L   P   S   S   I   K   -

GAGTTGACTCAATTAACAGAACTTTATTTATACAGTAACAAATTGCAGTCCcTCCCAGCA
  361  ------------+----------+----------+----------+----------+----------+  420
       CTCAACTGAGTTAATTGTCTTGAAATAAATATGTCATTGTTTAACGTCAGGgAGGGTCGT a       E   L   T   Q   L   T   E   L   Y   L   Y   S   N   K   L   Q   S   L   P   A   -

GAGGTGGGATGTTTAGTAAATCTCATGACACTGGCTCTAAGTGAAAATTCACTTACCAGT
  421  ------------+----------+----------+----------+----------+----------+  480
       CTCCACCCTACAAATCATTTAGAGTACTGTGACCGAGATTCACTTTTAAGTGAATGGTCA a       E   V   G   C   L   V   N   L   M   T   L   A   L   S   E   N   S   L   T   S   -

‾TTGCCTGACTCTCTTGATAACTTGAAGAAGCTGCGGATGCTTGATTTACGGCATAATAAA
  481  ------------+----------+----------+----------+----------+----------+  540
       AACGGACTGAGAGAACTATTGAACTTCTTCGACGCCTACGAACTAAATGCCGTATTATTT
```

CTGAGAGAAATTCCTTCAGTGGTGTATAGGCTGGATTCTCTCACCACTCTTTACCTTCGC
   541 ---------+---------+---------+---------+---------+---------+ 600
       GACTCTCTTTAAGGAAGTCACCACATATCCGACCTAAGAGAGTGGTGAGAAATGGAAGCG a      L  R  E  I  P  S  V  V  Y  R  L  D  S  L  T  T  L  Y  L  R   -

TTTAATCGTATAACTACTGTGGAAAAGGACATCAAAAACTTGTCAAAACTCAGCATGCTT
   601 ---------+---------+---------+---------+---------+---------+ 660
       AAATTAGCATATTGATGACACCTTTTCCTGTAGTTTTTGAACAGTTTTGAGTCGTACGAA a      F  N  R  I  T  T  V  E  K  D  I  K  N  L  S  K  L  S  M  L   -

AGCATTCGAGAGAACAAAATTAAACAACTACCTGCTGAAATTGGTGAATTATGTAACCTC
   661 ---------+---------+---------+---------+---------+---------+ 720
       TCGTAAGCTCTCTTGTTTTAATTTGTTGATGGACGACTTTAACCACTTAATACATTGGAG a      S  I  R  E  N  K  I  K  Q  L  P  A  E  I  G  E  L  C  N  L   -

ATTACGCTGGATGTAGCTCACAATCAACTTGAACACCTTCCAAAGGAGATTGGAAACTGT
   721 ---------+---------+---------+---------+---------+---------+ 780
       TAATGCGACCTACATCGAGTGTTAGTTGAACTTGTGGAAGGTTTCCTCTAACCTTTGACA a      I  T  L  D  V  A  H  N  Q  L  E  H  L  P  K  E  I  G  N  C   -

ACACAGATAACCAACCTTGACTTGCAGCACAATGAACTGCTAGACCTCCCAGATACTATA
   781 ---------+---------+---------+---------+---------+---------+ 840
       TGTGTCTATTGGTTGGAACTGAACGTCGTGTTACTTGACGATCTGGAGGGTCTATGATAT a      T  Q  I  T  N  L  D  L  Q  H  N  E  L  L  D  L  P  D  T  I   -

GGAAACCTGTCCAGTTTAAGTCGTCTTGGTCTGAGATATAACAGACTGTCAGCAATACCC
   841 ---------+---------+---------+---------+---------+---------+ 900
       CCTTTGGACAGGTCAAATTCAGCAGAACCAGACTCTATATTGTCTGACAGTCGTTATGGG a      G  N  L  S  S  L  S  R  L  G  L  R  Y  N  R  L  S  A  I  P   -

AGATCATTAGCAAAATGCAGTGCACTTGAAGAATTAAATTTAGAGAACAATAACATTTCT
   901 ---------+---------+---------+---------+---------+---------+ 960
       TCTAGTAATCGTTTTACGTCACGTGAACTTCTTAATTTAAATCTCTTGTTATTGTAAAGA a      R  S  L  A  K  C  S  A  L  E  E  L  N  L  E  N  N  N  I  S   -

ACTTTACCAGAGAGTCTTTTATCAAGTCTTGTGAAACTGAATAGTTTGACCTTAGCTAGA
   961 ---------+---------+---------+---------+---------+---------+ 1020
       TGAAATGGTCTCTCAGAAAATAGTTCAGAACACTTTGACTTATCAAACTGGAATCGATCT a      T  L  P  E  S  L  L  S  S  L  V  K  L  N  S  L  T  L  A  R   -

AATTGCTTCCAGTTGTATCCAGTGGGTGGTCCATCTCAGTTTTCTACCATCTATTCCCTC
  1021 ---------+---------+---------+---------+---------+---------+ 1080
       TTAACGAAGGTCAACATAGGTCACCCACCAGGTAGAGTCAAAAGATGGTAGATAAGGGAG
```

AACATGGAACACAATCGAATCAACAAAATTCCATTTGGAATTTTCTCCAGAGCAAAAGTA
   1081 ---------+---------+---------+---------+---------+---------+ 1140
        TTGTACCTTGTGTTAGCTTAGTTGTTTTAAGGTAAACCTTAAAAGAGGTCTCGTTTTCAT a       N  M  E  H  N  R  I  N  K  I  P  F  G  I  F  S  R  A  K  V   -

TTAAGTAAGCTGAATATGAAGGACAATCAGTTAACATCACTTCCCTTGGATTTTGGAACT
   1141 ---------+---------+---------+---------+---------+---------+ 1200
        AATTCATTCGACTTATACTTCCTGTTAGTCAATTGTAGTGAAGGGAACCTAAAACCTTGA a       L  S  K  L  N  M  K  D  N  Q  L  T  S  L  P  L  D  F  G  T   -

TGGACCAGTATGGTAGAATTGAATTTAGCCACTAATCAGCTCACAAAGATCCCTGAGGAT
   1201 ---------+---------+---------+---------+---------+---------+ 1260
        ACCTGGTCATACCATCTTAACTTAAATCGGTGATTAGTCGAGTGTTTCTAGGGACTCCTA a       W  T  S  M  V  E  L  N  L  A  T  N  Q  L  T  K  I  P  E  D   -

GTGTCTGGTCTCGTTTCTCTTGAGGTTCTTATCTTATCAAACAATCTTCTAAAGAAGCTT
   1261 ---------+---------+---------+---------+---------+---------+ 1320
        CACAGACCAGAGCAAAGAGAACTCCAAGAATAGAATAGTTTGTTAGAAGATTTCTTCGAA a       V  S  G  L  V  S  L  E  V  L  I  L  S  N  N  L  L  K  K  L   -

CCCCATGGTCTTGGAAACCTTAGGAAGTTAAGAGAGTTGGATCTAGAAGAGAACAAATTG
   1321 ---------+---------+---------+---------+---------+---------+ 1380
        GGGGTACCAGAACCTTTGGAATCCTTCAATTCTCTCAACCTAGATCTTCTCTTGTTTAAC a       P  H  G  L  G  N  L  R  K  L  R  E  L  D  L  E  E  N  K  L   -

GAATCCTTGCCAAATGAAATTGCATATCTTAAGGATTTACAGAAATTAGTCTTGACAAAC
   1381 ---------+---------+---------+---------+---------+---------+ 1440
        CTTAGGAACGGTTTACTTTAACGTATAGAATTCCTAAATGTCTTTAATCAGAACTGTTTG a       E  S  L  P  N  E  I  A  Y  L  K  D  L  Q  K  L  V  L  T  N   -

AACCAGTTGACCACTCTTCCCAGAGGCATTGGTCACCTTACTAATCTCACACATCTGGGC
   1441 ---------+---------+---------+---------+---------+---------+ 1500
        TTGGTCAACTGGTGAGAAGGGTCTCCGTAACCAGTGGAATGATTAGAGTGTGTAGACCCG a       N  Q  L  T  T  L  P  R  G  I  G  H  L  T  N  L  T  H  L  G   -

CTTGGAGAGAACCTACTTACTCACCTTCCTGAAGAAATTGGTACACTGGAGAACCTAGAA
   1501 ---------+---------+---------+---------+---------+---------+ 1560
        GAACCTCTCTTGGATGAATGAGTGGAAGGACTTCTTTAACCATGTGACCTCTTGGATCTT a       L  G  E  N  L  L  T  H  L  P  E  E  I  G  T  L  E  N  L  E   -

GAACTGTATTTGAATGACAACCCCAACCTGCATAGCCTTCCCTTTGAGCTGGCACTCTGC
   1561 ---------+---------+---------+---------+---------+---------+ 1620
        CTTGACATAAACTTACTGTTGGGGTTGGACGTATCGGAAGGGAAACTCGACCGTGAGACG
```

AGCAAGCTTTCAATCATGAGTATTGAGAACTGTCCACTCAGTCACCTTCCACCTCAGATT
   1621  ---------+---------+---------+---------+---------+---------+  1680
         TCGTTCGAAAGTTAGTACTCATAACTCTTGACAGGTGAGTCAGTGGAAGGTGGAGTCTAA a        S  K  L  S  I  M  S  I  E  N  C  P  L  S  H  L  P  P  Q  I   -

GTTGCTGGGGGGCCTTCTTTCATCATTCAGTTCTTAAAGATGCAGGGTCCATATCGTGCC
   1681  ---------+---------+---------+---------+---------+---------+  1740
         CAACGACCCCCCGGAAGAAAGTAGTAAGTCAAGAATTTCTACGTCCCAGGTATAGCACGG a        V  A  G  G  P  S  F  I  I  Q  F  L  K  M  Q  G  P  Y  R  A   -

ATGGTCTGA
   1741  --------- 1749
         TACCAGACT a        M  V  *   -
```

FIG. 10D

```
      ATGAGTAGTAGTTTAGGAAAAGAAAAAGACTTTAAAGAGAAAGACCCCAAAGTACCGTCT
  1   ---------+---------+---------+---------+---------+---------+ 60
      TACTCATCATCAAATCCTTTTCTTTTTCTNAAATTTCTCTTTCTGGGGTTTCATGGCAGA a     M  S  S  S  L  G  K  E  K  D  F  K  E  K  D  P  K  V  P  S  -

GCCAAGGAAAGAGAAAAGGAGTCAAAAGCNTCAGGAGGCTTTGGGAAAGAGAGCAAAGAA
  61  ---------+---------+---------+---------+---------+---------+ 120
      CGGTTCCTTTCTCTTTTCCTCAGTTTTCGNAGTCCTCCGAAACCCTTTCTCTCGTTTCTT a     A  K  E  R  E  K  E  S  K  A  S  G  G  F  G  K  E  S  K  E  -

AAGGAACCTAAAGCCAAAGGGAAAGACGCCAAAGATGGAAAGAAGGAGTCCAGCGCTGCC
 121  ---------+---------+---------+---------+---------+---------+ 180
      TTCCTTGGATTTCGGTTTCCCTTTCTGCGGTTTCTACCTTTCTTCCTCAGGTCGCGACGG a     K  E  P  K  A  K  G  K  D  A  K  D  G  K  K  E  S  S  A  A  -

CAGCCAGGTGTGGCTTTTTCAGTCGACAATACCATCAAACGGCCAAATCCAGCACCCGGC
 181  ---------+---------+---------+---------+---------+---------+ 240
      GTCGGTCCACACCGAAAAAGTCAGCTGTTATGGTAGTTTGCCGGTTTAGGTCGTGGGCCG a     Q  P  G  V  A  F  S  V  D  N  T  I  K  R  P  N  P  A  P  G  -

ACTAGAAAAAAGTCCAGCAATGCTGAGGTCATTAAGGAGCTTAACAAATGCCGGGAGGAG
 241  ---------+---------+---------+---------+---------+---------+ 300
      TGATCTTTTTTCAGGTCGTTACGACTCCAGTAATTCCTCGAATTGTTTACGGCCCTCCTC a     T  R  K  K  S  S  N  A  E  V  I  K  E  L  N  K  C  R  E  E  -

AACTCAATGCGGTTGGACTTGTCCAAGAGGTCTATACATATACTGCCACCATCAGTCAAA
 301  ---------+---------+---------+---------+---------+---------+ 360
      TTGAGTTACGCCAACCTGAACAGGTTCTCCAGATATGTATATGACGGTGGTAGTCAGTTT a     N  S  M  R  L  D  L  S  K  R  S  I  H  I  L  P  P  S  V  K  -

GAGTTGACTCAACTCACAGAACTTTATTTATACAGTAACAAATTGCAGTCCCTCCCAGCA
 361  ---------+---------+---------+---------+---------+---------+ 420
      CTCAACTGAGTTGAGTGTCTTGAAATAAATATGTCATTGTTTAACGTCAGGGAGGGTCGT a     E  L  T  Q  L  T  E  L  Y  L  Y  S  N  K  L  Q  S  L  P  A  -

GAGGTGGGCTGTCTAGTCAATCTCATGACGCTGGCTCTCAGTGaGAATTCAcTcACCAGT
 421  ---------+---------+---------+---------+---------+---------+ 480
      CTCCACCCGACAGATCAGTTAGAGTACTGCGACCGAGAGTCACtCTTAAGtGAgTGGTCA a     E  V  G  C  L  V  N  L  M  T  L  A  L  S  E  N  S  L  T  S  -

TTGCcTGAcTcTCTTGATAACTTGAAGAAGCTGCGGATGCTTGATTTACGGCAtAATAAA
 481  ---------+---------+---------+---------+---------+---------+ 540
      AACGgACTgAgAGAACTATTGAACTTCTTCGACGCCTACGAACTAAATGCCGTaTTATTT
```

CTGAGAGAAATTCcTTCAGTGgtGTATAGGCTAGACTCTCTCACCACTcTCTATCTTcGC
541   ---------+---------+---------+---------+---------+---------+  600
      GACTCTCTTTAAGgAAGTCACcaCATATCCGATCTGAGAGAGTGGTGAgAGATAGAAgCG a        L  R  E  I  P  S  V  V  Y  R  L  D  S  L  T  T  L  Y  L  R   -

TTTAATCGCATAACTACTGTGGAAAAGGACATCAAAAACCTGCCGAAGCTCAGCATGcTC
601   ---------+---------+---------+---------+---------+---------+  660
      AAATTAGCGTATTGATGACACCTTTTCCTGTAGTTTTTGGACGGCTTCGAGTCGTACgAG a        F  N  R  I  T  T  V  E  K  D  I  K  N  L  P  K  L  S  M  L   -

AGCATCCGAGAGAACAAAATCAAGCAGCTGCCTGCTGAAATTGGTGAATTATGTAACCTC
661   ---------+---------+---------+---------+---------+---------+  720
      TCGTAGGCTCTCTTGTTTTAGTTCGTCGACGGACGACTTTAACCACTTAATACATTGGAG a        S  I  R  E  N  K  I  K  Q  L  P  A  E  I  G  E  L  C  N  L   -

ATTACCCTGGATGTAGCTCACAATCAACTTGAACACCTTCCAAAGGAGATTGGAAACTGC
721   ---------+---------+---------+---------+---------+---------+  780
      TAATGGGACCTACATCGAGTGTTAGTTGAACTTGTGGAAGGTTTCCTCTAACCTTTGACG a        I  T  L  D  V  A  H  N  Q  L  E  H  L  P  K  E  I  G  N  C   -

ACACAGATAACCAACCTTGACTTGCAGCACAATGACCTAcTGGACCTCCCAGATACAATA
781   ---------+---------+---------+---------+---------+---------+  840
      TGTGTCTATTGGTTGGAACTGAACGTCGTGTTACTGGATgACCTGGAGGGTCTATGTTAT a        T  Q  I  T  N  L  D  L  Q  H  N  D  L  L  D  L  P  D  T  I   -

GGAAACCTGTCCAGTTTAAATCGCCTTGGCCTGAGATACAATAGATTGTCAGCAATACCC
841   ---------+---------+---------+---------+---------+---------+  900
      CCTTTGGACAGGTCAAATTTAGCGGAACCGGACTCTATGTTATCTAACAGTCGTTATGGG a        G  N  L  S  S  L  N  R  L  G  L  R  Y  N  R  L  S  A  I  P   -

AGATCATTAGCAAAATGCAGTGCACTTGAGGAGTTAAATTTAGAGAACAATAACATTTCT
901   ---------+---------+---------+---------+---------+---------+  960
      TCTAGTAATCGTTTTACGTCACGTGAACTCCTCAATTTAAATCTCTTGTTATTGTAAAGA a        R  S  L  A  K  C  S  A  L  E  E  L  N  L  E  N  N  N  I  S   -

AcTCTACCAGAGAGTCTTTTATCCAGTCTTGTAAAATTGAATAGCTTGACCTTAGCTAGA
961   ---------+---------+---------+---------+---------+---------+  1020
      TgAGATGGTCTCTCAGAAAATAGGTCAGAACATTTTAACTTATCGAACTGGAATCGATCT a        T  L  P  E  S  L  L  S  S  L  V  K  L  N  S  L  T  L  A  R   -

AATTGCTTCCAGTTATATCCAGTGGGAGGTCCATCTCAGTTTTCCACCATTTATTCCCTC
1021  ---------+---------+---------+---------+---------+---------+  1080
      TTAACGAAGGTCAATATAGGTCACCCTCCAGGTAGAGTCAAAAGGTGGTAAATAAGGGAG
```

FIG. 11B

```
            N  C  F  Q  L  Y  P  V  G  G  P  S  Q  F  S  T  I  Y  S  L   - aACaTGGAACACAATCGAATCAACAAAATCCCATTTGGAATTTTTTCCAGAGCTAAAGTG
   1081 ---------+---------+---------+---------+---------+---------+ 1140
        tTGtACCTTGTGTTAGCTTAGTTGTTTTAGGGTAAACCTTAAAAAAGGTCTCGATTTCAC a           N  M  E  H  N  R  I  N  K  I  P  F  G  I  F  S  R  A  K  V   -

TTAAGTAAGCTGAATATGAAGGACAATCAGTTAACATCACTTCCTTTGGATTTTGGAACT
   1141 ---------+---------+---------+---------+---------+---------+ 1200
        AATTCATTCGACTTATACTTCCTGTTAGTCAATTGTAGTGAAGGAAACCTAAAACCTTGA a           L  S  K  L  N  M  K  D  N  Q  L  T  S  L  P  L  D  F  G  T   -

TGGACCAGTATGGTAGAATTGAATTTAGCGACTAATCAGCTCACAAAGATCCCAGAGGAT
   1201 ---------+---------+---------+---------+---------+---------+ 1260
        ACCTGGTCATACCATCTTAACTTAAATCGCTGATTAGTCGAGTGTTTCTAGGGTCTCCTA a           W  T  S  M  V  E  L  N  L  A  T  N  Q  L  T  K  I  P  E  D   -

GTGTCTGGTCTCGTTTCCCTTGAGGTTCTGATCTTATCGAACAACCTTCTAAAGAAGCTG
   1261 ---------+---------+---------+---------+---------+---------+ 1320
        CACAGACCAGAGCAAAGGGAACTCCAAGACTAGAATAGCTTGTTGGAAGATTTCTTCGAC a           V  S  G  L  V  S  L  E  V  L  I  L  S  N  N  L  L  K  K  L   -

CCCCACGGCCTTGGGAACCTCAGAAAGCTACGAGAGCTGGACCTGGAGGAGAACAAGCTG
   1321 ---------+---------+---------+---------+---------+---------+ 1380
        GGGGTGCCGGAACCCTTGGAGTCTTTCGATGCTCTCGACCTGGACCTCCTCTTGTTCGAC a           P  H  G  L  G  N  L  R  K  L  R  E  L  D  E  E  N  K  L   -

GAGTCCTTGCCCAATGAGATCGCGTATCTCAAGGATCTGCAGAAATTAGTCTTGACAAAC
   1381 ---------+---------+---------+---------+---------+---------+ 1440
        CTCAGGAACGGGTTACTCTAGCGCATAGAGTTCCTAGACGTCTTTAATCAGAACTGTTTG a           E  S  L  P  N  E  I  A  Y  L  K  D  L  Q  K  L  V  L  T  N   -

AACCAGTTGAGCACGCTTCCCAGAGGCATCGGTCACCTTACCAACCTCACGCACCTTGGT
   1441 ---------+---------+---------+---------+---------+---------+ 1500
        TTGGTCAACTCGTGCGAAGGGTCTCCGTAGCCAGTGGAATGGTTGGAGTGCGTGGAACCA a           N  Q  L  S  T  L  P  R  G  I  G  H  L  T  N  L  T  H  L  G   -

CTTGGAGAGAACCTGCTCACTCACCTTCCTGAGGAAATCGGTACACTGGAAAACCTAGAA
   1501 ---------+---------+---------+---------+---------+---------+ 1560
        GAACCTCTCTTGGACGAGTGAGTGGAAGGACTCCTTTAGCCATGTGACCTTTTGGATCTT a           L  G  E  N  L  L  T  H  L  P  E  E  I  G  T  L  E  N  L  E   -

GAACTGTATTTGAACGACAACCCCAACCTTCACAGCCTCCCCTTTGAGCTTGCTCTCTGC
   1561 ---------+---------+---------+---------+---------+---------+ 1620
        CTTGACATAAACTTGCTGTTGGGGTTGGAAGTGTCGGAGGGGAAACTCGAACGAGAGACG
```

AGCAAGCTGTCAATCATGAGTATTGAGAACTGTCCACTCAGTCACCTCCCACCTCAAATT
1621 ---------+---------+---------+---------+---------+---------+ 1680
     TCGTTCGACAGTTAGTACTCATAACTCTTGACAGGTGAGTCAGTGGAGGGTGGAGTTTAA a       S  K  L  S  I  M  S  I  E  N  C  P  L  S  H  L  P  P  Q  I  -

GTTGCTGGAGGGCCTTCGTTCATTATTCAGTTCTTAAAGATGCAGGGTCCATATCGTGCC
1681 ---------+---------+---------+---------+---------+---------+ 1740
     CAACGACCTCCCGGAAGCAAGTAATAAGTCAAGAATTTCTACGTCCCAGGTATAGCACGG a       V  A  G  G  P  S  F  I  I  Q  F  L  K  M  Q  G  P  Y  R  A  -

ATGGTCTGA
1741 --------- 1749
     TACCAGACT a       M  V  *  -
```

FIG. 11D let-60 ras genomic BamHI-XhoII fragment Length: 7183

```
   1 ggatcctatt gaagtgggtg ttttcgttgc atatttcaac atattttaat
  51 tgaaagtgtg gcttatttct tgttgacagc cctattttaa aactaaatat
 101 cactaaaatt ataatgtttg gtgaaaattg ttccaaaaag tcacaagttc
 151 gtgttttcat ggcacatttc aagcaacttt taatatattt ttttccaga
 201 ctaccgagga aaaacttta tttaaaaata cactgttgag aatggtatat
 251 ttccatcata attttacct accaaacgta ttgaaactgt ggaaaagtct
 301 gtggaaaaaa tgccgaattt ccaaattaaa tgtgactttt tgtgaaaatt
 351 caagacgtta tcgaagccat gtttgaaaaa agtttgcata tctaatatta
 401 ttttttgagaa aacttgaagt ttataaaact gttagattag ttgaaaacta
 451 accgtttcga aaattcaata atgaaatatc tgttttcagg ttttcatttc
 501 ctctagttgc tcatttcaat atattttaat atcaaattct actggaaagt
 551 atgtgtcatt tcttgttgac accactattt tcaaactaaa taaataccac
 601 gataattata tattttgcaa aaattgttca aaaagtatca agttttctcg
 651 ttcttggcat atttcatgca atttgtaatt cttttgtct cagttatgtc
 701 ataactttt ctaaaaatcc taagttattc tagattattt gggagcaaac
 751 attttagaa attcccaaag tagattaaca aagaaaattc aaatataaat
 801 ctactggaca ttcaaagaaa agcacttaga caatttgaat cgaattcctc
 851 aaattcttga actattttt agaggatttc aattggacag aaagaatctc
 901 aagcacttaa cgtcggcgga aatagttttt tttttcaaa aagagaccac
 951 cgcctttgct agaaacgaaa attgcatgcg ttccattaaa taattcaatt
1001 catcgttatc accatccttc gtcgtcgtcg ttatcgtcag aaacagatag
1051 ggatgggtcg atacaaaaag aaagtggaca gttcttttct ctcactcttt
1101 ttctctttta caaatcacac ttgtttcgtc tcacacacgc tcacttcttg
1151 tctcttctcc caacagtcgt cgcaaaaccg tcaaaagcgt agcggctgtc
1201 gcgtcgcggt cgttcgtgtc tatgcatcac cgtttctagt gctctctaat
1251 tgtcccgccg tagcagtagc agcagtagca gcggcatggt ggggaccgca
1301 ctcctttatc ttttactctt actttgtgtg tgtgtatggg gggtgcgaga
1351 gaaagagata aaaagaaag aaagagagag tgtgtggttt ctgtgcttct
1401 gtgcactcca gagcctcgga tttcttttcc tatgaacttc atttctcgtc
1451 tccatcatca gaaggaagaa gaattcttca gaatcttgca cttgaagcgt
1501 tttctgccta tttattttct cctcccgagt tcatctctct attcgtcttt
1551 agcttaatcc attttattag gcacgcaccc gctccttggt tcaaccaaat
1601 gagaagatag aaaagatgga gcaacgcatc ccaaattgtg tgataggatt
1651 aaagtagtgt ggaagaaaaa aaaatgcaga gtgagagaag gggcagtctt
1701 cttttccggt cttactaatc ctaacgtctt ctttttcctt cctatctctc
1751 atctctcaac ttctgaaata gttgagatga gtgatttcgt aagttcatta
1801 ttcttttttg tcagttttttg cttatagttc ctacgggaat cattgtttct
1851 taaacatgct acttctttaa acaatttata tttaacaaag taaaattgaa
1901 cgttttttta aaaactttct aactgaattt cgtaaattta tttgtttcct
1951 tgtgaaaaat gcttgtcagg aaaacttttac ttctctacgt ctcaatctct
2001 gcaatctttt aacgagagat cggagaattt tgtattggaa aagtgaaaaa
2051 gaaaaatgaa agagacccac tcgacactga gggcgaccga aaagaaaccg
2101 acgaaaaaaa acgacgattc gagccatttg tcagcgacaa taagtggtcg
2151 ggtcgcacca ctgtccgccg tctcaccgat tttaacatta tattgtcccc
2201 cttttttcttc atcgctttga aatcaatttt tgatgaagtg aagacctttt
2251 ttctcctggt ttttttttta ataattgcat tacccccattt tttaaagttc
2301 aaaattactc aaactatttg aattcttctt ttttcaaat tgtaatgact
2351 cattctccgt cgtcttcaaa tagttactca ttccgactca ccacctagtt
2401 tattaacagg aaagttcatt ctttttctat cttccaatt attctcaagt
2451 agtcatcatc ggttttttat ttctttcctg gtagttactc tcctttatcg
2501 aaactttttt ttgaaaaaaa aaagaaacgg aattctgagt atgccgatag
2551 gcagagctgc tctttggcag tgctcccaca gaaatccttc tccacttcgt
2601 tttctcattt ccatctctat tttacatttt tccatattca actatgcgtc
2651 ttttttcaga aagggtaat gacggagtac aagcttgtgg tagttggaga
2701 tggaggagtt ggtaaatcag cactcaccat tcaactcatc cagaatcact
2751 ttgtcgaaga atacgacccg accatagagg acagctacag aaagcaggtg
2801 agaaatcatt gggaacatcc gctacacaca tgtggtggga gcaaattgaa
2851 cgaaaatgat ggcatttgaa attgaacaaa aaaacgatga gtcagaagtt
2901 tggaagtttt ttgaaacaca tcgagctgtt taattgattc caaagacgaa
```

FIG. 12A

```
2951  taaatcgtgc tgaaacacga aaaattccga aattttcgaa aaaaaaccaa
3001  tttttcgtgt tttggacacg acattataaa atggctggaa ctgaaaaaaa
3051  tggctcgaat catgattttt cattgtcccc cgaaaattct cacaaaaaaa
3101  aattggaaaa ccgaaaattt tagttttgc aaaaaccgga aaaattctga
3151  aaacactcca aaatcgatat ttctcagacg aatttcaata attacattcc
3201  gttttacgtt ttatacaaaa aacagaaatt tcactttttt tttgagaaag
3251  ggcccaaaac tttttttag atttttgtt ttttaaagc aaatcgataa
3301  accagcatgc ctgctcgtgt cgtgtgagga gtataaattt tttaaacgt
3351  atattcatct ttaaactctg aaattcagaa tattattgag ccctaatttt
3401  cagtgttttc atttgagttt taaccagta aaaatagttt ttcagttta
3451  aaaattgctc cgagagctag tttttaaata ttctaatttc aggttgtgat
3501  agacggtgag acatgcctcc tcgacatatt ggataccgcc ggacaagaag
3551  aatattcggc gatgcgtgat cagtacatga ggacaggcga aggatttctg
3601  ttggttttcg ccgtcaacga ggctaaatct ttcgagaatg tcgctaacta
3651  ccgcgagcag attcggaggg taaaggattc agatgatgtg agttttttt
3701  gttgaaatta tcagtcaatg gttgaatatt tgtatttctt ctaggttcct
3751  atggtcttgg tagggaataa atgtgatttg tcatctcgat cagtcgactt
3801  ccgaacagtc agtgagacag caaagggtta cggtattccg aatgtcgaca
 851  catctgccaa aacgcgtatg ggagttgatg aagcatttta cacacttgtt
3901  agagaaattc gcaaggtaat ttttagtta aaaatttaaa ttaaaaataa
3951  tgtttttaat gtacaattaa ggtacaaatt cagtcattat tatatgaaaa
4001  ttgaaagacg cgagattttg atatttcgc gccaaaaata cgacacccgg
4051  tctgttcgat ttgctccttc aaatattatg gtaactttat actgtcgtta
4101  cagcggaatt ttcatcaatt tttttaagtt ttcgatatta taaaaatatt
4151  taaaaacaca gcagttttaa taaatcggtg aaaattaccc cagaaacgaa
4201  atattaaagt tactgtattc tttaaaggcg cacatacgtt tgcatttaac
4251  acaaattcat cgtgtcgaga ccgggcaccg catctttaat ttgaaaatcg
4301  ccaaatgttg catttgagta atacaaaaac gttgttttta aaaatttct
4351  gttttgtaaa gctctaaaat gttattattg ttatcaacag tttcaagttt
4401  ccattttttca ctaaaaacga aaaatgtaag tttttccgat atttcgaaac
4451  aaaagctcaa agtttggtc atttcttaa tttttaaaga aaattatatg
4501  ttttctttg ttttttttct caccagcatg cacaaaatct gataaaaaat
4551  tgagttttat tgttaatttt ctaaaaaaa ttttgatgac accctagatt
4601  gatatccgaa agatttaata atgtttctt tttatttcag catcgtgagc
4651  gtcacgacaa taataagcca caaagaaga agaagtgtca aataatgtga
4701  ttcagcgtcg ggaattgccc aatttcgcca actcatttc agtcgtgtca
4751  actcccaccc aattatcctt tctcgtactt ttttggtaca ttttcattat
4801  tcatttatct gttttatctg aaacttgtga tcgatcctct tccgcctcta
4851  catactcttc gaatttccac cttttttct ctatgcatcg attgaacttg
4901  ttctctcgtc tgctcgtcat tatttttct ccttttttt cttcatcctt
4951  cattctaatt cctcatcttt cgcttagccc aaatctccat tcattcatag
5001  gtgtcaaaac tagctgtagt gtgtgatcca tatctaaaac atgcatccga
5051  acccctcct cgttccaaaa ttggccaact ctaccaaaaa aaacatcgca
5101  ccatttttt ttcactttct ctgcatattt tcagaatgtt tgtattgctt
5151  ttttgatgct ttattcccct tcctcgtttt catacaaatt attggcctca
5201  tctatttca gaagttctct gaaaattaaa ttcttttgca tctgccggtc
5251  gttccgttta tttttctct gttcctctc attttgtca agtaattatt
5301  tctctttcat taactataat atagatacaa ttagacccca tttctcatac
5351  attttctgaa catctgaaag ttttgctcc ctcgtattgc attcattttt
5401  ctctattcct ctacattta tagtcctatc tgaatatat attcctattc
5451  ttttgatcaa gtttttatta ttattttatt ttcaaggaag tattgcaatg
5501  atataaattt taaaagcta atattatttt tttaaatcta ttcaactata
5551  ttttgttaat ttcagtgtta tatttgacc tcgccatcgg agcatgattt
5601  taaaaaaac taaatttaat ttattagaat gacgagaaaa aggaaaaatg
5651  tagagtctga tgagaatcct ccagcgaaaa actcatttga aggatacgga
5701  tatgctgctg ctgatgctga gaagaagcca caggaggaga gaaacaattt
5751  cagaactttt ctagccaaaa atgaacgatt tggaagtgga aatcgaggtg
5801  gaggaggtcg tggaagagga ggagatggtg gatttagaag aaatgataga
5851  ggtggacgtg gtggtggtgg aagaggattc ggtggtaaca gagaattcag
5901  tgccggagat tttgagaagg tttgtgtcag atggtgtcgt gagtgatgta
5951  gcgtctctgg ctttttaaac tcaaaattac agaaaaagtt tcgatatgtc
6001  gagttaaaaa cattctaaa atttgtatta ttttgcaaaa aataaaaaaa
6051  agccgaatta tttttgaatt tttagtcat ttcctggac aaaaattgtt
6101  caaatgtgg aattataggt tttagaccaa tttcatttta tcgaatttcg
6151  ttcggatttt cgaggtttct ttccgaaaaa ctgtctgaaa aaatgagcgc
6201  gggaattcac aaatatttca gtattttttt gaaattgaat tttaaaaaat
```

FIG. 12B

```
6251  ttatattcga  tatattgaga  cttttttctg  tgaagaatcg  ataaaatgaa
6301  ctccaaagcg  ctccctaggc  aattaccaca  aaaacgtata  tatttattta
6351  atttacagca  atacggtcga  gttggcggcg  gtgatgacac  gaattcagga
6401  caaccggata  gctacggaca  agctgattcg  gcttcattca  acgactctcg
6451  accagatgga  gatggtcgtg  aatttccgaa  agaaattgtt  ggttatctga
6501  gaagtattga  acaaatcaag  aagaaagagg  gaaaaattga  agatttatt
6551  ctggaaaagt  gtgctgaaga  agttgttggc  caggagaaaa  ctcttctctc
6601  gtggacagaa  gcagccgttg  ttgttgaatc  tgtatttgga  agttgtccta
6651  aaggagcagc  tctcttcctt  tcatcgattt  ctcgtctcaa  gcataaaaca
6701  ttagctgagc  tgattttcgg  aggagctagt  gctaggacaa  ttgaaaattt
6751  gatattctcg  atgtgcccaa  tcgccgaatc  agaacatgtg  gagattcttc
6801  aaaaactagc  aggaattctt  atggataact  gggcggatgc  tgttacaaca
6851  caaccttcga  gttttctgat  tcgagctatt  gtctgggtgt  gttgtggatt
6901  gtcagcaagg  ccaaaggttg  gagaggaaaa  gaaaagaaat  tacaaaggac
6951  aagaaatgaa  ggctagcttg  aagaatgttt  atgaaaaact  tgcaatcttg
7001  gcattcgatg  agaatcttaa  taaaaccttt  atggattctc  cgattttgt
7051  gacactattt  caagatttta  ttgaagccga  tgggctttgg  ggagacaaaa
7101  gaggtgatga  atatgtgaag  aagaagctcg  aaaaggaaga  tattgaagga
7151  atctcgaagg  catggtattc  atcaaatgga  tct
```

FIG. 12C mutant let-60 ras genomic BamHI-XhoII fragment Length: 7183

```
   1 ggatcctatt gaagtgggtg ttttcgttgc atatttcaac atatttaat
  51 tgaaagtgtg gcttatttct tgttgacagc cctatttaa aactaaatat
 101 cactaaaatt ataatgtttg gtgaaaattg ttccaaaaag tcacaagttc
 151 gtgttttcat ggcacatttc aagcaacttt taatatattt ttttttccaga
 201 ctaccgagga aaaactttta tttaaaaata cactgttgag aatggtatat
 251 ttccatcata atttttacct accaaacgta ttgaaactgt ggaaaagtct
 301 gtggaaaaaa tgccgaattt ccaaattaaa tgtgactttt tgtgaaaatt
 351 caagacgtta tcgaagccat gtttgaaaaa agtttgcata tctaatatta
 401 tttttgagaa aacttgaagt ttataaaact gttagattag ttgaaaacta
 451 accgtttcga aaattcaata atgaaatatc tgttttcagg ttttcatttc
 501 ctctagttgc tcatttcaat atattttaat atcaaattct actggaaagt
 551 atgtgtcatt tcttgttgac accactattt tcaaactaaa taaataccac
 601 gataattata tattttgcaa aaattgttca aaaagtatca agttttctcg
 651 ttcttggcat atttcatgca atttgtaatt cttttgtct cagttatgtc
 701 ataacttttt ctaaaaatcc taagttattc tagattattt gggagcaaac
 751 attttttagaa attcccaaag tagattaaca aagaaaattc aaatataaat
 801 ctactggaca ttcaaagaaa agcacttaga caatttgaat cgaattcctc
 851 aaattcttga actattttt agaggatttc aattggacag aaagaatctc
 901 aagcacttaa cgtcggcgga aatagttttt tttttcaaa aagagaccac
 951 cgcctttgct agaaacgaaa attgcatgcg ttccattaaa taattcaatt
1001 catcgttatc accatccttc gtcgtcgtcg ttatcgtcag aaacagatag
1051 ggatgggtcg atacaaaaag aaagtggaca gttcttttct ctcactcttt
1101 ttctctttta caaatcacac ttgtttcgtc tcacacacgc tcacttcttg
1151 tctcttctcc caacagtcgt cgcaaaaccg tcaaaagcgt agcggctgtc
1201 gcgtcgcggt cgttcgtgtc tatgcatcac cgtttctagt gctctctaat
1251 tgtcccgccg tagcagtagc agcagtagca gcggcatggt ggggaccgca
1301 ctcctttatc ttttactctt actttgtgtg tgtgtatggg gggtgcgaga
1351 gaaagagata aaaagaaag aagagagag tgtgtggttt ctgtgcttct
1401 gtgcactcca gagcctcgga tttcttttcc tatgaacttc atttctcgtc
1451 tccatcatca gaaggaagaa gaattcttca gaatcttgca cttgaagcgt
1501 tttctgccta tttattttct cctcccgagt tcatctctct attcgtcttt
1551 agcttaatcc attttattag gcacgcaccc gctccttggt tcaaccaaat
1601 gagaagatag aaaagatgga gcaacgcatc ccaaattgtg tgataggatt
1651 aaagtagtgt ggaagaaaaa aaaatgcaga gtgagagaag gggcagtctt
1701 cttttccggt cttactaatc ctaacgtctt cttttttcctt cctatctctc
1751 atctctcaac ttctgaaata gttgagatga gtgatttcgt aagttcatta
1801 ttcttttttg tcagttttg cttatagttc ctacgggaat cattgtttct
1851 taaacatgct acttctttaa acaatttata tttaacaaag taaaattgaa
1901 cgtttttta aaaactttct aactgaattt cgtaaattta tttgtttcct
1951 tgtgaaaaat gcttgtcagg aaaactttac ttctctacgt ctcaatctct
2001 gcaatctttt aacgagagat cggagaattt tgtattggaa aagtgaaaaa
2051 gaaaaatgaa agagacccac tcgacactga gggcgaccga aagaaaccg
2101 acgaaaaaa acgacgattc gagccatttg tcagcgacaa taagtggtcg
2151 ggtcgcacca ctgtccgccg tctcaccgat tttaacatta tattgtcccc
2201 cttttcttc atcgctttga aatcaatttt tgatgaagtg aagaccttt
2251 ttctcctggt tttttttta ataattgcat taccccattt tttaaagttc
2301 aaaattactc aaactatttg aattcttctt tttttcaaat tgtaatgact
2351 cattctccgt cgtcttcaaa tagttactca ttccgactca ccacctagtt
2401 tattaacagg aaagttcatt cttttctat cttctcaatt attctcaagt
2451 agtcatcatc ggtttttat ttctttcctg gtagttactc tcctttatcg
2501 aaactttttt ttgaaaaaaa aaagaaacgg aattctgagt atgccgatag
2551 gcagagctgc tctttggcag tgctcccaca gaaatccttc tccacttcgt
2601 tttctcattt ccatctctat tttacatttt tccatattca actatgcgtc
2651 tttttcaga aagggtaat gacggagtac aagcttgtgg tagttagaga
2701 tggaggagtt ggtaaatcag cactcaccat tcaactcatc cagaatcact
2751 ttgtcgaaga atacgacccg accatagagg acagctacag aaagcaggtg
2801 agaaatcatt gggaacatcc gctacacaca tgtggtggga gcaaattgaa
2851 cgaaaatgat ggcatttgaa attgaacaaa aaaacgatga gtcagaagtt
2901 tggaagtttt ttgaaacaca tcgagctgtt taattgattc caaagacgaa
```

FIG. 13A

```
2951  taaatcgtgc tgaaacacga aaaattccga aattttcgaa aaaaaaccaa
3001  tttttcgtgt tttggacacg acattataaa atggctggaa ctgaaaaaaa
3051  tggctcgaat catgatttt  cattgtcccc cgaaaattct cacaaaaaaa
3101  aattggaaaa ccgaaaattt tagttttgc  aaaaaccgga aaaattctga
3151  aaacactcca aaatcgatat ttctcagacg aatttcaata attacattcc
3201  gttttacgtt ttatacaaaa aacagaaatt tcactttttt tttgagaaag
3251  ggcccaaaac ttttttttag atttttgtt  ttttaaagc  aaatcgataa
3301  accagcatgc ctgctcgtgt cgtgtgagga gtataaattt ttttaaacgt
3351  atattcatct ttaaactctg aaattcagaa tattattgag ccctaattt
3401  cagtgttttc atttgagttt ttaaccagta aaaatagttt ttcagttta
3451  aaaattgctc cgagagctag ttttaaata ttctaatttc aggttgtgat
3501  agacggtgag acatgcctcc tcgacatatt ggataccgcc ggacaagaag
3551  aatattcggc gatgcgtgat cagtacatga ggacaggcga aggatttctg
3601  ttggttttcg ccgtcaacga ggctaaatct ttcgagaatg tcgctaacta
3651  ccgcgagcag attcggaggg taaggattc  agatgatgtg agttttttt
3701  gttgaaatta tcagtcaatg gttgaatatt tgtatttctt ctaggttcct
3751  atggtcttgg tagggaataa atgtgatttg tcatctcgat cagtcgactt
3801  ccgaacagtc agtgagacag caaagggtta cggtattccg aatgtcgaca
851   catctgccaa aacgcgtatg ggagttgatg aagcatttta cacacttgtt
3901  agagaaattc gcaaggtaat tttttagtta aaaatttaaa ttaaaaataa
3951  tgtttttaat gtacaattaa ggtacaaatt cagtcattat tatatgaaaa
4001  ttgaaagacg cgagattttg atattttcgc gccaaaaata cgacacccgg
4051  tctgttcgat ttgctccttc aaatattatg gtaactttat actgtcgtta
4101  cagcggaatt ttcatcaatt ttttaagtt  ttcgatatta taaaaatatt
4151  taaaaacaca gcagtttaa  taaatcggtg aaaattaccc cagaaacgaa
4201  atattaaagt tactgtattc tttaaggcg  cacatacgtt tgcatttaac
4251  acaaattcat cgtgtcgaga ccgggcaccg catctttaat ttgaaaatcg
4301  ccaaatgttg catttgagta atacaaaaac gttgtttta  aaaattttct
4351  gttttgtaaa gctctaaaat gttattattg ttatcaacag tttcaagttt
4401  ccattttca  ctaaaaacga aaaatgtaag ttttccgat  atttcgaaac
4451  aaaagctcaa agtttggtc  attttcttaa ttttaaaga  aaattatatg
4501  ttttcttttg ttttttttct caccagcatg cacaaaatct gataaaaaat
4551  tgagttttat tgttaatttt ctaaaaaaaa ttttgatgac accctagatt
4601  gatatccgaa agatttaata atgttttctt tttatttcag catcgtgagc
4651  gtcacgacaa taataagcca caaagaaga  agaagtgtca aataatgtga
4701  ttcagcgtcg ggaattgccc aatttcgcca actcatttc  agtcgtgtca
4751  actcccaccc aattatcctt tctcgtactt ttttggtaca ttttcattat
4801  tcatttatct gttttatctg aaacttgtga tcgatcctct tccgcctcta
4851  catactcttc gaatttccac cttttttct  ctatgcatcg attgaacttg
4901  ttctctcgtc tgctcgtcat tatttttct  cctttttt   cttcatcctt
4951  cattctaatt cctcatcttt cgcttagccc aaatctccat tcattcatag
5001  gtgtcaaaac tagctgtagt gtgtgatcca tatctaaaac atgcatccga
5051  accccctcct cgttccaaaa ttggccaact ctaccaaaaa aaacatcgca
5101  ccatttttt  ttcactttct ctgcatattt tcagaatgtt tgtattgctt
5151  ttttgatgct ttattccct  tcctcgtttt catacaaatt attggcctca
5201  tctattttca gaagttctct gaaaattaaa ttcttttgca tctgccggtc
5251  gttccgttta ttttttctct gtttcctctc atttttgtca agtaattatt
5301  tctctttcat taactataat atagatacaa ttagacccca tttctcatac
5351  attttctgaa catctgaaag ttttgctcc  ctcgtattgc attcattttt
5401  ctctattcct ctacattta  tagtcctatc tgaatataat attcctattc
5451  ttttgatcaa gttttatta  ttattttatt ttcaaggaag tattgcaatg
5501  atataaattt taaaagcta  atattatttt tttaaatcta ttcaactata
5551  ttttgttaat ttcagtgtta tattttgacc tcgccatcgg agcatgattt
5601  taaaaaaac  taaatttaat ttattagaat gacgagaaaa aggaaaaatg
5651  tagagtctga tgagaatcct ccagcgaaaa actcatttga aggatacgga
5701  tatgctgctg ctgatgctga gaagaagcca caggaggaga gaaacaattt
5751  cagaactttt ctagccaaaa atgaacgatt tggaagtgga aatcgaggtg
5801  gaggaggtcg tggaagagga ggagatggtg gatttagaag aaatgataga
5851  ggtggacgtg gtggtggtgg aagaggattc ggtggtaaca gagaattcag
5901  tgccggagat tttgagaagg tttgtgtcag atggtgtcgt gagtgatgta
5951  gcgtctctgg ctttttaaac tcaaaattac agaaaaagtt tcgatatgtc
6001  gagttaaaaa catttctaaa atttgtatta ttttgcaaaa aataaaaaaa
6051  agccgaatta ttttgaatt  ttttagtcat ttcctggac  aaaaattgtt
6101  caaaatgtgg aattataggt tttagaccaa tttcatttta tcgaatttcg
6151  ttcggatttt cgaggtttct ttccgaaaaa ctgtctgaaa aaatgagcgc
6201  gggaattcac aaatatttca gtatttttt  gaaattgaat tttaaaaaat
```

FIG. 13B

```
6251  ttatattcga tatattgaga ctttttctg  tgaagaatcg ataaaatgaa
6301  ctccaaagcg ctccctaggc aattaccaca aaaacgtata tatttattta
6351  atttacagca atacggtcga gttggcggcg gtgatgacac gaattcagga
6401  caaccggata gctacggaca agctgattcg gcttcattca acgactctcg
6451  accagatgga gatggtcgtg aatttccgaa agaaattgtt ggttatctga
6501  gaagtattga acaaatcaag aagaaagagg gaaaaattga agatttatt
6551  ctggaaaagt gtgctgaaga agttgttggc caggagaaaa ctcttctctc
6601  gtggacagaa gcagccgttg ttgttgaatc tgtatttgga agttgtccta
6651  aaggagcagc tctcttcctt tcatcgattt ctcgtctcaa gcataaaaca
6701  ttagctgagc tgattttcgg aggagctagt gctaggacaa ttgaaaattt
6751  gatattctcg atgtgcccaa tcgccgaatc agaacatgtg gagattcttc
6801  aaaaactagc aggaattctt atggataact gggcggatgc tgttacaaca
6851  caaccttcga gttttctgat tcgagctatt gtctgggtgt gttgtggatt
6901  gtcagcaagg ccaaaggttg gagaggaaaa gaaaagaaat tacaaaggac
6951  aagaaatgaa ggctagcttg aagaatgttt atgaaaaact tgcaatcttg
7001  gcattcgatg agaatcttaa taaaaccttt atggattctc cgattttgt
7051  gacactattt caagatttta ttgaagccga tgggctttgg ggagacaaaa
7101  gaggtgatga atatgtgaag aagaagctcg aaaaggaaga tattgaagga
7151  atctcgaagg catggtattc atcaaatgga tct
```

FIG. 13C

RAS SUPPRESSOR SUR-8 AND RELATED COMPOSITIONS AND METHODS

This invention was made during the course of work supported by the United States Government, under the National Institutes of Health, Grant Number GM47869, and the Department of Defense, Grant Number DAMD17-96-1-6117. As such, the United States Government may have certain rights to this invention.

FIELD OF THE INVENTION

The present invention relates to Ras suppressors, in particular the Ras suppressor SUR-8.

BACKGROUND OF THE INVENTION

The Ras family of proteins play critical roles in cell proliferation, differentiation, and cell migration in response to extracellular signals. Ras proteins are 21 kD membrane-bound GTPases that act as molecular switches, cycling between an inactive GDP-bound state and an active GTP-bound state. In the most well studied Ras-mediated signal transduction pathways, Ras is activated by receptor tyrosine kinases (RTK) through guanine nucleotide exchange factors that promote GTP binding and a change in Ras conformation to an active state (See e.g., McCormick, Nature 363, 15 [1993]). GTP-bound Ras then binds to the serine/threonine kinase Raf and recruits it to plasma membrane where it is activated. Once activated, Raf phosphorylates and activates the dual specific kinase MEK, which in turn phosphorylates and activates MAP kinase. Activated MAP kinase (MAPK) is proposed to regulate the activity of multiple targets including transcription factors for various physiological functions (Marshall, Curr. Opin. Genet. Dev. 4, 82 [1994]). Although this model for Ras-dependent signal transduction has been heavily studied, there has been almost no development or identification of effectors that regulate Ras signal transduction or that alter the associated cellular and physiological events stimulated by Ras. Little is known about the nature of Ras effectors or the pathways they control (Rubin et al., WO 97/21820 [1997]).

Recent studies using various model systems including biochemical studies in mammalian tissue culture and genetics in C. elegans and Drosophila suggest that the RTK-Ras-MAPK-mediated signal transduction pathway is not a simple linear pathway, but is likely part of complicated signal transduction network (Katz, and McCormick, Curr. Opin. Genet Dev. 7, 75–79 [1997]; Sundaram and Han, Cell 83, 889 [1995]; and Kornfeld, Trends Genet. 13, 55 [1997]). Thus, a series of converging and diverging signalling pathways are likely responsible for the diverse cellular responses mediated by Ras. In recent years, several potential Ras effectors in addition to Raf, including PI3 kinase and Ral GDS, have been described (Katz, supra) and are candidates for defining branch points of Ras signalling. However, these effectors cannot account for all of the cellular responses mediated by Ras (See e.g., White et al., Cell 80, 533 [1995]) and have not been sufficiently characterized.

Adding to the complexity of the various signaling processes is the collaboratory roles of multiple factors and signaling branches in regulating the output of the signal. The main players of the RTK-Ras-MAPK pathway may be essential elements of a given signaling process, but there are other factors that feed into or out of this pathway that may play important regulatory functions to ensure maximal activity of the pathway and to tighten the regulation of the signal. For example, the ksr genes were identified as suppressors of activated ras in C. elegans and Drosophila (Sundaram and Han, Cell 83, 889 [1995]; Kornfeld et al., Cell 83, 903 [1995]; and Therrien et al., Cell 83, 879 [1995]), however, their biochemical relation to the Ras pathway is still not well understood. In C. elegans, it has been shown that mutations in the ksr-1 gene do not obviously disrupt vulval signal transduction mediated by ras (i.e., a pathway controlled by ras in C. elegans). However, the ksr-1 activity becomes essential when the activity in the main pathway is compromised (Sundaram and Han, 1995, supra; and Kornfeld et al., 1995, supra).

The art is in need of additional regulators of the Ras signal transduction pathways. To gain regulatory control of Ras signalling and its physiological consequences (e.g., effects on cancer), new Ras effectors and their genes need to be identified and isolated. Without such developments, the ability to control Ras-mediated proliferation, differentiation, and cell migration will be severely limited.

SUMMARY OF THE INVENTION

The present invention relates to Ras suppressors, in particular the Ras suppressor SUR-8.

In one embodiment, the present invention provides an isolated nucleotide sequence encoding at least a portion of a SUR-8 protein. In some embodiments, the isolated nucleotide sequence encodes a SUR-8 protein selected from the group consisting of human SUR-8, murine SUR-8, and C. elegans SUR-8. In certain embodiments, the isolated nucleotide sequence is selected from the group consisting of SEQ ID NOS:1, 5, and 6. In another embodiment, the nucleotide sequence further comprises 5' and 3' flanking regions. In yet another embodiment, the nucleotide sequence further comprises intervening regions. In alternative embodiments, the nucleotide sequence comprises portions or fragments of the sequences described above.

In an another embodiment, the present invention provides vectors comprising a nucleotide sequence encoding at least a portion of SUR-8. In another embodiment, the present invention provides a host cell transformed with a vector comprising a nucleotide sequence encoding at least a portion of SUR-8. It is intended that the nucleotides, as well as the vector comprise deoxyribonucleotides and/or ribonucleotides. It is not intended that the vector be limited to any particular nucleotide sequences. It is also not intended that the host cell be limited to any particular cell type. The host cell may be contained within a living animal, as well as in culture (i.e., in cell cultures). In certain embodiments, the host cell is selected from the group consisting of bacteria, yeast, amphibian, and mammalian cells.

In one embodiment, the present invention provides an isolated peptide sequence comprising at least a fragment of SUR-8. In some embodiments, the isolated peptide sequence is selected from the group consisting of SEQ ID NOS:2, 7, and 8, and fragments thereof. The present invention also provides antibodies capable of specifically binding to any of the polypeptides described above. It is intended that the antibodies be produced using any suitable method known in the art, including polyclonal, as well as monoclonal antibodies.

The present invention also provides a polynucleotide sequence comprising at least fifteen nucleotides, capable of hybridizing under stringent conditions to at least a portion of an isolated nucleotide sequence encoding at least a portion of a SUR-8 protein. In certain embodiments, the polynucleotides sequence is selected from the group consisting of SEQ ID NOs:11–18.

The present invention also provides methods for detection of a polynucleotide encoding SUR-8 protein in a biological sample suspected of containing the polynucleotide encoding SUR-8, comprising the step of hybridizing at least a portion of the polynucleotide sequence capable of hybridizing under stringent conditions to at least a portion of an isolated nucleotide sequence encoding at least a portion of a SUR-8 protein, to nucleic acid of said biological sample to produce a hybridization complex. In one embodiment, the method further comprises the step of detecting the hybridization complex, wherein the presence of the hybridization complex correlates with the presence of a polynucleotide encoding SUR-8 in the biological sample. In some embodiments, the nucleic acid of the biological sample is amplified.

The present invention also provides a non-human animal overexpressing SUR-8 mRNA in the tissue of the non-human animal. In preferred embodiments, the SUR-8 is human SUR-8. However, SUR-8 mRNA from other species is also encompassed by the present invention. In one embodiment, the non-human animal is a member of the Order Rodentia.

The present invention also provides methods for producing the non-human transgenic animals, comprising the steps of introducing into an embryonal cell of a non-human animal a polynucleotide sequence encoding a SUR-8 protein; transplanting the embryonal target cell formed thereby, into a recipient female parent; and identifying at least one offspring containing the transgene, wherein the SUR-8 mRNA is overexpressed in the tissue of the offspring. In one embodiment, the SUR-8 mRNA is human SUR-8 mRNA. In an alternative embodiment, the SUR-8 protein is a mutant SUR-8 protein.

The present invention also provides a method for screening compounds for the ability to alter SUR-8 signal transduction (i.e., signal transduction pathways where SUR-8 is a component, either directly or indirectly), comprising providing: polypeptide sequence comprising at least a portion of SUR-8, polypeptide sequence comprising at least a portion of a protein known to interact (either directly of indirectly) with SUR-8; and one or more test compounds; combining in any order, the polypeptide sequence comprising at least a portion of SUR-8 and the polypeptide sequence comprising at least a portion of a protein known to interact with SUR-8, and the one or more test compounds; and detecting the presence or absence of an interaction (defined as any detectable interaction, such as covalent binding, physical association, direct or indirect activation or inhibition, etc.) between the polypeptide sequence comprising at least a portion of SUR-8 and the polypeptide sequence comprising at least a portion of a protein known to interact with SUR-8.

DESCRIPTION OF THE FIGURES

FIG. 3 shows an alignment of eighteen *C. elegans* SUR-8 LRRs with a comparison to yeast adenylate cyclase LRRs.

FIG. 4 shows the complete amino acid alignment of predicted SUR-8 protein sequences from human (Hs SUR-8), mouse (Mu SUR-8), and *C. elegans* (Ce SUR-8).

FIGS. 8A and 8B show results of a two-hybrid experiments undertaken to determine whether human SUR-8 could bind mammalian Ras. The interaction of human SUR-8 with three Ras family members, N-Ras, K-Ras 4B, and H-Ras was tested in the yeast two-hybrid system.

FIGS. 9A–9D show the complete DNA sequence (SEQ ID NO:1) and predicted amino acid sequence (SEQ ID NO:2) of *C. elegans* sur-8.

FIGS. 10A–10D show the complete DNA sequence (SEQ ID NO:6) and predicted amino acid sequence (SEQ ID NO:8) of human sur-8.

FIGS. 11A–11D show the complete DNA sequence (SEQ ID NO:5) and predicted amino acid sequence (SEQ ID NO:7) of murine sur-8.

FIGS. 12A–12C show the sequence of let-60 ras transgene (SEQ ID NO:9).

FIGS. 13A–13C show the sequence of mutant let-60 ras transgene where the nucleotide mutated at position 2696 is in bold (SEQ ID NO:10).

GENERAL DESCRIPTION OF THE INVENTION

Figure 1:
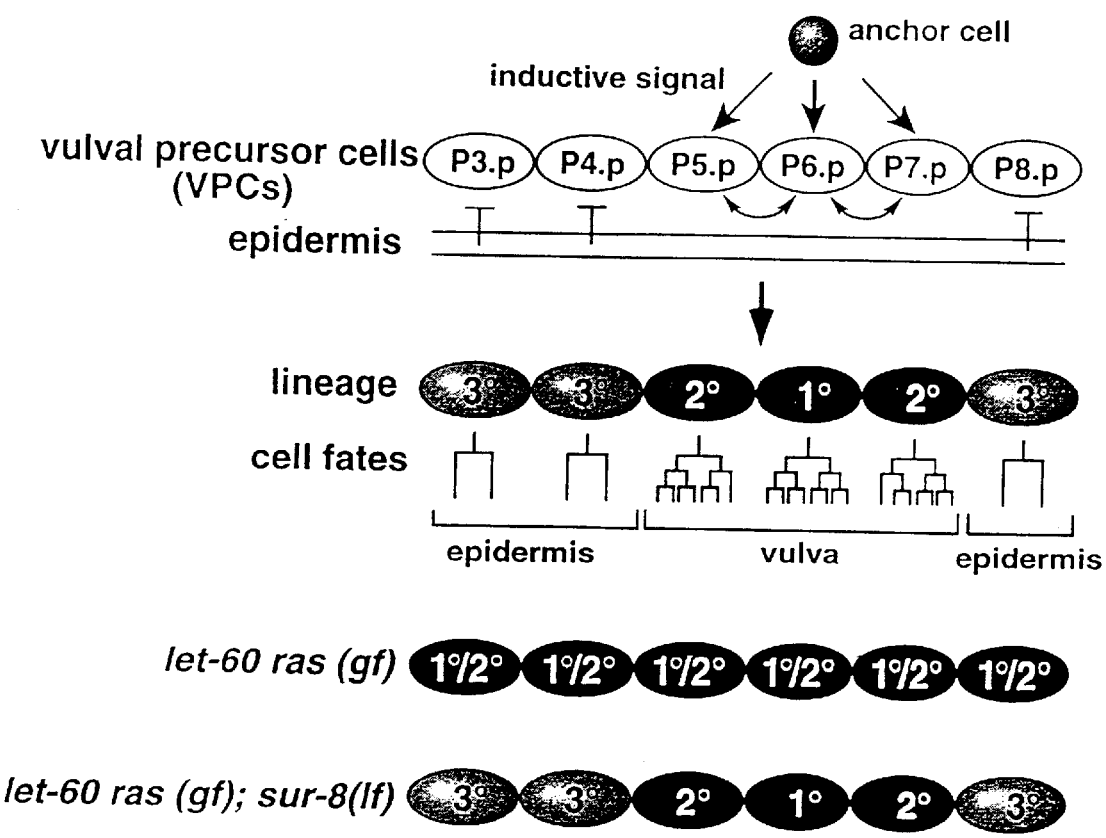
FIG. 1 shows a schematic representation of wild type and mutant cell fate specification during *C. elegans* vulval development.

The presently claimed invention relates to Ras suppressors. In particular, the presently claimed invention provides the sur-8 gene (e.g., human sur-8) and methods for identifying, characterizing, and isolating sur-8 genes, SUR-8 proteins, and other Ras effectors. The present invention further provides methods and compositions for targeted therapy directed to sur-8 abnormalities, methods for generating SUR-8 antibodies, and methods for using SUR-8 as a target for screening drugs against Ras.

The *C. elegans* sur-8 gene was the first sur-8 gene obtained using methods of the present invention. Prior to identification and isolation, a let-60 (i.e., a gene encoding a *C. elegans* Ras protein) gain-of-function transgenic strain of *C. elegans* was developed to allow for the screening of Ras suppressors. Transgenic animals were treated with mutagen and screening of progeny was conducted for suppressed F2 animals. These suppressor candidates were outcrossed to remove additional mutations from the genome. The animals that retained a suppressive phenotype underwent genetic mapping to assign each of the suppressors to one of the six *C. elegans* chromosomes. Mapping analysis identified a novel allele, ku167, where no known gene involved in the Ras pathway had previously been identified. The allele defines the sur-8 gene.

Characterization of the sur-8 gene demonstrated that ku167 is a loss-of-function mutation. Epistatic analysis indicated that sur-8 acts downstream or in parallel to let-60 ras and upstream of the lin-45 raf (i.e., a *C. elegans* gene encoding Raf). Because ras and raf have been shown to directly interact, this suggested that sur-8 defines a branch point either feeding into raf or out or ras, although an understanding of the mechanism is not necessary to practice the present invention.

The *C. elegans* sur-8 gene was then further mapped and cloned. Mapping located sur-8 at position 1.72 of chromosome IV in the *C. elegans* genome. This region is covered by mapped cosmids containing approximately 40 kb genomic fragment inserts constructed by the *C. elegans* genome project. The specific cosmid DNA containing the sur-8 gene, AC7, was identified by its ability to rescue the sur-8 phenotype. The AC7 cosmid was divided into small plasmids by digesting with restriction endonucleases and subcloning the fragments. A single subcloned 10 kb insert fragment was able to rescue activity. Based on the genome sequencing project, there was a single predicted gene located within the rescuing 10 kb fragment. A *C. elegans* mixed stage library was screened using a 2 kb DNA probe derived from the predicted region and the longest clones obtained were sequenced to obtain the sur-8 cDNA sequence (SEQ ID NO:1). A computer structure analysis predicted a 559 amino acid protein encoded by sur-8 (SEQ ID NO:2).

Human and mouse sur-8 genes were identified using homology searches with expressed sequence tag (EST) sequences deposited in the EST Genbank database, isolated, cloned, and characterized. Clones were obtained by probing human and mouse cDNA libraries using the 5' RACE strategy. Comparison of the predicted amino acid sequences of the human, mouse, and *C. elegans* sur-8 cDNAs revealed significant homology in the overall structure and sequence between the *C. elegans* SUR-8 and mammalian SUR-8.

Additional characterization revealed physical interactions between SUR-8 and Ras. A detailed description of these methods and compositions of the present invention are provided below.

DETAILED DESCRIPTION OF THE INVENTION

The ras mediated signal transduction pathway controls cell growth, differentiation, and proliferation in response to extracellular signals. In *C. elegans*, the ras pathway controls vulval cell fate specification in response to a growth factor signal. The *C. elegans* vulva is composed of 22 cells that are all the descendants of three vulval precursor cells (VPCs).

The present invention used *C. elegans*, a powerful genetic system, and its vulval development to identify and characterize genes that regulate the Ras-mediated signal transduction pathway. In *C. elegans*, there is a single known ras gene, let-60, that acts in a RTK-Ras-MAPK signal transduction pathway to control several cell fate specification decisions including vulval fate specification. The hermaphrodite vulva is derived from three of six vulval precursor cells (VPCs). Each of the six VPCs has the ability to adopt either a vulval cell fate or a non-vulval cell fate. The proper pattern of cell fate specification is determined by the combination of three signaling events as shown in FIG. 1, illustrating wild type and mutant cell fate specification during vulval development. In this figure, vulval precursor cells P3.p through P8.p form an equivalence group and each cell can take on a vulval cell fate or non vulval cell fate depending on the influence of multiple cell signaling events. An inductive signal from the neighboring anchor cell promotes primary vulval fates by activating a Ras pathway, an inhibitory signal from the surrounding hypodermis promotes tertiary fates and a lateral signal among induced cells promotes secondary fates. In wild type, three of six VPCs adopt a vulval cell fate, and the pattern of cell fate specification is 3° 3° 2° 1° 2° 3° (100% induction). The activated let-60 ras allele, n1046gf or G13E, can cause all six VPCs to adopt a vulval cell fate (1°/2°), resulting in a Multivulva phenotype and up to 200% induction. Mutations in the sur-8 gene suppress the Multivulva phenotype caused by activated let-60 ras to wild type, resulting in a Suppressed phenotype.

Figure 2:
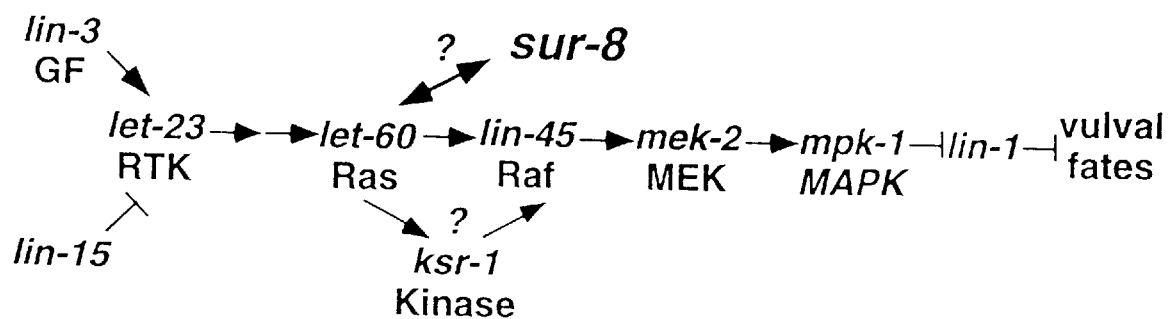
FIG. 2 shows a schematic of the key genes involved in the main signal transduction pathway of vulval cell fate in *C. elegans*.

The signal from the neighboring gonad induces three VPCs to adopt vulval cell fates (Sundaram and Han, BioEssays 18, 473 [1996]; and Kornfeld [1997], supra). The key genes involved in the main signal transduction pathway are shown in FIG. 2. Components in this pathway were primarily identified by genetics (Sundaram and Han [1996], supra; and Kornfeld [1997], supra). ksr-1 is a novel kinase that acts to positively regulate the Ras pathway (Sundaram and Han [1995], supra; and Kornfeld et al. [1995], supra). sur-8 also functions to positively regulate the Ras pathway and may either define a branch point that feeds directly out of let-60 ras or be involved with the establishment or maintenance of let-60 ras activation (GF=growth factor; RTK=receptor tyrosine kinase). Mutations that reduce signaling activity cause less than three VPCs to adopt a vulval cell fate (Vulvaless, or Vul). Mutations that cause constitutive activation of the pathway (e.g., activated ras mutations) cause up to all six VPCs to adopt vulval cell fates (Multivulva or Muv). Many genes in the pathway function in multiple cell signaling events during *C. elegans* development. For example, besides vulval induction, let-60 ras has been shown to function in male tail fate specification (Chamberlin and Sternberg, Development 120, 2713 [1994]), germ cell and oocyte development (Church et al., Development 121, 2525 [1995]; and Gutch et al., Genes Dev. 12, 571 [1998]), sex-myoblast migration (Sundaram et al., Development 122, 2823 [1996]), and excretory duct cell fate specification (Yochem et al., Mol. Cell Biol. 17, 2716 [1997]).

To identify new factors acting downstream of let-60 ras, the present invention provides methods for screening mutations that suppress activated let-60 ras mutations. In addition to genes acting in the main pathway downstream of let-60 ras, the methods of the present invention have identified mutations in a number of new genes that can suppress the Muv phenotype caused by activated let-60 ras, but that do not cause an obvious vulval phenotype on their own.

I. sur-8 in *C. elegans* Vulval Development

A. Mutations in sur-8 Suppress Activated let-60 ras

To identify regulators that act downstream of Ras during vulval induction, methods of the present invention screened for extragenic suppressor mutations that would revert the Multivulva (Muv) phenotype caused by a gain-of-function let-60 ras mutation, n1046gf, back to wild type. The n1046gf mutation causes a Gly to Glu substitution at codon 13 (G13E) and is similar to the Gly to Val codon 12 substitution found in human Ras oncoproteins (Beitel et al., Nature 348, 503 [1990]). By screening for suppressors of this activated ras mutation, it is possible to identify mutations in genes acting downstream of, or in parallel to, let-60 ras or in genes involved in the proper expression or activation of let-60 ras. The parental strain used for screening carries multiple copies of a let-60 ras(n1046gf) genomic fragment (Sundaram et al. [1996], supra) and displays a completely penetrant Muv phenotype. This increased penetrance of Muv phenotype over that caused by non-transgenic let-60 ras(n1046gf) animals allowed rapid screening of a large number of genomes for suppressors. Of 22,000 haploid genomes screened, 11 mutations were isolated in at least four genes, including a single mutation in the sur-8 locus (suppressor of ras), ku167, three alleles of lin-45 raf and 3 alleles of mek-2. A second allele of sur-8, ku242, was isolated in a non-complementation screen that was not biased against isolating null mutations. sur-8(ku242) failed to complement the suppression phenotype of sur-8(ku167) in a let-60 ras (n1046gf) background.

Both sur-8(ku167) and sur-8(ku242) mutations suppressed the Muv phenotype caused by let-60 ras (n1046gf) to nearly wild type and suppressed the male mating defect associated with let-60 ras(n1046gf). For example, the sur-8

(ku167) mutation reduced the Muv phenotype of let-60 (n1046gf) animals from 87% to 4% as shown in Table 1 below.

TABLE 1

Phenotype and Gene Dosage Analysis of sur-8 Mutant Animals

| # | genotype[a] sur-8 | let-60 ras | | phenotype % MUV(n)[b] | % induction (n)[c] |
|---|---|---|---|---|---|
| 1 | + | + | | 0 (many) | 100 (many) |
| 2 | + | gf | | 87 (276) | 154 (27) |
| 3 | ku167/ku167 | gf | | 4 (333) | 102 (43) |
| 4 | ku167/+ | gf | | 77 (57) | 129 (16) |
| 5 | ku242/ku242 | gf | | 7 (328) | 103 (33) |
| 6 | ku242/+ | gf | | 84 (175) | 153 (15) |
| 7 | ku167/ku242 | gf | | 11 (160) | 103 (31) |
| 8 | ku167/ku167 | gf; | mDp1 | 90 (200) | 154 (32) |
| 9 | + | gf; | mDp1 | 100 (247) | 182 (30) |
| 10 | ku167/mDf4[d] | gf | | 14 (270) | 108 (32) |
| 11 | +/mDf4[d] | gf | | 68 (233) | 136 (22) |

[a]The complete genotypes for each strain are: 1, N2 (wildtype); 2, let-60 (n1046); 3, sur-8(ku167) let-60(n1046); 4, sur-8(ku167) unc-24 let-60 (n1046)/+ let-60(sy130) dpy-20 (sy130 encodes the same G13E substitution as (n1046) 5, sur-8(ku242) let-60(n1046); 6, sur-8(ku242) unc-24 let-60(n1046)/let-60(sy130) dpy-20; 7, sur-8(ku167) let-60(n1046)/sur-8 (ku242)unc-24 let-60(n1046); 8, sur-8(ku167) unc-5 let-60(n1046); mDp1; 9, unc-5 let-60(n1046); mDp1; 10, unc-5 sur-8(ku167) let-60(n1046)/dpy-13 mDf4 let-60(n1046); 11, let-60(n1046)/let-60(n1046) dpy-13 mDf4.
[b]Percent Multivulva was determined by scoring adult hermaphrodites for presence of ventral protrusions under a dissecting microscope. "n" indicates the number of animals scored.
[c]Average percentage of VPCs adopting a vulval cell fate per animal. In wild type (100% induction), three of six VPCs are induced.
[d]The dpy-13 marker is semi-dominant and, when heterozygous, reduces the ability of sur-8(ku167) to suppress let-60(n1046). For comparison, dpy-13 sur-8(ku167) let-60(n1046)/sur-8(ku167) unc-5 let-60(n1046) animals were 22% (239) Muv and had 117% (26) average induction.

The suppression observed was due to a decrease in the average vulval induction of the VPCs from 154% to 102%. Both sur-8 mutations most often reverted the pattern of ectopic vulval induction back to a wild type pattern as shown in Table 2 below, showing genetic interactions between sur-8 and ksr-1 or mpk-1 MAPK mutations. However, since sur-8(ku167) was a slightly stronger suppressor than sur-8 (ku242), further genetic characterization was performed using sur-8(ku167).

TABLE 2

Genetic Interactions Between sur-8 and ksr-1 or mpk-1 MAPK Mutations

| genotype | % induction[a] | | | | | | average induction (n) | lethal[b] (n) |
|---|---|---|---|---|---|---|---|---|
| | P3.p | P4.p | P5.p | P6.p | P7.p | P8.p | | |
| N2 (wild type) | 0 | 0 | 100 | 100 | 100 | 0 | 100% (many) | 0 (138) |
| sur-8 (ku167) | 0 | 0 | 100 | 100 | 100 | 0 | 100% (28) | 0 (244) |
| sur-8 (ku242) | 0 | 0 | 100 | 100 | 100 | 0 | 100% (26) | 0 (347)[e] |
| mpk-1 (ku1)[c] | 0 | 0 | 100 | 94 | 100 | 0 | 98% (17) | 7 (229) |
| mpk-1 (ku1); sur-8 (ku167)[c] | 0 | 0 | 0 | 0 | 0 | 0 | 0% (25) | 100 (80) |
| ksr-1 (ku68)[d] | 0 | 0 | 100 | 100 | 100 | 0 | 100% (15) | 24 (257) |
| sur-8 (ku167); ksr-1 (ku68)[d] | 0 | 0 | 0 | 11 | 0 | 0 | 4% (19) | 85 (164) |

[a]Individual VPCs adopting 1° or 2° fates were scored as induced.
[b]Percent of animals arresting with an early larval rod-like phenotype, characteristic of loss-of-function mutations in many ras pathway genes.
[c]sur-8 was marked with unc-24. Unc self progeny of ku1; ku167 unc-24/++ mothers died as early larval rods. Unc escapers were scored for vulval induction. Double homozygotes were almost completely sterile (average brood = 4), and all progeny died as early larval rods.
[d]ksr-1 was marked with lon-2.
[e]Two animals had abnormal vulval morphology.

Genetic dosage analysis indicated that the sur-8(ku167) mutation is a recessive, strong loss-of-function mutation. The deficiency mDf4 failed to complement sur-8(ku167) for the suppression phenotype. Animals in which ku167 was in trans to mDf4, and thus contained only one copy of sur-8 (ku167), displayed a suppression phenotype that was similar to, but slightly stronger than, animals homozygous for sur-8(ku167) as shown in Table 1. Thus, the sur-8(ku167) mutation results in reduction but possibly not elimination of sur-8(+) function. The duplication mDp1, which covers the sur-8 locus, reverted the suppression phenotype of sur-8 (ku167) let-60(n1046gf) animals to 90% Muv (Table 1). In addition, introducing an extra copy of sur-8 with mDp1 enhanced the Multivulva phenotype of let-60 ras(n1046gf) to 100% Muv (Table 1). Thus, additional copies of sur-8(+) caused a gain-of-function phenotype indicating that the vulval induction pathway is sensitive to increasing sur-8 doses, although an understanding of this mechanism is not necessary to practice the present invention.

B. sur-8 Positively Regulates Ras Pathway Signaling

Although sur-8(ku167) and sur-8(ku242) suppressed the Muv phenotype caused by the activated let-60 ras(n1046gf) mutation, neither allele caused an apparent phenotype in a let-60 ras(+) background. Mutants displayed wild type vulval induction (Table 2) and appeared to have no additional defects. Specifically, there was no embryonic lethality observed, rod-like larval lethality (i.e., which is often associated with loss-of-function mutations in other Ras pathway components), and no changes in fertility in sur-8 mutants. Since sur-8 mutations are likely to be strong loss-of-function, the lack of vulval phenotype observed in mutants most likely reflects a non-essential role for sur-8 when Ras pathway components are wild type, although understanding the mechanism is not necessary to practice the present invention.

While sur-8 mutations did not affect vulval induction in an otherwise wild type background, sur-8 (ku167) dramatically affected signaling when other ras pathway components were compromised. sur-8(ku167) dramatically enhanced vulval and larval lethal phenotypes caused by a weak loss-of-function mutation in mpk-1(ku1) (Wu and Han, Genes Dev. 8, 147 [1994]) (Table 2). mpk-1(ku1) mutants alone display nearly wild type vulval induction and only 7% rod-like larval lethality, but sur-8(ku167) decreased vulval induction to 0% and increased larval lethality to nearly 100% in the double mutants. Because mpk-1 MAP kinase is a component of the main Ras pathway, this observed genetic interaction suggests that sur-8 is an important positive regulator of the Ras pathway that functions to increase pathway output.

sur-8(ku167) also showed strong genetic interactions with a loss-of-function mutation in another regulator of the Ras pathway, ksr-1(ku68) (Sundaram, 1995, supra) (Table 2). ksr-1(ku68) mutants alone display wild type vulval induction (100%) and a weak rod-like lethal phenotype (24%). In sur-8(ku167); ksr-1 (ku68) double mutants, vulval induction was reduced to 4% and the rod-like larval lethality was increased to 85%. This strong genetic interaction between sur-8 and ksr-1 suggests that while the function of neither gene is normally required for ras signaling, their functions are collectively essential for ras signaling, although an understanding of this mechanisms is not required to practice the present invention and the present invention is not limited to this interpretation.

C. sur-8 Functions Downstream or in Parallel of ras and not Downstream of raf

To determine at which step in the linear Ras pathway sur-8 may function, epistatic analysis was performed with mutations that cause Muv phenotypes. sur-8 mutations almost completely suppressed the Muv phenotype caused by let-60 ras(n1046gf), suggesting that sur-8 acts downstream of, or in parallel to, let-60 ras as shown in Table 3.

TABLE 3

Epistatic Analysis of sur-8(ku167) and Multivulva Mutants

| genotype | | % Muv (n) | % Induction (n) |
|---|---|---|---|
| +; | let-60(n1046gf) | 88 (240) | 154 (27) |
| sur-8(ku167); | let-60(h1046gf) | 4 (333) | 102 (43) |
| +; | HSP-raf (gf) | nd | 116 (31) |
| sur-8(ku167); | HSP-raf (gf) | nd | 125 (28) |
| mek-2(ku114); | HSP-raf (gf) | nd | 97 (25) |
| mpk-1(ku1); | HSP-raf (gf) | nd | 99 (28) |
| +; | lin-15 (n765) | 98 (214) | 190 (24) |
| sur-8(ku167); | lin-15 (n765) | 73 (302) | 142 (21) |
| sur-8(ku242); | lin-15 (n765) | 58 (258) | 133 (23) |
| lin-1(ar147); | + | 100 (154) | nd |
| lin-1(ar147); | sur-8(ku167) | 100 (184) | nd |

For HSP-raf(gf) experiments, transgenic animals were heat shocked for 80 minutes at 37° C. at early L3. For lin-15 experiments, animals were grown at 19.2° C.
nd = not determined.

Tests were performed to determine whether sur-8 mutations could suppress the Muv phenotype caused by a loss-of-function mutation in lin-15, n765. lin-15 functions upstream of ras at the level of let-23 RTK to inhibit let-23 signaling (Ferguson et al., Nature 326, 259 [1987]) and encodes two novel proteins that are thought to be secreted by the surrounding hypodermis (Clark et al., Genetics 137, 987, [1994]; and Huang et al., Mol. Biol. Cell 5, 395 [1994]). As expected, sur-8 mutations could suppress the lin-15 mutant Muv phenotype (Table 3), consistent with sur-8 functioning downstream of let-60 ras. However, this suppression is not complete, possibly due to the inability of sur-8 mutations to overcome excessively strong pathway activity caused by the lin-15(n765) mutation.

In order to define a downstream limit for sur-8 function, tests were performed to determine whether a sur-8 mutation could suppress the Muv phenotype caused by genes acting downstream of ras in the pathway. lin-1 is a negative regulator of the ras pathway encoding a putative transcription factor that by genetic criteria acts downstream of mpk-1 MAP kinase (Beitel et al., Genes Dev. 9, 3149 [1995]; Wu, 1994, supra; and Kornfeld et al., Genes Dev. 9, 756 [1995]). A loss-of-function mutation of lin-1, ar147, caused a 100% Muv phenotype that was not suppressed by sur-8(ku167).

Double mutants displayed the same 100% Muv phenotype as the lin-1 mutants (Table 3), suggesting that sur-8 does not act downstream and probably acts upstream of lin-1.

Genetic studies indicate that lin-45 raf acts downstream of let-60 ras in the vulval induction pathway (Han et al., Nature 363, 133 [1993]). Animals carrying an activated raf(gf) transgene driven by a heat shock promoter displayed a Muv phenotype upon heat shock (Table 3). As expected, the Muv phenotype was completely suppressed by weak mutations in either mek-2 or mpk-1 (Table 3), which act downstream of lin-45 raf (Sundaram, 1996, supra; and Kornfeld, 1997, supra). However, a sur-8 mutation failed to suppress the Muv phenotype caused by the raf(gf) transgene. Heat shocked raf(gf) mutants or sur-8(ku167); raf(gf) double mutants displayed similar average vulval induction of 116% and 125%, respectively (Table 3). This data suggests that sur-8 does not function downstream of lin-45 raf in the same linear pathway as mek-2 and mpk-1, but instead acts upstream or in a parallel pathway.

Although an understanding of the mechanism is not necessary to practice the present invention and the present invention is not limited to such mechanistic explanations, taken together, the epistatic data indicate that sur-8 acts downstream or in parallel to let-60 ras but not downstream of lin-45 raf Since by analogy with their mammalian homologues (Moodie et al., Science 260, 1658 [1993]), let-60 ras and lin-45 raf are likely to directly interact, it is unlikely that sur-8 is acting directly between them. Instead, it appears that sur-8 functions in a branch point either leading into or out of the pathway at the level of lin-45 raf or let-60 ras.

D. sur-8 Function is Required during Vulval Induction

Vulval cell fate specification takes place at the end of the L2 stage, after the anchor cell is born and before the VPCs undergo their first division (Kimble, Dev. Biol. 87, 286 [1981]). To determine if sur-8(+) activity is required at this stage for proper vulval induction, the ability of sur-8(+) to rescue the suppression phenotype of sur-8(ku167) let-60 (n1046gf) animals at various stages of development was assayed. Transgenic sur-8(ku167) let-60(n1046gf) animals were generated, carrying sur-8 cDNA under the control of a heat inducible promoter and induced sur-8(+) expression by heat shocking at different developmental stages. Control transgenic animals without heat shock displayed a Suppressed phenotype and 111% vulval induction that was similar to that of sur-8(ku167) let-60(n1046gf). Animals heat shocked before or during vulval induction (between early L2 and early L3 stages) displayed a fully rescued phenotype resulting in over 160% induction. This level of rescuing activity was also observed in sur-8(ku167) let-60 (n1046gf) mutants carrying a transgene of sur-8 under control of its own promoter. In contrast, animals heat shocked either in L1, before the anchor cell is born, or in L4, after Pn.p cells have executed their fate, displayed a non-rescued phenotype of 133% or 134% vulval induction as shown in Table 4, below.

TABLE 4

Functional Tests of Human or C. elegans sur-8 cDNA under Control of a Heat Shock Inducible Promoter

| trans-gene[a] | stage | induction % | | | | | | total induction | n |
|---|---|---|---|---|---|---|---|---|---|
| | | P3.p | P4.p | P5.p | P6.p | P7.p | P8.p | | |
| vector | eL3 | 0 | 8 | 100 | 100 | 100 | 6 | 103% | 38 |
| Ce sur-8 | eL3 | 61 | 97 | 100 | 100 | 100 | 93 | 184% | 42 |

TABLE 4-continued

Functional Tests of Human or C. elegans sur-8 cDNA under Control of a Heat Shock Inducible Promoter

| trans-gene[a] | stage | induction % | | | | | | total induction | n |
|---|---|---|---|---|---|---|---|---|---|
| | | P3.p | P4.p | P5.p | P6.p | P7.p | P8.p | | |
| Hs sur-8 | eL3 | 16 | 40 | 100 | 100 | 100 | 70 | 142% | 25 |
| Ce sur-8 | L1 | 10 | 55 | 100 | 100 | 100 | 26 | 133% | 19 |
| Ce sur-8 | eL2 | 28 | 81 | 100 | 100 | 100 | 76 | 162% | 21 |
| Ce sur-8 | mL3 | 33 | 83 | 100 | 100 | 100 | 89 | 169% | 19 |
| Ce sur-8 | eL4 | 3 | 24 | 100 | 100 | 100 | 28 | 134% | 29 | sur-8(ku167) let-60(n1046) hermaphrodites carrying the indicated transgene were heat shocked at the indicated stage (e = early, m = mid) at 37° C. and scored for vulval induction at stage L4 or as young adults. Heat shock was for 80 minutes for the upper set of experiments and 40 minutes for the lower set of experiments.
[a]Extrachromosomal arrays carried either full length Ce sur-8 coding region or Hs sur-8 coding region under the control of a heat shock inducible HSP-16 promoter.

Although the present invention is not limited to any specific mechanism, the rescuing activity observed in early L2 heat-shocked animals is most likely due to SUR-8 protein perdurance. Thus, sur-8(+) activity is required before or during the time of vulval cell fate specification for vulval development but is not required at earlier or later times.

II. Cloning and Characterization of C. elegans and Mammalian sur-8

A. sur-8 Encodes a Novel Leucine-Rich Repeat Protein

C. elegans sur-8 was cloned by genetic mapping followed by transformation rescue as described in Example 7. sur-8 was mapped to position 1.86 on chromosome IV between the markers dpy-13 and unc-5. Cosmids containing genomic DNA from this region were tested for sur-8(+) activity by assaying their ability to revert the Suppressed phenotype of sur-8(ku167) let-60(n1046gf) animals back to Muv. A single cosmid, AC7 contained complete rescuing activity as did a 12 kb subclone derived from AC7. The subclone was predicted to contain a single gene, designated AC7.1 by the C. elegans genome sequencing project. A full length 2.1 kb cDNA was identified by screening a mixed stage library using a genomic probe derived from the predicted AC7.1 gene. Northern blot analysis indicated that this cDNA was the only gene product encoded by sur-8. This suggested that the gene defined by the isolated cDNA corresponds to sur-8 because missense mutations from sur-8 mutant DNA are located in the coding region of the cDNA, and this cDNA was able to rescue sur-8 mutants.

The 1.7 kb open reading frame of sur-8 was predicted by computer analysis to encode a novel 559 amino acid protein containing 18 tandem repeats of the leucine-rich repeat (LRR) motif (amino acids 116–532). LRRs are characterized by a consensus predominantly composed of leucines at invariant positions. LRRs are found in a variety of proteins with diverse biological functions and are proposed to mediate protein-protein interactions (Kobe et al., Trends Biochem. Sci. 19, 415 [1994]). Fifteen of the eighteen SUR-8 LRRs are 23 amino acids long and form a consensus that is similar to that of yeast adenylate cyclase LRRs as shown in FIG. 3. Here, consensus amino acids are boxed and shown below with the consensus of C. elegans SUR-8 LRR and yeast adenylate cyclase (yeast A.C.; α=aliphatic residue A, V, L, I, F, Y, or M).

Yeast adenylate cyclase LRRs are required for binding to and activation by Ras (Suzuki et al., Proc. Natl. Acad. Sci. 87, 8711 [1990]; and Field et al., Science 247, 464 [1990]). These 23 amino acid LRRs form two tandem clusters of 9 and 6 repeats that are separated by three tandem LRRs that are 24 amino acids long and form a distinct consensus with no obvious similarity to other known LRR motifs. SUR-8 contains N-terminal and C-terminal non-LRR flanking sequences of 115 and 26 amino acids, respectively.

Additionally, missense mutations associated with each sur-8 allele were found. sur-8(ku242) contains a cysteine 233 to tyrosine substitution in a consensus position of LRR 7. sur-8(ku167) contains a glutamic acid 430 to lysine substitution in a non-consensus position of LRR 12. Both mutations were found to alter highly conserved amino acids indicating that these residues and LRRs are important for sur-8(+) function.

B. C. elegans sur-8 is Structurally and Functionally Conserved in Mammals

An expressed sequence tag (EST) database search revealed several overlapping human and mouse ESTs that shared from 49% to 70% amino acid identity with C-terminal sequences of C. elegans SUR-8. Primers derived from one of the human or mouse ESTs were used (GenBank accession numbers W51818 and AA286839, respectively) to amplify the 5' ends of the cDNAs by performing 5' RACE from human brain cDNA or mouse liver cDNA (Clonetech). Sequences from the 5' RACE and EST clones were compiled to generate the full-length human and mouse 4.1 kb sur-8 cDNAs. Multi-tissue Northern blot (Clonetech) analysis using a probe derived from the human cDNA revealed that this cDNA corresponded to a single transcript of the expected size, and the transcript was detected in all tissues examined, including heart, brain, placenta, lung, liver, skeletal muscle, kidney, and pancreas. The predicted proteins encoded by the human and mouse cDNAs are 98% identical at the amino acid level.

Figure 5:
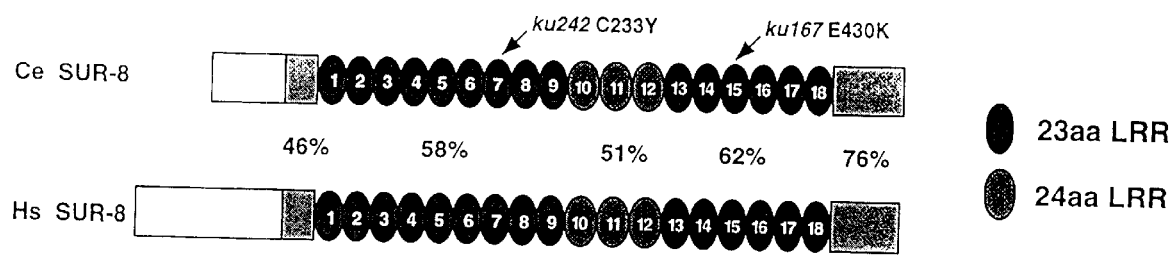
FIG. 5 shows a comparison of *C. elegans* and human SUR-8 protein structure. The positions of the leucine-rich repeats and the amino acid substitutions of sur-8 mutants are shown.

Comparison of the amino acid sequences encoded by the mammalian and C. elegans sur-8 genes revealed significant homology in the overall protein structure and amino acid sequence. Mammalian SUR-8 contains exactly the same number of LRRs with the identical length and identical consensus sequence as C. elegans SUR-8 LRRs. In FIG. 4, complete amino acid alignment of predicted SUR-8 protein sequences from human (Hs SUR-8), mouse (Mu SUR-8), and C. elegans (Ce SUR-8) are shown. Residue identity between species is highlighted in black and similarity is highlighted in gray. The positions of the leucine-rich repeats (LRRs) are indicated with dark bars (for 23 amino acid repeats) or light bars (for 24 amino acid repeats). The position of the amino acid substitutions are indicated for the two sur-8 mutations. FIG. 5 shows a comparison of C. elegans and human SUR-8 protein structure. The positions of the leucine-rich repeats and the amino acid substitutions of sur-8 mutants are shown. Percent amino acid identity between C. elegans and human SUR-8 is indicated for the domains shown. The N-terminal 93 amino acids of human SUR-8 shares no sequence homology with C. elegans SUR-8.

In addition to sharing a high degree of structural homology, the C. elegans and human SUR-8 proteins share functional homology. Human sur-8 cDNA expressed under the control of a heat shock inducible promoter was able to rescue the mutant phenotype of sur-8(ku167) let-60 (n1046gf) animals (Table 4). Human sur-8 could revert the suppressed phenotype from 103% induction to 142% induction. Fully rescued control animals expressing C. elegans sur-8 cDNA displayed 184% induction (Table 4). Because human sur-8 could provide sur-8(+) activity in sur-8 mutants, human sur-8 appears to be a functional homologue of *C. elegans* sur-8.

Similar methods to those discussed above or other methods known in the art can be used to identify sur-8 genes from other species based on the information provided by the present invention. Because of the high degree of sequence similarity in species as diverse as *C. elegans* and humans and between different mammalian species, the sequences provided by the present invention can be used to screen for sur-8 genes in other species where sequence information is available. Prior to the present invention, such methods were not possible, as the existence of and sequence of sur-8 was not known.

III. Interaction of SUR-8 with Ras

A. SUR-8 Interacts with LET-60 Ras, but not with a LET-60 Ras Effector Domain Mutant The observation that SUR-8 LRRs are similar to those found in yeast adenylate cyclase suggested that SUR-8 may bind LET-60 Ras. A yeast two-hybrid system was used to test the interaction between SUR-8 and several ras pathway components as described in Example 9. While the test failed to detect an interaction between SUR-8 and wild type LIN-45 Raf, MEK-2 MEK, MPK-1 MAP kinase, or KSR-1, it detected a strong interaction with wild type LET-60 Ras, as assayed by the activation of His reporter and a LacZ reporter.

Figure 6:
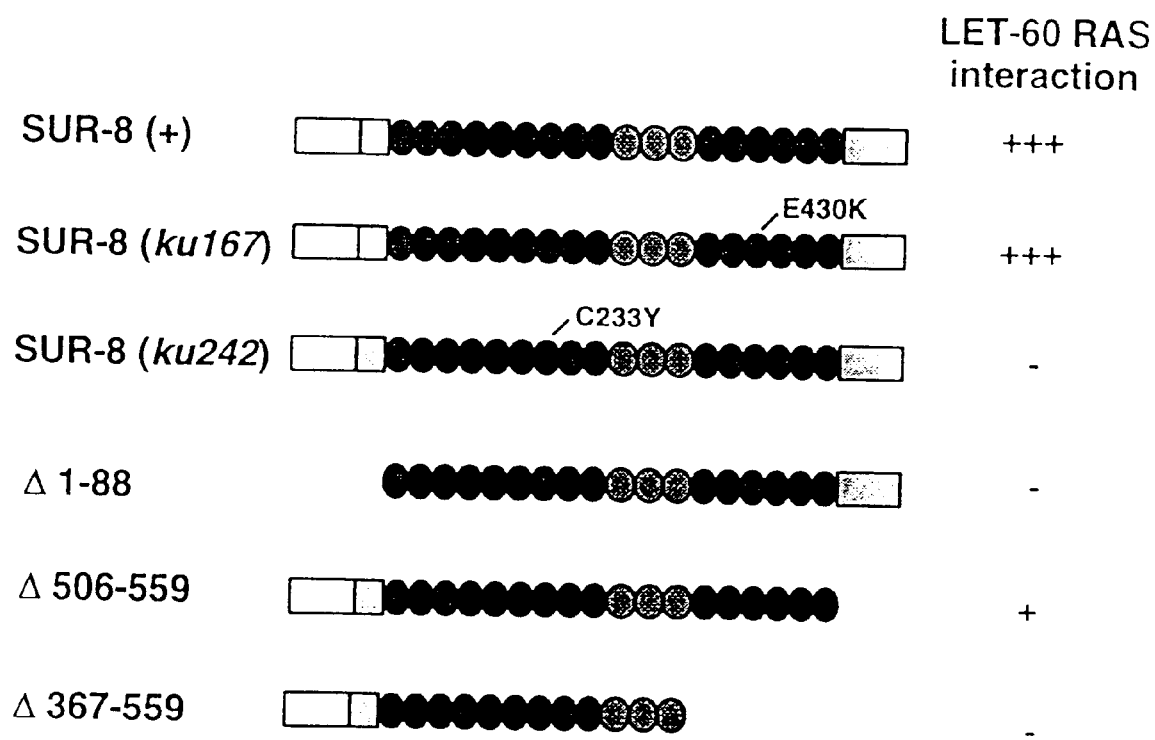
FIG. 6 shows a schematic of the level of interaction between LET-60 Ras and wild-type SUR-8 and various SUR-8 mutants and fragments.

Given that mutations in the LRR regions result in loss of sur-8 function, the effect of these mutations on LET-60 Ras interaction were examined. Interestingly, ku167 E430K had no effect on LET-60 Ras interaction, but ku242 C233Y completely eliminated detectable interaction with LET-60 Ras as shown in FIG. 6, even though both mutant proteins were expressed at similar levels in yeast. The ku242 C233Y mutation is in LRR 7 of the N-terminal LRR cluster and this data demonstrated that this residue is critical for SUR-8 function as well as LET-60 Ras binding.

To define a specific region of SUR-8 involved in LET-60 Ras binding, SUR-8 deletion mutants were tested for LET-60 Ras interaction. Deletion of the N-terminal 88 amino acid non-LRR region resulted in elimination of LET-60 Ras binding. Similarly, deletion of the C-terminal 53 amino acid non-LRR sequence resulted in reduction of LET-60 Ras binding seen in FIG. 6. In addition, deletion of the last six LRRs, including repeat 15, abolished LET-60 Ras binding. It is likely that N-or C-terminal deletions alter global protein structure resulting in decreased LET-60 Ras interaction, although an understanding of the mechanism in not required to practice the present invention.

Figure 7:
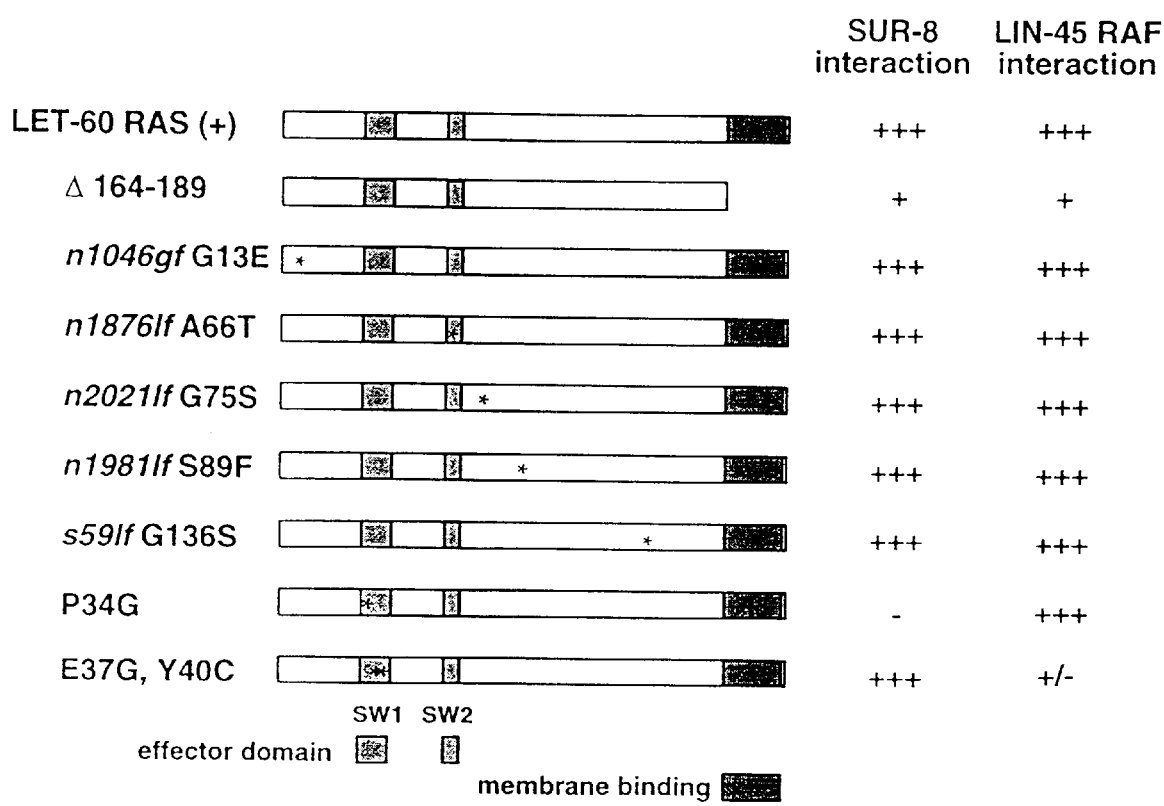
FIG. 7 shows a schematic of the level of interaction between SUR-8 and LIN-45 RAF with various LET-60 Ras mutations.

To define a domain of LET-60 Ras required for SUR-8 interaction, the interaction of SUR-8(+) with several different LET-60 Ras mutants was tested using the yeast two-hybrid system. As a control for LET-60 Ras expression, the interaction of LET-60 Ras mutants with LIN-45 Raf was tested. Mutations tested included point mutations that cause phenotypes in *C. elegans* (Beitel, 1990, supra), deletion mutations, and effector domain mutations as shown in FIG. 7. Point mutations in the effector domain of H-Ras have been shown to abolish binding to several putative Ras binding proteins, including Raf1, PI-3 kinase, and Ral-GDS (Rodriguez-Viciana et al., Cell 89, 457 [1997]).

All of the LET-60 Ras mutations tested that cause loss-of-function phenotypes had no effect on SUR-8 or LIN-45 Raf binding. In addition, the mutation encoded by the gain-of-function allele, n1046gf 13E, had no effect on SUR-8 binding or LIN-45 Raf binding. Deletion of the membrane targeting region had only a slight effect on SUR-8 binding or LIN-45 Raf binding. However, one effector domain mutation was identified, P34G, that specifically interfered with SUR-8(+) binding but had no effect on LIN-45 Raf binding. Conversely, an effector domain double mutation, G37 C40, interfered with LIN-45 Raf binding, but had no effect on SUR-8 binding (FIG. 7). Thus, the present invention identifies an amino acid residue in the putative effector domain of LET-60 Ras required for SUR-8 binding but not LIN-45 Raf binding.

B. Hs SUR-8 Interacts with N-Ras and K-Ras 4B but not H-Ras in Vitro

Given the functional and structural homology between *C. elegans* sur-8 and human sur-8, studies were undertaken to determine whether human SUR-8 could bind mammalian Ras. The interaction of human SUR-8 with three Ras family members, N-Ras, K-Ras 4B, and H-Ras was tested in the yeast two-hybrid system. Ras family members fused to the GAL4 DNA binding domain were expressed together with SUR-8 proteins fused to the GAL4 activation domain in a yeast reporter strain and assayed for interaction by growth on His-selective media. The test detected a strong interaction between human SUR-8 and two family members, K-Ras and N-Ras but detected only a weak interaction with H-Ras as shown in FIG. 8. As a control for Ras expression, it was shown that all three Ras family members interacted strongly with Raf1 (FIG. 8). In addition SUR-8 and Ras displayed cross-species interactions, reinforcing the idea that they are functionally homologous.

These observations were confirmed by testing in vitro interaction of Human SUR-8 and Ras family members. Bacterially expressed GST-Ras fusion proteins were purified and tested for their ability to interact with purified His tagged Hs SUR-8 or Raf1. While all three family members bound Raf1 with similar affinity, only N-Ras and K-Ras were capable of binding human SUR-8 strongly as shown in FIG. 8. In FIG. 8, GST-Ras fusion proteins were loaded with GDP(D) or GTP(T) and incubated with either full length human SUR-8 or Raf1 (residues 1 to 269). Bound Hs SUR-8 or Raf1 was subjected to SDS-PAGE and Western immunoblotting with an anti 5x-His monoclonal antibody. As a control for amount of Ras in the binding assays, one eighth of the amount of Ras input in the binding reactions is shown in the lowest panel. While Raf1 bound Ras with GTP dependence, human SUR-8 showed no GTP dependence for Ras binding. Both GDP and GTP loaded N-Ras or K-Ras bound Hs SUR-8 with similar affinities (FIG. 8). Thus, SUR-8 displayed a differential binding specificity for individual Ras family members, and binding appeared not to depend on the activation state of Ras.

IV. Generation of SUR-8 Antibodies

Antibodies can be generated to allow for the detection of SUR-8 protein. The antibodies may be prepared using various immunogens. In one embodiment, the immunogen is a human SUR-8 peptide (e.g., an amino acid sequence as depicted in SEQ ID NO:8, or fragments thereof) to generate antibodies that recognize human SUR-8. Such antibodies include, but are not limited to polyclonal, monoclonal, chimeric, single chain, Fab fragments, and an Fab expression library.

Various procedures known in the art may be used for the production of polyclonal antibodies to SUR-8. For the production of antibody, various host animals can be immunized by injection with the peptide corresponding to the SUR-8 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies directed toward SUR-8, any technique that provides for the production of antibody molecules by continuous cell lines in culture may be used (See, e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495–497 [1975]), as well as the trioma technique, the human B-cell hybridoma technique (See e.g., Kozbor et al. Immunol. Today 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

In an additional embodiment of the invention, monoclonal antibodies can be produced in germ-free animals utilizing recent technology. According to the invention, human antibodies may be used and can be obtained by using human hybridomas (Cote et al., Proc. Natl. Acad. Sci. U.S.A.80:2026–2030 [1983]) or by transforming human B cells with EBV virus in vitro (Cole et al., in *Monoclonal Antibodies and Cancer Therapy*, Alan R. Liss, pp. 77–96 [1985]).

According to the invention, techniques described for the production of single chain antibodies (U.S. Pat. No. 4,946,778; herein incorporated by reference) can be adapted to produce SUR-8-specific single chain antibodies. An additional embodiment of the invention utilizes the techniques described for the construction of Fab expression libraries (Huse et al., Science 246:1275–1281 [1989]) to allow rapid and easy identification of monoclonal Fab fragments with the desired specificity for SUR-8.

Antibody fragments that contain the idiotype (antigen binding region) of the antibody molecule can be generated by known techniques. For example, such fragments include but are not limited to: the F(ab')2 fragment that can be produced by pepsin digestion of the antibody molecule; the Fab' fragments that can be generated by reducing the disulfide bridges of the F(ab')2 fragment, and the Fab fragments that can be generated by treating the antibody molecule with papain and a reducing agent.

In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. (As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of SUR-8 (e.g., for Western blotting), measuring levels thereof in appropriate biological samples, etc. The antibodies can be used to detect SUR-8 in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human SUR-8 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of SUR-8 detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter Ras signal transduction. Specific antibodies that bind to the binding domains of SUR-8 or other proteins involved in Ras signalling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of Ras. Such antibodies can also be used diagnostically to measure abnormal expression of SUR-8, or the aberrant formation of the protein complexes, which may be indicative of a disease state.

V. Gene Therapy Using sur-8

The present invention also provides methods and compositions suitable for gene therapy to alter SUR-8 expression, production, or function. As described above, the present invention provides human, mouse, and *C. elegans* sur-8 genes and provides methods of obtaining sur-8 genes from other species. Thus, the methods described below are generally applicable across many species.

Viral vectors commonly used for in vivo or ex vivo targeting and therapy procedures are DNA-based vectors and retroviral vectors. Methods for constructing and using viral vectors are known in the art (See, e.g., Miller and Rosman, BioTechniques 7:980–990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA virus, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320–330 [1991]), defective herpes virus vector lacking a glycoprotein L gene (See e.g., Patent Publication RD 37105 A), or other defective herpes virus vectors (See e.g., International Patent Publication No. WO 94/21807; and International Patent Publication No. WO 92/05263); an attenuated adenovirus vector, such as the vector described by Stratford-Perricaudet et al. (J. Clin. Invest., 90:626–630 [1992]; See also, La Salle et al., Science 259:988–990 [1993]); and a defective adeno-associated virus vector (Samulski et al., J. Virol., 61:3096–3101 [1987]; Samulski et al., J. Virol. 63:3822–3828 [1989]; and Lebkowski et al., Mol. Cell. Biol., 8:3988–3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma(IFN-$\gamma$), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See, WO94/26914). Those adenoviruses of animal origin that can be used within the scope of the present invention include adenoviruses of canine, bovine, murine (e.g., Mav1, Beard et al., Virol, 175:81–90 [1990], ovine, porcine, avian, and simian (e.g, SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO95/02697), the E2 region (e.g., WO94/28938), the E4 region (e.g., WO94/28152, WO94/12649 and WO95/02697), or in any of the late genes L1–L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO95/02697 and WO96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid which carries, inter alia, the DNA sequence of interest. The homologous recombination is effected following co-transfection of the adenovirus and plasmid into an appropriate cell line. The cell line that is employed should preferably (i) be transformable by the elements, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO94/26914 and WO95/02697. Recombinant adenoviruses are recovered and purified using standard molecular biological techniques, that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368, herein incorporated by reference; U.S. Pat. No. 5,139,941, herein incorporated by reference; and EP 488 528). These publications describe various AAV-derived constructs in which the rep and/or cap genes are deleted and replaced by a gene of interest, and the use of these constructs for transferring the gene of interest in vitro (into cultured cells) or in vivo, (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment the gene can be introduced in a retroviral vector (e.g., as described in U.S. Pat. Nos. 5,399, 346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; International Patent Publication No. WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are disclosed in WO95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference); the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., Proc. Natl. Acad. Sci. U.S.A., 84:7413–7417 [1987]; See also, Macky, et al., Proc. Natl. Acad. Sci. U.S.A., 85:8027–8031 [1988]; Ulmer et al., Science 259:1745–1748 [1993]). The use of cationic lipids may promote encapsulation of negatively charged nucleic acids, and also promote fusion with negatively charged cell membranes (Felgner and Ringold, Science 337:387–388 [1989]). Particularly useful lipid compounds and compositions for transfer of nucleic acids are described in International Patent Publications WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wilson et al., J. Biol. Chem., 267:963–967 [1992]; Wu and Wu, J. Biol. Chem., 263:14621–14624 [1988]; and Williams et al., Proc. Natl. Acad. Sci. U.S.A., 88:2726–2730 [1991]). Receptor-mediated DNA delivery approaches can also be used (Curiel et al., Hum. Gene Ther., 3:147–154 [1992]; and Wu and Wu, J. Biol. Chem., 262:4429–4432 [1987]).

VI. Drug Screening Using sur-8

The present invention provides methods and compositions for using SUR-8 as a target for screening drugs that can alter Ras signalling, and thus the physiological effects of Ras (e.g., effects on cell growth, differentiation, and proliferation). For example, anticancer drugs can be identified by screening for compounds that target SUR-8 or regulate sur-8 expression.

In one screening method, the two-hybrid system discussed above and in Example 9 can be used to screen for compounds (e.g., drug) capable of altering (e.g., inhibiting) Ras/SUR-8 interactions (e.g., signal transduction) in vitro or in vivo. In one embodiment, a GAL4 binding site, linked to a reporter gene such as lacZ, is contacted in the presence and absence of a candidate compound with a GAL4 binding domain linked to a SUR-8 fragment and a GAL4 transactivation domain II linked to a Ras fragment. Expression of the reporter gene is monitored and a decrease in the expression is an indication that the candidate compound inhibits the interaction of SUR-8 with Ras. Alternately, the effect of candidate compounds on the interaction of SUR-8 with other proteins (e.g., proteins known to interact directly or indirectly with Ras) can be test in a similar manner.

In another screening method, candidate compounds can be evaluated for their ability to alter Ras signalling by contacting SUR-8, Ras, Ras-associated proteins, or fragments thereof, with the candidate compound and determining binding of the candidate compound to the peptide. The protein or protein fragments can be immobilized using methods known in the art such as binding a GST-SUR-8 fusion protein to a polymeric bead containing glutathione. A chimeric gene encoding a GST fusion protein can be constructed by fusing DNA encoding the polypeptide or polypeptide fragment of interest to the DNA encoding the carboxyl terminus of GST (See e.g., Smith et al., Gene 67, 31 [1988]). The fusion construct can be transformed into a suitable expression system (e.g., E. coli XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to disrupt the signal transduction pathway and thus regulate Ras-mediated physiological effects (e.g., proliferation).

In another screening method, one of the components of the Ras/SUR-8 signalling system, such as SUR-8 or a fragment of SUR-8, is immobilized. Polypeptides can be immobilized using methods known in the art, such as adsorption onto a plastic microtiter plate or specific binding of a GST-fusion protein to a polymeric bead containing glutathione. For example, GST-SUR-8 can be bound to glutathione-Sepharose beads. The immobilized peptide is then contacted with another peptide with which it is capable of binding in the presence and absence of a candidate compound. Unbound peptide can then be removed and the complex solubilized and analyzed to determine the amount of bound labeled peptide. A decrease in binding is an indication that the candidate compound inhibits the interaction of SUR-8 with the other peptide. A variation of this method allows for the screening of compounds that are capable of disrupting a previously-formed protein/protein complex. For example, a complex comprising SUR-8 or a SUR-8 fragment bound to another peptide is immobilized as described above and contacted with a candidate compound. The dissolution of the complex by the candidate compound correlates with the ability of the compound to disrupt or inhibit the interaction between SUR-8 and the other peptide.

Another technique for drug screening provides high throughput screening for compounds having suitable binding affinity to SUR-8 peptides and is described in detail by Geysen (WO 84/03564). Briefly, large numbers of different small peptide test compounds are synthesized on a solid substrate, such as plastic pins or some other surface. The peptide test compounds are reacted with SUR-8 peptides and washed. Bound SUR-8 peptides are then detected by methods well known in the art.

Another technique uses SUR-8 antibodies, generated as discussed above. Such antibodies capable of specifically binding to SUR-8 peptides compete with a test compound for binding to SUR-8. In this manner, the antibodies can be used to detect the presence of any peptide that shares one or more antigenic determinants of the SUR-8 peptide.

The present invention contemplates many other means of screening compounds. The examples provided above are presented merely to illustrate a range of techniques available. One of ordinary skill in the art will appreciate that many other screening methods can be used.

VII. Peptide Therapy

The methods of the present invention find use in treating diseases or altering physiological states characterized by unwanted proliferation of cells or other Ras-mediated effects. The invention provides methods for inhibiting SUR-8 interaction with Ras and Ras-associated proteins by administering peptides or peptide fragments of SUR-8. Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being administered concurrently.

Definitions

To facilitate understanding of the invention, a number of terms are defined below.

As used herein, the term "sur-8" refers to a gene that encodes the "SUR-8" protein.

The term "gene" refers to a nucleic acid (e.g., DNA) sequence that comprises coding sequences necessary for the production of a polypeptide or precursor (e.g., SUR-8). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' non-translated sequences. The sequences that are located 3' or downstream of the coding region and that are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "sur-8 gene" (or sur-8) refers to the full-length sur-8 nucleotide sequence (e.g., contained in SEQ ID NO:1). However, it is also intended that the term encompass fragments of the sur-8 sequence, as well as other domains within the full-length sur-8 nucleotide sequence. Furthermore, the terms "sur-8 nucleotide sequence" or "sur-8 polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histocherical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand. The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a mammalian SUR-8 protein includes, by way of example, such nucleic acid in cells ordinarily expressing a SUR-8 protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA).

As used herein, the term "purified" or "to purify" refers to the removal of contaminants from a sample. For example, anti-SUR-8 antibodies are purified by removal of contaminating non-immunoglobulin proteins; they are also purified by the removal of immunoglobulin that does not bind SUR-8. The removal of non-immunoglobulin proteins and/or the removal of immunoglobulins that do not bind SUR-8 results in an increase in the percent of SUR-8-reactive immunoglobulins in the sample. In another example, recombinant SUR-8 polypeptides are expressed in bacterial host cells and the polypeptides are purified by the removal of host cell proteins; the percent of recombinant SUR-8 polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual,* Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39–7.52 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign gene that is placed into an organism by introducing the foreign gene into newly fertilized eggs or early embryos.

The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Embryonal cells at various developmental stages can be used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438–4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873191 describes a method for the micro-injection of zygotes; the disclosure of this patent is incorporated herein in its entirety.

Retroviral infection can also be used to introduce transgenes into a non-human animal. The developing non-human embryo can be cultured in vitro to the blastocyst stage. During this time, the blastomeres can be targets for retroviral infection (Janenich, Proc. Natl. Acad. Sci. USA 73:1260–1264 [1976]). Efficient infection of the blastomeres is obtained by enzymatic treatment to remove the zona pellucida (Hogan et al., in *Manipulating the Mouse Embryo,* Cold Spring Harbor Laboratory Press, Cold Spring Harbor, N.Y. [1986]). The viral vector system used to introduce the transgene is typically a replication-defective retrovirus carrying the transgene (D. Jahner et al., Proc. Natl. Acad Sci. USA 82:6927–693 [1985]). Transfection is easily and efficiently obtained by culturing the blastomeres on a monolayer of virus-producing cells (Van der Putten, supra; Stewart, et al., EMBO J. 6:383–388 [1987]). Alternatively, infection can be performed at a later stage. Virus or virus-producing cells can be injected into the blastocoele (D. Jahner et al., Nature 298:623–628 [1982]). Most of the founders will be mosaic for the transgene since incorporation occurs only in a subset of cells which form the transgenic animal. Further, the founder may contain various retroviral insertions of the transgene at different positions in the genome which generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

A third type of target cell for transgene introduction is the embryonal stem (ES) cell. ES cells are obtained by culturing pre-implantation embryos in vitro under appropriate conditions (Evans et al., Nature 292:154–156 [1981]; Bradley et al., Nature 309:255–258 [1984]; Gossler et al., Proc. Acad. Sci. USA 83:9065–9069 [1986]; and Robertson et al., Nature 322:445–448 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468–1474 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells which have integrated the transgene. This technique obviates the need for growth of the transfected ES cells under appropriate selective conditions prior to transfer into the blastocoel.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis (See, Example 2, for a protocol for performing Northern blot analysis). Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots). The amount of mRNA present in the band corresponding in size to the correctly spliced SUR-8 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate.

The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding sur-8 (e.g., SEQ ID NO:1) or fragments thereof may be employed as hybridization probes. In this case, the sur-8-encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the regulation of Ras mediated signal transduction pathways.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); U (units), mU (milliunits); min. (minutes); sec. (seconds); % (percent); kb (kilobase); bp (base pair); PCR (polymerase chain reaction); BSA (bovine serum albumin); Fisher (Fisher Scientific, Pittsburgh, Pa.); Sigma (Sigma Chemical Co., St. Louis, Mo.); Promega (Promega, Corp., Madison, Wis.); Perkin-Elmer (Perkin-Elmer/Applied Biosystems, Foster City, Calif.); Boehringer Mannheim (Boehringer Mannheim, Corp., Indianapolis, Ind.); Clonetech (Clonetech, Palo Alto, Calif.); Quiagen (Quiagen, Santa Clarita, Calif.); Stratagene (Stratagene, Inc., La Jolla, Calif.); and NEB (New England Biolabs, Beverly, Mass.). Unless otherwise indicated, the restriction enzymes used in these Examples were obtained from NEB. *C. elegans* is available from the Caenorhabditis Genetics Center (CGC), at the University of Minnesota, St. Paul, Minn.

In the first set of Examples, the experiments were used to identify genes encoding SUR-8 by screening for suppressors of activated LET-60 Ras. The let-60 ras gene acts as genetic switch controlling vulval differentiation. As mentioned above, loss of LET-60 Ras function causes a Vulvaless phenotype while activated Ras causes a Multivulva phenotype. Since loss of activity in proteins that act downstream of LET-60 Ras in the Ras pathway or proteins that act to regulate the Ras pathway would reduce the signal transmitted through LET-60 Ras, mutations that can suppress the Multivulva phenotype of an activated let-60 ras mutation (n1046, G13E) were screened for in these Examples.

The screen allowed isolation of many mutations that define many genes involved in the signaling processes such as lin-45 raf, mek-2, sur-1/mpk-1, sur-2, ksr-1, sur-6 and other genes. While this screen has been highly successful, the efficiency of the screen has been limited by the fact that animals homozygous for the activated let-60(n1046) allele display a Multivulva phenotype only 85% of the time. The incomplete penetrance increases the incidence of identifying false suppressors and dramatically limits the number of genomes that can be screened for suppressor mutations. In order to increase efficiency of the screen, transgenic worms that contain multiple copies of the activated let-60 ras gene and are 100% Multivulva were developed and used to screen for additional suppressor mutations. The sur-8 gene was identified by this modified screen.

Example 1

Development of let-60 Gain-of-Function Transgenic Stains

In this Example, a let-60 ras (gf) transgenic strain for screening ras suppressors was developed. To construct the strain with completely penetrant Multivulva phenotype, wild type *C. elegans* (N2 strain) obtained from the *C. elegans* Genetic Center (CGC, University of Minnesota, St. Paul, Minn.) were transformed with cloned let-60 ras(n1046) mutant genomic DNA fragment described by Han and Sternberg (Han and Sternberg, Genes Develop., 5:2188–2198 [1991]).

Transformation was performed by microinjecting DNA to the gonad of *C. elegans* adult (Mello et al., EMBO J., 10:3959–3970 [1991]). Briefly, the DNA sample to be tested, along with a DNA marker was directly injected into the distal arm of the gonad of *C. elegans* hermaphrodites. The injected animals were allowed to grow for 3–4 days. Their F1 progeny were screened for transformants that showed the marker phenotype.

The host strain was of the genotype dpy-20. The dpy-20 mutation causes the worms to have a "Dumpy" phenotype (i.e., the worms are shorter and fatter than "normal" worms). The injection solution contained three plasmids: pMH132 (1 μg/ml) which contains the activated let-60 ras (n1046) mutant gene (Han and Sternberg, supra), pMH86 (10 μg/ml) which contains the dpy-20(+) genomic DNA fragment described in Han and Stemberg (Han and Sternberg, supra), and Bluescript SK(+)(Stratagene) (100 μg/ml) which served as a carrier. pMH132 contains a 7 kb BamHI-XhoII let-60 ras genomic fragment with codon 13 changed from GGA (glycine) to GAA (Glu) cloned into pBluescript SK+ (Stratagene). This change corresponds to nucleotide 2697 being changed from a G in the wild-type sequence (FIGS. 12A–12C [SEQ ID NO:9]) to an A in the mutant sequence (FIGS. 13A–13C [SEQ ID NO:10]). The dpy-20(+) plasmid served as a transformation marker that rescues the Dumpy phenotype of the host strain. For example, for worms with the Dumpy phenotype due to mutations in the dpy-20 gene, injection of the DNA containing a wild-type dpy-20 gene would revert the Dumpy phenotype into wild-type, which would then be picked in F1 progeny as transformants. Although there is variation between the DNA sample tested and the type of marker DNA used, certain percentages of the F1 transformants were stable transformants whose progeny continued to contain the injected DNA. In stable transformants, many copies of injected DNA (both the marker DNA and test DNA) form a long extrachromosomal array.

To obtain stable lines carrying an extra chromosomal array of injected DNA, non-Dumpy, Multivulva progeny from injected animals were selected in the F1 generation three days after completion of the transformation process. Non-Dumpy Multivulva animals were selected again in the F2 generation three days later. The F2 transformants were found to stably carry the injected DNA as an extrachromosomal array.

To integrate the array into the genome, transgenic animals from these lines were gamma-irradiated at a dose of 3600 rads. Their F1 non-Dpy progeny were picked singly to plates to identify those in which the transgene had integrated into the genome (resulting in a 75% transmittance to the F2). Lines bearing integrated transgenes were obtained at a frequency of approximately 1 in 200 F1s picked. Two transgenic lines, kuIs13 and kuIs14 (i.e., let-60[n1046]) were obtained. Prior to analysis, each line was backcrossed one time to the parent dpy-20 strain to remove any other background mutations.

Example 2

Screen for Ras Suppressors

In this Example, a screen for suppressors of the Multivulva phenotype were conducted. First, kuIs14 let-60 (kuIs14) homozygotes that are nearly 100% Multivulva were used as a parental strain to screen for suppressors of the Multivulva phenotype. Several plates of mixed staged kuIs14 animals were collected in a 15 ml tube. After washing once in a salt solution (M9; See e.g., Sambrook et al., *Molecular Cloning: A Laboratory Manual,* Cold Spring Harbor Laboratory Press, Cold Spring Harbor, N.Y. [1989]), the worms were treated with mutagen ethylmethanesulfonate (EMS) at 50 mM (20 µl concentrated EMS were added to 4 ml of worms in M9 solution). The tube was gently shaken in a hood for four hours. The worms were then washed three times with about 10 ml M9 solution to wash off EMS. The worms were then placed in a fresh culture plate. Two-to-three hours later, fourth larval stage worms were picked and individually placed in culture plates.

For each screen approximately 200 plates were used to screen the progeny of 200 treated worms. These plates were incubated in a 20° C. incubator. Three days later, the average number of F1 progeny a single worm produces was estimated. About 7–8 days later, screening was conducted for suppressed F2 animals (i.e., non-Multivulva) from each plate under a dissecting microscope. Non-Multivulva animals were selected and individually placed on a new plate labeled with a number. Candidates from the same parent plate may not be independent mutants and were thus assigned the same plate number. If the picked candidate continued to produce mainly non-Multivulva progeny, this line of worms was considered a good candidate to contain a suppressor mutation.

In total, 22,000 mutagenized chromosome sets were screened (i.e., F2 progeny from 11,000 F1 progeny of treated parents were screened). Twenty suppressor mutations were initially isolated, these were later narrowed down to eleven suppressors after out-crossing, as described in Example 3.

Example 3

Outcrossing

In this experiment, candidate suppressors were outcrossed to remove any additional mutations from the genome. Prior to outcrossing, each candidate had the following genotype: dpy-20/dpy-20; let-60(kuIs14)/let-60(kuIs14); suppressor/suppressor. These animals were mated with males with a genotype of let-60(n1046 gf)+/+dyp-20(e1282); him-5 (e1490)/him-5(e1490). The dpy-20 gene is extremely close to the let-60 gene and thus a good balance in the strain. The him-5 mutation leads to male production. F1 progeny having a genotype of let-60(n1046 gf)+/+dpy-20; let-60(kuIs14)/+; suppressor/+ were selected by selecting for non-Dpy hermaphrodites. Since most of the suppressors are recessive or semi-dominant, these animals were Multivulva. F2 non-Multivulva progeny were selected to obtain strains of let-60(n1046)/let-60(n1046); suppressor/suppressor. These strains continued to produce mostly non-Multivulva animals. Further outcrossings were done in similar way using the same male strain. Since the male strain has the him-5 mutation, strains of genotype let-60(n1046)/let-60(n1046); him-5(e1490)/him-5(e1490) were also obtained in order to facilitate mapping. In total, 11 candidates were outcrossed at least four times and each one suppressed the Multivulva phenotype to less than 5%.

Example 4

Genetic Mapping of *C. elegans* sur-8

In these experiments, genetic mapping was conducted on the mutant worms, using two point genetic mapping to assign each suppressor to one of the six chromosomes. In these experiments, males from suppressor strains of genotype let-60(n1046)/let-60(n1046); him-5/him-5; suppressor/suppressor were used to mate with mapping strains of genotype let-60(n1046)/let-60(n1046); marker/marker. The suppressor strain used in these experiments is non-Multivulva, while the marker strains have a marker mutation on the chromosome being tested, are Multivulva, and have the marker phenotype. There are many different marker phenotypes that can be used for mapping, including dpy genes (Dumpy or "dpy"; mutations in these genes cause a Dumpy phenotype, such that the worms are shorter and fatter than normal worms), unc genes (Uncoordinated or "unc"; these worms cannot move or move in an uncoordinated manner), rol genes (Roller or "rol"; in which worms roll, rather than swim), vab genes (mutations in these genes cause variable phenotypes), bli genes (mutations in these genes result in animals with blisters ["Bli"]), and lon genes (mutations in these gels result in long animals ["lon"]).

After the mating, the F1 non-Multivulva, non-Marker phenotype animals were selected by inspection. These animals have genotypes of let-60(n1046)/let-60(n1046); marker/+; suppressor/+. Individual F2 non-Multivulva animals were then picked to individual plates. For typical mapping experiments, 20 to 40 such animals were selected for each marker used. In the next generation, it was necessary to first confirm that the animal picked was indeed suppressed (most or all F3 progeny were non-Multivulva, let-60(n1046)/let-60(n1046); suppressor/suppressor). Then, the determination was made whether each plate contained animals with a marker phenotype (marker/marker). If the suppressor mutation was located on the same chromosome as the marker (and not far from the marker mutation), it was not expected that animals of the Marker phenotype would be observed in any suppressed plates. On the other hand, if the suppressor mutation was located on a different chromosome as the marker gene, the two mutations should segregate independently and it was expected that animals with a marker phenotype should be observed in about ⅔ of the plates. If the suppressor mutation was located on the same chromosome as the marker gene but they are not near each other, it was expected that some plates would contain animals with the marker phenotype. Of the 11 suppressors mapped, three were mapped on chromosome I, and the rest were mapped on chromosomal IV.

At the conclusion of the above experiments, three point mapping was used to more precisely define the locations of the 11 suppressors within the worm chromosome. Three point mapping is similar to two point mapping except that the mapping strain contains two mapping markers instead of just one. Briefly, in the three-point mapping method, the suppressor mutation is mapped relative to two different markers on the same chromosome. For example, to determine the location of the sur-8(k167) mutation on chromosome IV, a marker strain homozygous for three mutations on the chromosome IV, dpy-13 unc-5 let-60(n1046, G13E) was constructed first. This strain has three phenotypes: Dumpy, Uncoordinated, and Multivulva due to the three mutations (the construction of the strain is described in Example 7). Then, sur-8(ku167) let-60(n1046);him-5 males were crossed into this above strain. The him-5 mutation allows the production of males. The cross progeny with the genotype: dpy-13 unc-5 let-60(n1046)/+sur-8(ku167)+let-60(n1046);him-5/+ were then selected. The cross progeny were neither Dumpy nor Uncoordinated because the dpy-13 gene and the unc-5 genes are heterozygous. The progeny is still Multivulva because the let-60 mutation is homozyous but the sur-8 mutations is heterozygous. Each of many F1 animals with the phenotype distinction were picked and placed onto fresh plates.

From such heterozygous worms, F2 recombinants that display either Dumpy or Uncoordinated phenotype, but not both, were selected. These recombinants were picked and placed individually onto fresh plates. The next generation of recombinants was scored (i.e., how many of the total number of animals) segregating the "suppressor" phenotype (i.e., how many of the recombinants give rise to F3 animals that are no longer Multivulva (suppressed) and thus contain the suppressor mutation (sur-8)). In this manner, the locations of the sur-8 mutations relative to the dpy-13 and unc-5 genes on the chromosome were determined (See, Example 7 for actual mapping data).

At the conclusion of the two and three point mapping experiments, complementation tests were conducted in order to test whether the suppressors were mutations in known genes with similar map positions. Using these methods, it was determined that the three suppressors mapping to chromosome I were alleles of the mek-2 gene and three suppressors mapping to chromosome IV were alleles of lin-45 raf. In addition, four other alleles mapped on the left side of IV. Using the genetic markers dpy-13 and unc-5, the remaining allele, ku167, was mapped to a genetic map position on chromosome IV, where no known genes involved in the Ras pathway were located. This allele defines the sur-8 gene.

Example 5

Genetic Characterization of sur-8

A. sur-8(ku167) is a Loss-of-Function Mutation

In these experiments, the genetic nature of the sur-8 allele, ku167, was investigated. To determine the genetic nature of the ku167 mutation, (i.e., if it is a loss-of-function, gain-of-function, or dominant negative allele), the phenotype of ku167 homozygotes was compared to animals with ku167, in trans, to a deficiency that uncovers the sur-8 locus. Because the ku167 mutation does not cause a phenotype in an otherwise wild-type background, the severity of the Suppression phenotype was compared in a let-60(n1046) background. The small deficiency mDf4 failed to complement sur-8(ku167) for the Suppression phenotype (See e.g., Table 1). Thus, ku167 is a loss-of-function allele.

mDf4 is linked to the semi-dominant dpy-13 allele, e184 (Rogalski and Riddle, Genetics 118, 61 [1988]). For deficiency analysis, mDf4 was linked to let-60(n1046) by selecting Muv semi-Dpy recombinants from dpy-13 mDf4/unc-5 let-60(n1046) heterozygotes. The recombinant dpy-13 mDf4 let-60(n1046) chromosome was balanced with nT1 and used to do a complementation test with either unc-5 sur-8(ku167) let-60(n1046) or unc-5 let-60(n1046) by scoring non-Unc, semi-Dpy cross progeny [genotype: unc-5+/–sur-8(ku167) let-60(n1046); dpy-13 mDf4 let-60(n1046)] for percent Muv and percent induction.

TABLE 5

Sur-8 and Multivulva Percentage

| Genotype | Multivulva % |
|---|---|
| Wild-Type | 0% |
| let-60(n1046) | 88% |
| sur-8(ku167) let-60(n1046) | 4% |
| sur-8(ku167) | 0% |

B. Epistatic Analysis

Next, in order to determine the relationship between sur-8 and other genes acting in the Ras pathway, epistatic analysis with mutations that cause a Multivulva phenotype was conducted. If a mutation in sur-8 can suppress the Multivulva phenotype caused by a given Muv mutation, then sur-8 must act genetically downstream of or in parallel to that mutation. However, if the Muv phenotypes is not suppressed by a sur-8 mutation, then sur-8 must act genetically upstream of or in parallel to that mutation. Double mutants between sur-8(ku167) and mutations in let-60 ras, lin-45 raf; lin-15 and lin-1 were constructed using standard genetic techniques.

For example, to construct a sur-8(ku167) lin-15(n765) animal, lin-15(n765) males were crossed with sur-8(ku167) unc-5(e53) hermaphrodites. In this procedure, the unc-5 mutation which closely linked to the sur-8 gene served as a marker (Uncoordinated movement mutant phenotype). The F1 cross progeny (the non-Uncoordinated, genotype was sur-8 unc-5/++; lin-]5/+) were placed on fresh plates and allowed to produce F2 progeny. F2 Multivulval animals were first selected to obtain lin-15 homozygotes that were still heterozygous for the sur-8 and unc-5 mutations (sur-8 unc-5/++; lin-15/lin-15). In the next generation, Uncoordinated animals that should have the genotype of sur-8(ku167) unc-5(e53)/sur-8(ku167) unc-5(e53); lin-15(n765)/lin-15 (n765) were picked (this genotype is also written as sur-8 (ku167) unc-5(e53); lin-15(n765)). The other double mutants were constructed in a similar manner.

For epistasis analysis with the gain-of-function raf mutation, a transgenic strain containing an extrachromosomal array called kuIs17 was generated. kuIs17 is a transgene containing raf(gf) (pMS88) and dpy-20(+) genomic DNA (pMH86, Han and Sternberg 1991, supra) integrated into the genome. pMS88 contains a Drosophila raf gain-of-function mutant gene cloned into the HSP16 vector pPD49.83 (gift from Andrew Fire, Carnegie Institute of Washington, Department of Embryology, Baltimore, Md.). In this raf(gf) gene, the kinase domain of Draf is fused to the transmembrane domain of the Torso receptor (Dickson et al., Nature 360, 600 [1992]).

Epistatic analysis indicated that sur-8 acts downstream or in parallel to let-60 ras and upstream of the lin-45 raf. It was found that ku167 can suppress the Multivulva phenotype caused by let-60(n1046gf) and can also suppress the Multivulva phenotype of a loss-of-function lin-15, indicating that ku167 is not an allele-specific suppressor (i.e., it can suppress ras pathway signaling when Ras is wild type). ku167 does not suppress the Multivulva phenotype caused by a loss-of-function mutation of lin-1 or an activated raf transgene. Because ras and raf have been shown to directly interact, sur-8 likely defines a branch point either feeding into raf or out of ras.

TABLE 6

Sur-8 and Multivulva Percentages

| Genotype | Multivulva % |
|---|---|
| let-60(n1046) | 88% |
| sur-8(ku167) let-60(n1046) | 4% |
| raf(kuIs17gf) | 43% |
| sur-8(ku167); raf(kuIs17gf) | 50% |
| lin-15(n765) | 95% |
| sur-8(ku167); lin-15(n765) | 49% |

C. Synergistic Effect Between sur-8 and Mutations in Other Genes

In these experiments, the interaction between sur-8 and other genes was investigated. sur-8 was found to play an important positive function in Ras signaling and it was thought that it is likely to act in parallel to lin-45 raf and ksr-1.

sur-8(ku167) alone was not found to cause vulval induction defects or other obvious defects. However, this mutation may still significantly lower Ras pathway activity and its effects on pathway activity may only be observed when the activity of other Ras pathway genes are compromised. To make this determination, double mutants were constructed and examined for vulval induction defects. For example, to construct a sur-8(ku167); ksr-1ku68) double mutant, sur-8 (ku167) unc-24 (e138)/++ males were crossed with lon-2 (e678) ksr-1(ku68) hermaphrodites. Here, the unc-24 mutation (i.e., "Uncoordinated") served as a marker for the sur-8 gene, while the lon-2 mutation (i.e., "Long") serves as a marker for the ksr-1 gene. The F1 cross progeny hermaphrodites that were neither Long nor Uncoordinated were picked and placed onto fresh plates. Among progeny of the next two generations, animals with both Long (i.e., which indicates homozygosity for the ksr-1 and lon-2 mutations), and Unc (i.e., which indicates homozygosity for the sur-8 and unc-24 mutations), were picked. The genotype of the final strain was sur-8(ku167) unc-24 (e138)/sur-8(ku167) unc-24 (e138); lon-2(e678) ksr-1(ku68)/lon-2(e678) ksr-1 (ku68).

It was found that ku167 strongly enhanced the Vulvaless and Lethal phenotypes caused by a weak loss-of-function mutation in sur-1/mpk-1 MAP kinase or a strong loss-of-function mutation in ksr-1. Single mutants displayed wild-type vulval induction and almost no lethality while double mutants (i.e., from heterozygous mothers) were completely Vulvaless and all of their progeny died as larvae.

TABLE 7

Vulval Induction and Lethality Associated with Various Genotypes

| Genotype | Vulval Induction % | Lethal % |
| --- | --- | --- |
| sur-8(ku167) | 100% | 0% |
| sur-1(ku1) | 98% | 7% |
| ksr-1(ku68) | 100% | 24% |
| sur-1(ku1); sur-8(ku167) | 0% | 100% |
| sur-8(ku167); ksr-1(ku68) | 4% | 85% |

Example 6

Isolation of Additional sur-8 Mutants

In these experiments, additional sur-8 mutations were isolated. In these experiments, a non-complementation screen was used. First, a strain of genotype unc-24(e138) let-60(n1046); lon-2(e678)xol-1(y9) was constructed. Unc-24 was used in these animals because it is closely linked to sur-8 and is useful for marking the mutant chromosome and for identifying cross progeny. The gene let-60(n1046) causes a Multivulva phenotype; it is this phenotype that is screened for suppression. The gene xol-1, which is lethal to males, is used to prevent hermaphrodite cross progeny from mating with their siblings before being cloned. This made the screening process less labor intensive.

In the non-complementation screen, hermaphrodite animals were mutagenized with EMS, and examined in the same way as described above. Unc-24(e138) let-60(n1046); lon-2(e678)xol-1 (y9) hermaphrodites were then mated with sur-8(ku167) let-60(n1046); him-5(e1490) males. In the next generation, suppressed F1 progeny were picked onto individual plates. It was thought that if the strain contained a new sur-8 mutation, the genotype on chromosome IV would be sur-8(new allele) unc-24(e138) let-60(n1046)/sur-8(ku167) let-60(n1046). The F2 progeny of this F1 would then give nearly all suppressed animals, and the Unc progeny would be suppressed.

Approximately 10,000 F1 animals from mutagenized mothers were screened. Several candidate new mutations were identified. After outcrossing five times (as described above in Example 3) and DNA sequencing, one, "ku242," was determined to be a new sur-8 mutation.

Example 7 sur-8 Cloning

A. Further Genetic Mapping of sur-8 Mutations

The sur-8 mutations ku167 was first mapped to chromosome IV by using the marker unc-24 dpy-20 as described above. Three point mapping, as described above in Example 4, was used to pinpoint the specific genetic location of sur-8. Then, sur-8 was mapped with the genetic markers dpy-13 and unc-5, both of which have been cloned so as to have a precise physical map position. The strain dpy-13(e184) unc-5(e53) let-60(n1046) was then constructed, and used it to cross with sur-8(ku167) let-60(n1046); him-5(e1490) males. The dpy-13 (e184) unc-5(e53) let-60(n1046) strain was constructed by crossing let-60(n1046)/+ males into a dpy-13 (e184) unc-5(e53) double mutant obtained from the C. elegans Genetic Center. The F1 progeny with the genotype dpy-13 unc-5+/++let-60 were picked and screened for recombinants that were Dumpy, Uncoordinate and Multivulva. Animals with all three phenotypes were identified as the triple mutants of interest. Non-Unc, non-Dpy F1 cross progeny were then picked to individual plates and the F2 progeny were screened for Dpy non-Unc and Unc non-Dpy recombinants. The three-point mapping method (e.g., as described in Example 4) was used to provide these recombinants (i.e., F2 progeny animals that contained Dumpy, but not the Uncoordinated phenotype, or the animals that contained Uncoordinated, but not the Dumpy phenotype, were picked).

After allowing the recombinant chromosomes to become homozygous, the recombinants were scored for the presence or absence of the ku167 mutation by virtue of their ability to suppress the Multivulva phenotype caused by let-60(n1046). Using this approach, it was determined that 46 out of 52 Dpy non-Unc recombinants had the ku167 allele, and two out of 18 Unc-non Dpy recombinants had the ku167 allele. These data allowed the placement of sur-8 at position 1.72 of chromosome IV on the genetic map.

B. Microinjection Transformation

The chromosome region containing the sur-8 gene is covered by mapped cosmids containing approximately 40 kb genomic fragment inserts constructed by the C. elegans genome project. In these experiments, the specific cosmid DNA containing the sur-8 gene was identified.

First, using the methods described in Example 1, cosmids were injected in the region to see which one could rescue the sur-8 phenotype. The host strain had a genotype of sur-8 (ku167) let-60(n1046); unc-119(ed3). Cosmids AC7 and C02B10 were tested at a concentration of 5 μg/ml, together with a transformation marker plasmid consisting of unc-119 genomic DNA insert. Animals transgenic for the marker plasmid displayed a non-Unc phenotype and these animals were also often found to contain the coinjected cosmid. Thus, it was possible to assay the cosmid for rescue. After the injection of gravid adults, non-Unc F1 progeny were selected. In the next generation, stable non-Uncs were selected and scored for percentage of Multivulva phenotype. It was found that let-60(n1046)/let-60(n1046) animals were 88% Multivulva and the host strain sur-8(ku167) let-60 (n1046)/sur-8(ku167) let-60(n1046) was less than 5% Multivulva. If the cosmid contained the sur-8 gene, loss of the sur-8 function by the ku167 mutation would be rescued, and result in loss of the suppression (i.e., become Multivulva). In 5 out of 6 transgenic lines generated, cosmid AC7 rescued the ku167 mutant defect and was thus likely to contain the sur-8 gene.

C. Subcloning and Sequencing of Sur-8

In order to identify the sur-8 gene, the rescuing cosmid AC7, which contains a 40 kb insert and several predicted genes, was divided into small plasmids by digesting it with restriction endonucleases and subcloning the fragments into the pBluescript vector. For example, the cosmid was digested with Pstl and Sac II, and a 13 kb fragment was isolated after running the DNA sample on an agarose gel. This fragment was ligated with pBluescipt SK+ (which was also digested with Pstl and Sac II). The ligation mix was then transformed into E. coli. The resulting new plasmid is called "pDS12,"; this plasmid was eventually shown to be able to rescue the mutant phenotype.

These plasmids were again tested for rescuing activity. Plasmid pDS12 which contained a 10 kb insert derived from AC7 was able to rescue, while other subfragments derived from other regions of AC7 were not. Based on the genome sequencing project sequence prediction of AC7, there was a single predicted gene located within the rescuing 10 kb fragment. To identify the sur-8 cDNA, a C. elegans mixed stage library λgt11 (kindly provided by Peter Okeema, while he was at the Carnegie Institute in Baltimore) was screened using a 2 kb DNA probe derived from the region of the predicted gene on the rescuing subclone using standard phage hybridization methods. Of two million library clones screened, 10 hybridizing clones were identified. The two longest clones (2.1 kb) were sequenced to obtain the sur-8 cDNA sequence (SEQ ID NO:1). The sur-8 cDNA is predicted to encode a novel protein of 559 amino acids (SEQ ID NO:2).

D. Sequence of the Sur-8 Mutants

To prove that the cDNAs isolated in the above experiments corresponds to sur-8, the molecular lesion of both sur-8 alleles (ku167 and ku242) by amplifying sur-8 genomic DNA from lysed ku167 or ku242 worms was investigated. First, the mutant worms were lysed, and PCR was conducted on the sur-8 genomic DNA using PCR primers designed based on the genomic sequence (Exon 1: 5' TTCCAAGAGTCTCTCATCGG (SEQ ID NO:11) and 5' ATGAAATCTCATAATGCCCAC (SEQ ID NO:12); Exons 2, 3, and 4: 5' CTGTGATAAAGTATTCAATTTCAC (SEQ ID NO:13) and 5' GCATTTCAAATTTTTCAGAGC (SEQ ID NO:14); Exons 5, 6, and 7: 5' TCATTTGAAG-CAAAATCCCCC (SEQ ID NO:15) and 5' AACTCAC-CAATTTCCTCGGG (SEQ ID NO:16); and Exon 8: 5' GGATCTTGGACATCAATCACC (SEQ ID NO:17) and 5' GAAAACAAGTTTTGCAACCCG (SEQ ID NO:18)). For most experiments, the PCR conditions were 94° C. for 1 minute, followed by 35 cycles of 94° C. for 30 seconds, 1 minute at 55° C., and 30 seconds to 2 minutes (depending upon length) at 72° C., followed by 7 minutes at 72° C. Taq DNA polymerase was used in all of the PCR runs. The PCR fragments were then purified from an agarose gel using a Qiagen column (Qiagen's QIA quick PCR purification kit) as described by the manufacturer.

The genomic fragments were sequenced using an ABI automated sequencer. Both mutations were found to be G to A transitions within the coding region of the sur-8 cDNAs, causing missense mutations in the encoded amino acids. The fact that mutations were found in the cDNA that was isolated provides proof that sur-8 was cloned. The complete DNA sequence (SEQ ID NO:1) and predicted amino acid sequence (SEQ ID NO:2) of sur-8 are provided in FIGS. 9A–9D.

TABLE 8

Genetic Analysis of Sur-8

| Allele | cDNA Lesion | Amino Acid Substitution |
| --- | --- | --- |
| ku167 | G1289A | E430K |
| ku242 | G698A | C233Y |

Example 8

Mammalian sur-8 Cloning

A. Computer Search for sur-8 Homologues

The SUR-8 protein sequence identified as described above was used to search for homology with human and mouse EST sequences deposited in the EST Genbank database. Two partial gene sequences, one human (Genbank accession number W81200) and one mouse (Genbank accession number AA119714), were found to display significant homology with the SUR-8 C-terminal region. Additional overlapping human and mouse EST sequences were identified from the EST database which contained DNA sequences that were identical to the original two EST clones. These clones were all between 49% and 70% identical to C-terminal regions of SUR-8 but together did not cover the full length of SUR-8.

B. Cloning of Full-Length Mammalian sur-8

In order to isolate the full length human and mouse sur-8, DNA primers were designed based on the human and mouse EST sequences to screen human and mouse cDNA for the presence of sur-8 cDNA using the 5' RACE strategy. The sur-8 primers used were: 5' TGGTAGAAAACTGAGCTG-GACCACCC (human)(SEQ ID NO:3) and 5' GGGATCTTTGTGAGCTGATTAGTCGC (mouse)(SEQ ID NO:4). Template DNA was Marathon-Ready cDNA (Clonetech), and was either derived from human brain or mouse liver. 5' RACE was performed using the Clonetech Marathon-Ready cDNA RACE kit (Clonetech, catalogue number PT1156-1).

Using the above primers in conjunction with the AP1 primer provided in the kit and following the manufactures protocol, a 1.6 kb fragment from the human brain library and a 1.6 kb fragment from the mouse liver library were amplified. These DNA fragments were sequenced directly and were found to overlap exactly at their 3' end with the EST sequences. The sequences from the ESTs and the 5' RACE were compiled to generate full-length mouse and human sur-8 cDNA sequences (SEQ ID NOS:5 and 6, respectively). The DNA and predicted protein sequences from human sur-8 are shown in FIGS. 10A–D, and the DNA and predicted protein sequences from mouse SUR-8 are shown in FIGS. 11A–11D. These sequences were found to be 98% identical at the amino acid level.

Example 9

SUR-8-Ras Interaction

In these experiments, the physical interaction between SUR-8 and Ras was investigated. The yeast two-hybrid interaction system was used to test interaction between SUR-8 and RAS.

First, a sur-8-gal4 activation domain fusion protein was constructed by cloning human or *C. elegans* sur-8 cDNA in-frame into the Gal4 activation domain fusion construct pACT2 (Clonetech). In this construct, the 1.7 kb sur-8 cDNA was PCR amplified and cloned into the NocI and BamHI sites of pACT2.

Next, a Ras-gal4 DNA binding domain fusion protein was constructed by cloning either let-60 ras, H-ras, N-ras, or K-ras cDNA in-frame into the gal4 DNA binding domain fusion construct pAS2 (Clonetech). Then, interaction between the fusion proteins as described in Clonetech's two-hybrid kit (Matchmaker System 2) were tested, using the manufacturer's instructions.

A strong interaction was detected between *C. elegans* SUR-8 and LET-60 RAS. In addition, a strong interaction was detected between human SUR-8 and N-Ras, a weaker interaction with K-Ras, and no interaction with H-Ras. As a positive control for RAS expression, all RAS fusion protein were shown to be bound to a Raf1 fusion. As a control for SUR-8 binding specificity, it was shown that *C. elegans* SUR-8 fails to bind to fusions with other Ras pathway components tested (i.e., LIN-45, KSR-1, MPK-1, and MEK-2). The Table below indicates the level of binding between these components, in this Table, "+" indicates strength of binding and "−" indicates no detectable binding (i.e., the greater the number of "+," the stronger the binding).

TABLE 9

Interaction of SUR-8 and Various Other Proteins

|  | *C. elegans* SUR-8 | Human SUR-8 | Raf1 |
|---|---|---|---|
| let-60 RAS | +++ | +++ | +++ |
| N-Ras | ++ | +++ | +++ |
| K-Ras | − | + | +++ |
| H-Ras | − | − | +++ |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, or related fields are intended to be within the scope of the following claims.

SEQUENCE LISTING

<160> NUMBER OF SEQ ID NOS: 18

<210> SEQ ID NO 1
<211> LENGTH: 1680
<212> TYPE: DNA
<213> ORGANISM: Caenorhabditis elegans

<400> SEQUENCE: 1

```
atggagacat cgaaggagtt cgaattccgt ccggccaagg agacgtcacg ctccaagagt      60
cccggtggaa tcgtcggaag actttcgaat tttgcgcgaa acaaggcgag gcattcgttg     120
agtgaaaaag gttcaaattc ggttggtgga agtggtggag caggttttga taaaccgaga     180
aaggacctcc taaaagaatt tcacaaatgc aaagaggcgc aggatcagag attagatttg     240
agctcaatcg agatcacgag cattccgtcg ccgatcaaag agctcacaca gctgacagaa     300
ttgttcttgt acaagaacaa gttgacgtgc ttgccaacgg aaataggtca actggtgaat     360
ctcaagaaac ttggtctctc tgaaaatgcg cttacatctc ttccggattc acttgcttct     420
ctggaatcac tggaaacatt ggatttacgg cacaacaagt tgacagaggt tccatcggtc     480
atttacaaaa tcgggtcgct cgaaacatta tggctgaggt acaatcgaat tgtggcagtt     540
gacgaacaaa ttggaaatct gtcaaaattg aaaatgttgg atgttcgtga gaataagatt     600
cgagagttac catctgcaat tggaaaactg acgtcactgg ttgtgtgtct tgtctcttat     660
aatcatttaa cacgggttcc tgaagaaatc ggtgactgcc attccctgac tcaactcgat     720
cttcaacaca acgacctctc agaactaccg tactcaatag gaaaactcgt gaatcttgtt     780
cgaatcggaa ttcgatacaa taagattcga tgtattccaa gtgaattgga aagttgtcag     840
cagctcgagg aatttattgt agagagcaat catttgcaat tactaccgcc aaacctgctc     900
```

```
acaatgcttc caaaaatcca cacagtgaat ctctcacgga acgagttgac tgcattcccg    960
gcaggcggac ctcaacaatt tgtgtccaca gtcacaatta atatggaaca caatcagatt   1020
tcaaagattc caatcggaat attctcgaaa gcaacacgat taacaaaact gaatttgaag   1080
gaaaatgagc tggtctcgtt gcctttggac atgggatctt ggacatcaat caccgagctc   1140
aatctctcca caaatcaatt gaaagttttg ccagaagata tcgaaaaact tgtgaatctg   1200
gaaatccttg tgctgtccaa caatcaactg aaaaagcttc caaatcaaat aggaaatctc   1260
aataaactcc gcgagctgga tctcgaggaa atgaattgg agaccgttcc aactgaaatc   1320
ggatttttac aacatcttac gaaactgtgg gttcagtcaa acaagatttt gactctacca   1380
agatccattg gaaatttgtg ttcgcttcaa gatttgcgat tgggagagaa caatttgaca   1440
gcgattcccg aggaaattgg ccacctcgac tcattgaaat ctctataacct caacgacaac   1500 tcctctcttc acaatttgcc atttgagttg gcactgtgcc aatcgcttga ataatgtca    1560 atcgaaaact ctccactttc tcagattcca cctgaaatca ctgctggtgg tccttcactt   1620
gtgatacaat atcttaaaat gcaaggtccc tatcgaggag ttgtgatgaa ttctcaataa   1680
```

<210> SEQ ID NO 2
<211> LENGTH: 559
<212> TYPE: PRT
<213> ORGANISM: Caenorhabditis elegans

<400> SEQUENCE: 2

```
Met Glu Thr Ser Lys Glu Phe Glu Phe Arg Pro Ala Lys Glu Thr Ser
  1               5                  10                  15

Arg Ser Lys Ser Pro Gly Gly Ile Val Gly Arg Leu Ser Asn Phe Ala
             20                  25                  30

Arg Asn Lys Ala Arg His Ser Leu Ser Glu Lys Gly Ser Asn Ser Val
         35                  40                  45

Gly Gly Ser Gly Gly Ala Gly Phe Asp Lys Pro Arg Lys Asp Leu Leu
     50                  55                  60

Lys Glu Phe His Lys Cys Lys Glu Ala Gln Asp Gln Arg Leu Asp Leu
 65                  70                  75                  80

Ser Ser Ile Glu Ile Thr Ser Ile Pro Ser Pro Ile Lys Glu Leu Thr
                 85                  90                  95

Gln Leu Thr Glu Leu Phe Leu Tyr Lys Asn Lys Leu Thr Cys Leu Pro
            100                 105                 110

Thr Glu Ile Gly Gln Leu Val Asn Leu Lys Lys Leu Gly Leu Ser Glu
        115                 120                 125

Asn Ala Leu Thr Ser Leu Pro Asp Ser Leu Ala Ser Leu Glu Ser Leu
    130                 135                 140

Glu Thr Leu Asp Leu Arg His Asn Lys Leu Thr Glu Val Pro Ser Val
145                 150                 155                 160

Ile Tyr Lys Ile Gly Ser Leu Glu Thr Leu Trp Leu Arg Tyr Asn Arg
                165                 170                 175

Ile Val Ala Val Asp Glu Gln Ile Gly Asn Leu Ser Lys Leu Lys Met
            180                 185                 190

Leu Asp Val Arg Glu Asn Lys Ile Arg Glu Leu Pro Ser Ala Ile Gly
        195                 200                 205

Lys Leu Thr Ser Leu Val Val Cys Leu Val Ser Tyr Asn His Leu Thr
    210                 215                 220

Arg Val Pro Glu Glu Ile Gly Asp Cys His Ser Leu Thr Gln Leu Asp
225                 230                 235                 240
```

-continued

```
Leu Gln His Asn Asp Leu Ser Glu Leu Pro Tyr Ser Ile Gly Lys Leu
                245                 250                 255

Val Asn Leu Val Arg Ile Gly Ile Arg Tyr Asn Lys Ile Arg Cys Ile
            260                 265                 270

Pro Ser Glu Leu Glu Ser Cys Gln Gln Leu Glu Glu Phe Ile Val Glu
        275                 280                 285

Ser Asn His Leu Gln Leu Leu Pro Pro Asn Leu Leu Thr Met Leu Pro
    290                 295                 300

Lys Ile His Thr Val Asn Leu Ser Arg Asn Glu Leu Thr Ala Phe Pro
305                 310                 315                 320

Ala Gly Gly Pro Gln Gln Phe Val Ser Thr Val Thr Ile Asn Met Glu
                325                 330                 335

His Asn Gln Ile Ser Lys Ile Pro Ile Gly Ile Phe Ser Lys Ala Thr
            340                 345                 350

Arg Leu Thr Lys Leu Asn Leu Lys Glu Asn Glu Leu Val Ser Leu Pro
        355                 360                 365

Leu Asp Met Gly Ser Trp Thr Ser Ile Thr Glu Leu Asn Leu Ser Thr
    370                 375                 380

Asn Gln Leu Lys Val Leu Pro Glu Asp Ile Glu Lys Leu Val Asn Leu
385                 390                 395                 400

Glu Ile Leu Val Leu Ser Asn Asn Gln Leu Lys Lys Leu Pro Asn Gln
                405                 410                 415

Ile Gly Asn Leu Asn Lys Leu Arg Glu Leu Asp Leu Glu Glu Asn Glu
            420                 425                 430

Leu Glu Thr Val Pro Thr Glu Ile Gly Phe Leu Gln His Leu Thr Lys
        435                 440                 445

Leu Trp Val Gln Ser Asn Lys Ile Leu Thr Leu Pro Arg Ser Ile Gly
    450                 455                 460

Asn Leu Cys Ser Leu Gln Asp Leu Arg Leu Gly Glu Asn Leu Thr
465                 470                 475                 480

Ala Ile Pro Glu Glu Ile Gly His Leu Asp Ser Leu Lys Ser Leu Tyr
                485                 490                 495

Leu Asn Asp Asn Ser Ser Leu His Asn Leu Pro Phe Glu Leu Ala Leu
            500                 505                 510

Cys Gln Ser Leu Glu Ile Met Ser Ile Glu Asn Ser Pro Leu Ser Gln
        515                 520                 525

Ile Pro Pro Glu Ile Thr Ala Gly Gly Pro Ser Leu Val Ile Gln Tyr
    530                 535                 540

Leu Lys Met Gln Gly Pro Tyr Arg Gly Val Val Met Asn Ser Gln
545                 550                 555
```

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic

<400> SEQUENCE: 3
tggtagaaaa ctgagctgga ccaccc                                           26

<210> SEQ ID NO 4
<211> LENGTH: 26
<212> TYPE: DNA
<213> ORGANISM: Artificial Sequence
<220> FEATURE:

<223> OTHER INFORMATION: Description of Artificial Sequence: Synthetic

<400> SEQUENCE: 4
gggatctttg tgagctgatt agtcgc                                          26

<210> SEQ ID NO 5
<211> LENGTH: 1749
<212> TYPE: DNA
<213> ORGANISM: Mus musculus
<220> FEATURE:
<223> OTHER INFORMATION: The N at location 30 can be A, C, T, or G.
<220> FEATURE:
<223> OTHER INFORMATION: The N at location 90 can be A, C, T, or G.

<400> SEQUENCE: 5

| | |
|---|---|
| atgagtagta gtttaggaaa agaaaaagan tttaaagaga aagaccccaa agtaccgtct | 60 |
| gccaaggaaa gagaaaagga gtcaaaagcn tcaggaggct ttgggaaaga gagcaaagaa | 120 |
| aaggaaccta agccaaagg gaaagacgcc aaagatggaa agaaggagtc cagcgctgcc | 180 |
| cagccaggtg tggcttttc agtcgacaat accatcaaac ggccaaatcc agcacccggc | 240 |
| actagaaaaa agtccagcaa tgctgaggtc attaaggagc ttaacaaatg ccgggaggag | 300 |
| aactcaatgc ggttggactt gtccaagagg tctatacata tactgccacc atcagtcaaa | 360 |
| gagttgactc aactcacaga actttattta tacagtaaca aattgcagtc cctcccagca | 420 |
| gaggtgggct gtctagtcaa tctcatgacg ctggctctca gtgagaattc actcaccagt | 480 |
| ttgcctgact ctcttgataa cttgaagaag ctgcggatgc ttgatttacg cataataaaa | 540 |
| ctgagagaaa ttccttcagt ggtgtatagg ctagactctc tcaccactct ctatcttcgc | 600 |
| tttaatcgca taactactgt ggaaaaggac atcaaaaacc tgccgaagct cagcatgctc | 660 |
| agcatccgag agaacaaaat caagcagctg cctgctgaaa ttggtgaatt atgtaacctc | 720 |
| attccctgg atgtagctca caatcaactt gaacaccttc caaggagat tggaaactgc | 780 |
| acacagataa ccaaccttga cttgcagcac aatgacctac tggacctccc agatacaata | 840 |
| ggaaacctgt ccagtttaaa tcgccttggc ctgagataca atagattgtc agcaataccc | 900 |
| agatcattag caaaatgcag tgcacttgag gagttaaatt tagagaacaa taacattct | 960 |
| actctaccag agagtctttt atccagtctt gtaaaattga atagcttgac cttagctaga | 1020 |
| aattgcttcc agttatatcc agtgggaggt ccatctcagt tttccaccat ttattccctc | 1080 |
| aacatggaac acaatcgaat caacaaaatc ccatttggaa ttttttccag agctaaagtg | 1140 |
| ttaagtaagc tgaatatgaa ggacaatcag ttaacatcac ttcctttgga ttttggaact | 1200 |
| tggaccagta tggtagaatt gaatttagcg actaatcagc tcacaaagat cccagaggat | 1260 |
| gtgtctggtc tcgtttccct tgaggttctg atcttatcga caaccttct aaagaagctg | 1320 |
| ccccacggcc ttgggaacct cagaaagcta cgagagctgg acctggagga gaacaagctg | 1380 |
| gagtccttgc ccaatgagat cgcgtatctc aaggatctgc agaaattagt cttgacaaac | 1440 |
| aaccagttga gcacgcttcc cagaggcatc ggtcacctta ccaacctcac gcaccttggt | 1500 |
| cttggagaga acctgctcac tcaccttcct gaggaaatcg gtacactgga aaacctagaa | 1560 |
| gaactgtatt tgaacgacaa ccccaacctt cacagcctcc cctttgagct tgctctctgc | 1620 |
| agcaagctgt caatcatgag tattgagaac tgtccactca gtcacctccc acctcaaatt | 1680 |
| gttgctggag ggccttcgtt cattattcag ttcttaaaga tgcagggtcc atatcgtgcc | 1740 |
| atggtctga | 1749 |

-continued

```
<210> SEQ ID NO 6
<211> LENGTH: 1749
<212> TYPE: DNA
<213> ORGANISM: Homo sapiens

<400> SEQUENCE: 6
atgagtagta gtttaggaaa agaaaaagac tctaaagaaa aagatcccaa agtaccatca      60
gccaaggaaa gagaaaagga ggcaaaagcc tctggaggtt ttgggaaaga gagcaaagaa     120
aaagaaccta agaccaaagg gaaagatgcc aaagatggaa agaaggactc cagtgctgcc     180
caaccagggg tggcattttc agttgacaat acgatcaaac ggccaaaccc agcacctggg     240
actagaaaaa aatccagcaa tgcagaggtg attaaagagc tcaacaaatg ccgggaagag     300
aattcaatgc gtttggactt atccaagaga tctatacaca tattgccatc atcaatcaaa     360
gagttgactc aattaacaga actttattta tacagtaaca aattgcagtc cctcccagca     420
gaggtgggat gtttagtaaa tctcatgaca ctggctctaa gtgaaaattc acttaccagt     480
ttgcctgact ctcttgataa cttgaagaag ctgcggatgc ttgatttacg cataataaaa     540
ctgagagaaa ttccttcagt ggtgtatagg ctggattctc tcaccactct ttaccttcgc     600
tttaatcgta taactactgt ggaaaaggac atcaaaaact tgtcaaaact cagcatgctt     660
agcattcgag agaacaaaat taaacaacta cctgctgaaa ttggtgaatt atgtaacctc     720
attacgctgg atgtagctca caatcaactt gaacaccttc caaggagat tggaaactgt     780
acacagataa ccaaccttga cttgcagcac aatgaactgc tagacctccc agatactata     840
ggaaacctgt ccagtttaag tcgtcttggt ctgagatata cagactgtc agcaataccc     900
agatcattag caaaatgcag tgcacttgaa gaattaaatt tagagaacaa taacatttct     960
actttaccag agagtctttt atcaagtctt gtgaaactga atagtttgac cttagctaga    1020
aattgcttcc agttgtatcc agtgggtggt ccatctcagt tttctaccat ctattccctc    1080
aacatggaac acaatcgaat caacaaaatt ccatttggaa ttttctccag agcaaaagta    1140
ttaagtaagc tgaatatgaa ggacaatcag ttaacatcac ttcccttgga ttttggaact    1200
tggaccagta tggtagaatt gaatttagcc actaatcagc tcacaaagat ccctgaggat    1260
gtgtctggtc tcgtttctct tgaggttctt atcttatcaa acaatcttct aaagaagctt    1320
ccccatggtc ttgaaaacct taggaagtta agagagttgg atctagaaga gaacaaattg    1380
gaatccttgc caaatgaaat tgcatatctt aaggatttac agaaattagt cttgacaaac    1440
aaccagttga ccactcttcc cagaggcatt ggtcacctta ctaatctcac acatctgggc    1500
cttggagaga acctacttac tcaccttcct gaagaaattg gtacactgga aacctagaa    1560
gaactgtatt tgaatgacaa ccccaacctg catagccttc cctttgagct ggcactctgc    1620
agcaagcttt caatcatgag tattgagaac tgtccactca gtcaccttcc acctcagatt    1680
gttgctgggg ggccttcttt catcattcag ttcttaaaga tgcagggtcc atatcgtgcc    1740
atggtctga                                                            1749

<210> SEQ ID NO 7
<211> LENGTH: 582
<212> TYPE: PRT
<213> ORGANISM: Mus musculus
<220> FEATURE:
<223> OTHER INFORMATION: Xaa at position 10 can be any amino acid.

<400> SEQUENCE: 7

Met Ser Ser Ser Leu Gly Lys Glu Lys Xaa Phe Lys Glu Lys Asp Pro
  1               5                  10                  15
```

-continued

```
Lys Val Pro Ser Ala Lys Glu Arg Glu Lys Glu Ser Lys Ala Ser Gly
             20                  25                  30
Gly Phe Gly Lys Glu Ser Lys Glu Lys Glu Pro Lys Ala Lys Gly Lys
         35                  40                  45
Asp Ala Lys Asp Gly Lys Lys Glu Ser Ser Ala Ala Gln Pro Gly Val
         50                  55                  60
Ala Phe Ser Val Asp Asn Thr Ile Lys Arg Pro Asn Pro Ala Pro Gly
 65                  70                  75                  80
Thr Arg Lys Lys Ser Ser Asn Ala Glu Val Ile Lys Glu Leu Asn Lys
                 85                  90                  95
Cys Arg Glu Glu Asn Ser Met Arg Leu Asp Leu Ser Lys Arg Ser Ile
            100                 105                 110
His Ile Leu Pro Pro Ser Val Lys Glu Leu Thr Gln Leu Thr Glu Leu
            115                 120                 125
Tyr Leu Tyr Ser Asn Lys Leu Gln Ser Leu Pro Ala Glu Val Gly Cys
            130                 135                 140
Leu Val Asn Leu Met Thr Leu Ala Leu Ser Glu Asn Ser Leu Thr Ser
145                 150                 155                 160
Leu Pro Asp Ser Leu Asp Asn Leu Lys Lys Leu Arg Met Leu Asp Leu
                165                 170                 175
Arg His Asn Lys Leu Arg Glu Ile Pro Ser Val Val Tyr Arg Leu Asp
            180                 185                 190
Ser Leu Thr Thr Leu Tyr Leu Arg Phe Asn Arg Ile Thr Thr Val Glu
            195                 200                 205
Lys Asp Ile Lys Asn Leu Pro Lys Leu Ser Met Leu Ser Ile Arg Glu
            210                 215                 220
Asn Lys Ile Lys Gln Leu Pro Ala Glu Ile Gly Glu Leu Cys Asn Leu
225                 230                 235                 240
Ile Thr Leu Asp Val Ala His Asn Gln Leu Glu His Leu Pro Lys Glu
                245                 250                 255
Ile Gly Asn Cys Thr Gln Ile Thr Asn Leu Asp Leu Gln His Asn Asp
            260                 265                 270
Leu Leu Asp Leu Pro Asp Thr Ile Gly Asn Leu Ser Ser Leu Asn Arg
            275                 280                 285
Leu Gly Leu Arg Tyr Asn Arg Leu Ser Ala Ile Pro Arg Ser Leu Ala
            290                 295                 300
Lys Cys Ser Ala Leu Glu Glu Leu Asn Leu Glu Asn Asn Asn Ile Ser
305                 310                 315                 320
Thr Leu Pro Glu Ser Leu Leu Ser Ser Leu Val Lys Leu Asn Ser Leu
                325                 330                 335
Thr Leu Ala Arg Asn Cys Phe Gln Leu Tyr Pro Val Gly Gly Pro Ser
            340                 345                 350
Gln Phe Ser Thr Ile Tyr Ser Leu Asn Met Glu His Asn Arg Ile Asn
            355                 360                 365
Lys Ile Pro Phe Gly Ile Phe Ser Arg Ala Lys Val Leu Ser Lys Leu
            370                 375                 380
Asn Met Lys Asp Asn Gln Leu Thr Ser Leu Pro Leu Asp Phe Gly Thr
385                 390                 395                 400
Trp Thr Ser Met Val Glu Leu Asn Leu Ala Thr Asn Gln Leu Thr Lys
                405                 410                 415
Ile Pro Glu Asp Val Ser Gly Leu Val Ser Leu Glu Val Leu Ile Leu
            420                 425                 430
```

```
Ser Asn Asn Leu Leu Lys Lys Leu Pro His Gly Leu Gly Asn Leu Arg
        435                 440                 445

Lys Leu Arg Glu Leu Asp Leu Glu Glu Asn Lys Leu Glu Ser Leu Pro
    450                 455                 460

Asn Glu Ile Ala Tyr Leu Lys Asp Leu Gln Lys Leu Val Leu Thr Asn
465                 470                 475                 480

Asn Gln Leu Ser Thr Leu Pro Arg Gly Ile Gly His Leu Thr Asn Leu
                485                 490                 495

Thr His Leu Gly Leu Gly Glu Asn Leu Leu Thr His Leu Pro Glu Glu
            500                 505                 510

Ile Gly Thr Leu Glu Asn Leu Glu Glu Leu Tyr Leu Asn Asp Asn Pro
        515                 520                 525

Asn Leu His Ser Leu Pro Phe Glu Leu Ala Leu Cys Ser Lys Leu Ser
    530                 535                 540

Ile Met Ser Ile Glu Asn Cys Pro Leu Ser His Leu Pro Pro Gln Ile
545                 550                 555                 560

Val Ala Gly Gly Pro Ser Phe Ile Ile Gln Phe Leu Lys Met Gln Gly
                565                 570                 575

Pro Tyr Arg Ala Met Val
            580

<210> SEQ ID NO 8
<211> LENGTH: 582
<212> TYPE: PRT
<213> ORGANISM: Homo sapiens

<400> SEQUENCE: 8

Met Ser Ser Ser Leu Gly Lys Glu Lys Asp Ser Lys Glu Lys Asp Pro
1               5                   10                  15

Lys Val Pro Ser Ala Lys Glu Arg Glu Lys Glu Ala Lys Ala Ser Gly
            20                  25                  30

Gly Phe Gly Lys Glu Ser Lys Glu Lys Glu Pro Lys Thr Lys Gly Lys
        35                  40                  45

Asp Ala Lys Asp Gly Lys Lys Asp Ser Ser Ala Ala Gln Pro Gly Val
    50                  55                  60

Ala Phe Ser Val Asp Asn Thr Ile Lys Arg Pro Asn Pro Ala Pro Gly
65                  70                  75                  80

Thr Arg Lys Lys Ser Ser Asn Ala Glu Val Ile Lys Glu Leu Asn Lys
                85                  90                  95

Cys Arg Glu Glu Asn Ser Met Arg Leu Asp Leu Ser Lys Arg Ser Ile
                100                 105                 110

His Ile Leu Pro Ser Ser Ile Lys Glu Leu Thr Gln Leu Thr Glu Leu
            115                 120                 125

Tyr Leu Tyr Ser Asn Lys Leu Gln Ser Leu Pro Ala Glu Val Gly Cys
    130                 135                 140

Leu Val Asn Leu Met Thr Leu Ala Leu Ser Glu Asn Ser Leu Thr Ser
145                 150                 155                 160

Leu Pro Asp Ser Leu Asp Asn Leu Lys Lys Leu Arg Met Leu Asp Leu
                165                 170                 175

Arg His Asn Lys Leu Arg Glu Ile Pro Ser Val Val Tyr Arg Leu Asp
            180                 185                 190

Ser Leu Thr Thr Leu Tyr Leu Arg Phe Asn Arg Ile Thr Thr Val Glu
        195                 200                 205

Lys Asp Ile Lys Asn Leu Ser Lys Leu Ser Met Leu Ser Ile Arg Glu
    210                 215                 220
```

```
Asn Lys Ile Lys Gln Leu Pro Ala Glu Ile Gly Glu Leu Cys Asn Leu
225                 230                 235                 240

Ile Thr Leu Asp Val Ala His Asn Gln Leu Glu His Leu Pro Lys Glu
            245                 250                 255

Ile Gly Asn Cys Thr Gln Ile Thr Asn Leu Asp Leu Gln His Asn Glu
            260                 265                 270

Leu Leu Asp Leu Pro Asp Thr Ile Gly Asn Leu Ser Ser Leu Ser Arg
            275                 280                 285

Leu Gly Leu Arg Tyr Asn Arg Leu Ser Ala Ile Pro Arg Ser Leu Ala
            290                 295                 300

Lys Cys Ser Ala Leu Glu Glu Leu Asn Leu Glu Asn Asn Ile Ser
305                 310                 315                 320

Thr Leu Pro Glu Ser Leu Leu Ser Ser Leu Val Lys Leu Asn Ser Leu
                325                 330                 335

Thr Leu Ala Arg Asn Cys Phe Gln Leu Tyr Pro Val Gly Gly Pro Ser
                340                 345                 350

Gln Phe Ser Thr Ile Tyr Ser Leu Asn Met Glu His Asn Arg Ile Asn
            355                 360                 365

Lys Ile Pro Phe Gly Ile Phe Ser Arg Ala Lys Val Leu Ser Lys Leu
            370                 375                 380

Asn Met Lys Asp Asn Gln Leu Thr Ser Leu Pro Leu Asp Phe Gly Thr
385                 390                 395                 400

Trp Thr Ser Met Val Glu Leu Asn Leu Ala Thr Asn Gln Leu Thr Lys
                405                 410                 415

Ile Pro Glu Asp Val Ser Gly Leu Val Ser Leu Glu Val Leu Ile Leu
                420                 425                 430

Ser Asn Asn Leu Leu Lys Lys Leu Pro His Gly Leu Gly Asn Leu Arg
            435                 440                 445

Lys Leu Arg Glu Leu Asp Leu Glu Glu Asn Lys Leu Glu Ser Leu Pro
450                 455                 460

Asn Glu Ile Ala Tyr Leu Lys Asp Leu Gln Lys Leu Val Leu Thr Asn
465                 470                 475                 480

Asn Gln Leu Thr Thr Leu Pro Arg Gly Ile Gly His Leu Thr Asn Leu
                485                 490                 495

Thr His Leu Gly Leu Gly Glu Asn Leu Leu Thr His Leu Pro Glu Glu
                500                 505                 510

Ile Gly Thr Leu Glu Asn Leu Glu Glu Leu Tyr Leu Asn Asp Asn Pro
            515                 520                 525

Asn Leu His Ser Leu Pro Phe Glu Leu Ala Leu Cys Ser Lys Leu Ser
            530                 535                 540

Ile Met Ser Ile Glu Asn Cys Pro Leu Ser His Leu Pro Pro Gln Ile
545                 550                 555                 560

Val Ala Gly Gly Pro Ser Phe Ile Ile Gln Phe Leu Lys Met Gln Gly
                565                 570                 575

Pro Tyr Arg Ala Met Val
            580

<210> SEQ ID NO 9
<211> LENGTH: 7183
<212> TYPE: DNA
<213> ORGANISM: Caenorhabditis elegans

<400> SEQUENCE: 9
ggatcctatt gaagtgggtg ttttcgttgc atatttcaac atattttaat tgaaagtgtg    60
```

-continued

```
gcttatttct tgttgacagc cctattttaa aactaaatat cactaaaatt ataatgtttg      120
gtgaaaattg ttccaaaaag tcacaagttc gtgttttcat ggcacatttc aagcaacttt      180
taatatattt tttttccaga ctaccgagga aaaacttttta tttaaaaata cactgttgag     240
aatggtatat ttccatcata atttttacct accaaacgta ttgaaactgt ggaaaagtct      300
gtggaaaaaa tgccgaattt ccaaattaaa tgtgactttt tgtgaaaatt caagacgtta      360
tcgaagccat gtttgaaaaa agtttgcata tctaatatta tttttgagaa aacttgaagt      420
ttataaaact gttagattag ttgaaaacta accgtttcga aaattcaata atgaaatatc      480
tgttttcagg ttttcatttc ctctagttgc tcatttcaat atattttaat atcaaattct      540 actgaaagt atgtgtcatt tcttgttgac accactattt tcaaactaaa taataccac        600 gataattata tattttgcaa aaattgttca aaagtatca agttttctcg ttcttggcat        660
atttcatgca atttgtaatt cttttttgtct cagttatgtc ataacttttt ctaaaaatcc     720
taagttattc tagattattt gggagcaaac attttttagaa attcccaaag tagattaaca     780
aagaaaattc aaatataaat ctactggaca ttcaaagaaa agcacttaga caatttgaat      840
cgaattcctc aaaattcttga actatttttt agaggatttc aattggacag aaagaatctc     900
aagcacttaa cgtcggcgga aatagttttt tttttttcaaa aagagaccac cgcctttgct    960
agaaacgaaa attgcatgcg ttccattaaa taattcaatt catcgttatc accatccttc     1020
gtcgtcgtcg ttatcgtcag aaacagatag ggatgggtcg atacaaaaag aaagtggaca     1080 gttctttttct ctcactcttt ttctctttta caaatcacac ttgtttcgtc tcacacacgc    1140
tcacttcttg tctcttctcc caacagtcgt cgcaaaaccg tcaaaagcgt agcggctgtc     1200
gcgtcgcggt cgttcgtgtc tatgcatcac cgtttctagt gctctctaat tgtcccgccg     1260
tagcagtagc agcagtagca gcggcatggt ggggaccgca ctcctttatc ttttactctt     1320
actttgtgtg tgtgtatggg gggtgcgaga gaaagagata aaaagaaag aaagagagag      1380 tgtgtggttt ctgtgcttct gtgcactcca gagcctcgga tttctttttcc tatgaacttc    1440 atttctcgtc tccatcatca gaaggaagaa gaattcttca gaatcttgca cttgaagcgt     1500
tttctgccta tttattttct cctcccgagt tcatctctct attcgtcttt agcttaatcc     1560
attttattag gcacgcaccc gctccttggt tcaaccaaat gagaagatag aaaagatgga     1620
gcaacgcatc ccaaattgtg tgataggatt aaagtagtgt ggaagaaaaa aaaatgcaga     1680
gtgagagaag gggcagtctt ctttttccggt cttactaatc ctaacgtctt cttttttcctt   1740 cctatctctc atctctcaac ttctgaaata gttgagatga gtgatttcgt aagttcatta     1800
ttcttttttg tcagttttttg cttatagttc ctacgggaat cattgtttct taaacatgct    1860
acttctttaa acaatttata tttaacaaag taaaattgaa cgttttttta aaactttct     1920 aactgaattt cgtaaattta tttgtttcct tgtgaaaaat gcttgtcagg aaaacttttac    1980 ttctctacgt ctcaatctct gcaatctttt aacgagagat cggagaattt tgtattggaa     2040
aagtgaaaaa gaaaaatgaa agagacccac tcgacactga gggcgaccga aaagaaaccg     2100
acgaaaaaaa acgacgattc gagccatttg tcagcgacaa taagtggtcg ggtcgcacca     2160
ctgtccgccg tctcaccgat tttaacatta tattgtcccc cttttttcttc atcgctttga    2220 aatcaatttt tgatgaagtg aagacctttt ttctcctggt ttttttttta ataattgcat     2280 tacccccattt tttaaagttc aaaattactc aaactatttg aattcttctt tttttcaaat    2340
tgtaatgact cattctccgt cgtcttcaaa tagttactca ttccgactca ccacctagtt     2400
```

-continued

```
tattaacagg aaagttcatt cttttttctat cttctcaatt attctcaagt agtcatcatc   2460
ggttttttat ttctttcctg gtagttactc tcctttatcg aaactttttt ttgaaaaaaa   2520
aaagaaacgg aattctgagt atgccgatag gcagagctgc tctttggcag tgctcccaca   2580
gaaatccttc tccacttcgt tttctcattt ccatctctat tttacatttt tccatattca   2640
actatgcgtc ttttttcaga aaagggtaat gacggagtac aagcttgtgg tagttgaaga   2700
tggaggagtt ggtaaatcag cactcaccat tcaactcatc cagaatcact ttgtcgaaga   2760
atacgacccg accatagagg acagctacag aaagcaggtg agaaatcatt gggaacatcc   2820
gctacacaca tgtggtggga gcaaattgaa cgaaaatgat ggcatttgaa attgaacaaa   2880
aaaacgatga gtcagaagtt tggaagtttt ttgaaacaca tcgagctgtt taattgattc   2940
caaagacgaa taaatcgtgc tgaaacacga aaattccga aattttcgaa aaaaaccaa     3000 tttttcgtgt tttggacacg acattataaa atggctggaa ctgaaaaaaa tggctcgaat   3060
catgattttt cattgtcccc cgaaaattct cacaaaaaaa aattggaaaa ccgaaaattt   3120 tagttttgc aaaaaccgga aaaattctga aaacactcca aaatcgatat ttctcagacg    3180
aatttcaata attacattcc gttttacgtt ttatacaaaa aacagaaatt tcactttttt   3240
tttgagaaag ggcccaaaac tttttttttag attttttgtt tttttaaagc aaatcgataa   3300
accagcatgc ctgctcgtgt cgtgtgagga gtataaattt ttttaaacgt atattcatct   3360
ttaaactctg aaattcagaa tattattgag ccctaatttt cagtgttttc atttgagttt   3420
ttaaccagta aaaatagttt ttcagtttta aaaattgctc cgagagctag ttttttaaata  3480 ttctaatttc aggttgtgat agacggtgag acatgcctcc tcgacatatt ggataccgcc   3540
ggacaagaag aatattcggc gatgcgtgat cagtacatga ggacaggcga aggatttctg   3600
ttggttttcg ccgtcaacga ggctaaatct ttcgagaatg tcgctaacta ccgcgagcag   3660
attcggaggg taaaggattc agatgatgtg agttttttttt gttgaaatta tcagtcaatg   3720
gttgaatatt tgtatttctt ctaggttcct atggtcttgg tagggaataa atgtgatttg   3780
tcatctcgat cagtcgactt ccgaacagtc agtgagacag caaagggtta cggtattccg   3840
aatgtcgaca catctgccaa aacgcgtatg ggagttgatg aagcatttta cacacttgtt   3900
agagaaattc gcaaggtaat ttttttagtta aaaatttaaa ttaaaaataa tgttttttaat  3960 gtacaattaa ggtacaaatt cagtcattat tatatgaaaa ttgaaagacg cgagattttg   4020
atattttcgc gccaaaaata cgacacccgg tctgttcgat ttgctccttc aaatattatg   4080
gtaactttat actgtcgtta cagcggaatt ttcatcaatt tttttaagtt ttcgatatta   4140
taaaaatatt taaaaacaca gcagttttaa taaatcggtg aaaattaccc cagaaacgaa   4200
atattaaagt tactgtattc tttaaaggcg cacatacgtt tgcatttaac acaaattcat   4260
cgtgtcgaga ccgggcaccg catctttaat ttgaaaatcg ccaaatgttg catttgagta   4320
atacaaaaac gttgtttta aaattttct gttttgtaaa gctctaaaat gttattattg    4380
ttatcaacag tttcaagttt ccatttttca ctaaaaacga aaaatgtaag tttttccgat   4440
atttcgaaac aaaagctcaa agttttggtc attttcttaa ttttttaaaga aaattatatg   4500 ttttcttttg tttttttttct caccagcatg cacaaaatct gataaaaaat tgagttttat   4560
tgttaatttt ctaaaaaaaa ttttgatgac accctagatt gatatccgaa agatttaata   4620 atgtttctt tttatttcag catcgtgagc gtcacgacaa taataagcca caaagaaga     4680 agaagtgtca aataatgtga ttcagcgtcg ggaattgccc aatttcgcca actcattttc   4740
agtcgtgtca actcccaccc aattatcctt tctcgtactt ttttggtaca ttttcattat   4800
```

```
tcatttatct gttttatctg aaacttgtga tcgatcctct tccgcctcta catactcttc    4860
gaatttccac cttttttttct ctatgcatcg attgaacttg ttctctcgtc tgctcgtcat   4920 tatttttttct cctttttttt cttcatcctt cattctaatt cctcatcttt cgcttagccc   4980
aaatctccat tcattcatag gtgtcaaaac tagctgtagt gtgtgatcca tatctaaaac    5040
atgcatccga acccctcct cgttccaaaa ttggccaact ctaccaaaaa aaacatcgca    5100
ccattttttt ttcactttct ctgcatattt tcagaatgtt tgtattgctt ttttgatgct    5160 ttattccct tcctcgtttt catacaaatt attggcctca tctattttca gaagttctct    5220
gaaaattaaa ttcttttgca tctgccggtc gttccgttta tttttttctct gtttcctctc   5280 atttttgtca agtaattatt tctctttcat taactataat atagatacaa ttagaccca     5340 tttctcatac atttttctgaa catctgaaag tttttgctcc ctcgtattgc attcatttttt  5400 ctctattcct ctacattttta tagtcctatc tgaatataat attcctattc ttttgatcaa   5460 gttttttatta ttattttatt ttcaaggaag tattgcaatg atataaattt taaaaagcta   5520
atattatttt tttaaatcta ttcaactata ttttgttaat ttcagtgtta tattttgacc    5580
tcgccatcgg agcatgattt taaaaaaac taaatttaat ttattagaat gacgagaaaa    5640
aggaaaaatg tagagtctga tgagaatcct ccagcgaaaa actcatttga aggatacgga    5700
tatgctgctg ctgatgctga aagaagcca caggaggaga gaaacaattt cagaacttttt   5760 ctagccaaaa atgaacgatt tggaagtgga aatcgaggtg gaggaggtcg tggaagagga   5820
ggagatggtg gatttagaag aaatgataga ggtggacgtg gtggtggtgg aagaggattc   5880
ggtggtaaca gagaattcag tgccggagat tttgagaagg tttgtgtcag atggtgtcgt   5940
gagtgatgta gcgtctctgg ctttttaaac tcaaaattac agaaaaagtt tcgatatgtc   6000
gagttaaaaa catttctaaa atttgtatta ttttgcaaaa aataaaaaaa agccgaatta   6060
tttttgaatt ttttagtcat tttcctggac aaaaattgtt caaatgtgg aattataggt    6120 tttagaccaa tttcatttta tcgaatttcg ttcggatttt cgaggtttct ttccgaaaaa   6180
ctgtctgaaa aaatgagcgc gggaattcac aaatatttca gtatttttttt gaaattgaat   6240 tttaaaaaat ttatattcga tatattgaga cttttttctg tgaagaatcg ataaaatgaa   6300
ctccaaagcg ctccctaggc aattaccaca aaaacgtata tatttattta atttacagca   6360
atacggtcga gttggcggcg gtgatgcacg gaattcagga caaccggata gctacggaca   6420
agctgattcg gcttcattca acgactctcg accagatgga gatggtcgtg aatttccgaa   6480
agaaattgtt ggttatctga gaagtattga acaaatcaag aagaaagagg gaaaattga    6540 agattttatt ctggaaaagt gtgctgaaga agttgttggc caggagaaaa ctcttctctc   6600
gtggacagaa gcagccgttg ttgttgaatc tgtatttgga agttgtccta aaggagcagc   6660
tctcttcctt tcatcgattt tcgtctcaa gcataaaaca ttagctgagc tgatttttcgg   6720 aggagctagt gctaggacaa ttgaaaattt gatattctcg atgtgcccaa tcgccgaatc   6780
agaacatgtg gagattcttc aaaaactagc aggaattctt atggataact gggcggatgc   6840
tgttacaaca caaccttcga gttttctgat tcgagctatt gtctgggtgt gttgtggatt   6900
gtcagcaagg ccaaaggttg gagaggaaaa gaaagaaat tacaaaggac aagaaatgaa   6960
ggctagcttg aagaatgttt atgaaaaact tgcaatcttg gcattcgatg agaatcttaa    7020 taaaacctttt atggattctc cgattttgt gacactatttt caagattttta ttgaagccga   7080 tgggctttgg ggagacaaaa gaggtgatga atatgtgaag aagaagctcg aaaaggaaga   7140
```

-continued

```
tattgaagga atctcgaagg catggtattc atcaaatgga tct              7183
```

<210> SEQ ID NO 10
<211> LENGTH: 7183
<212> TYPE: DNA
<213> ORGANISM: Artificial Sequence
<220> FEATURE:
<223> OTHER INFORMATION: Description of Artificial Sequence: Synthetic

<400> SEQUENCE: 10

```
ggatcctatt gaagtgggtg ttttcgttgc atatttcaac atattttaat tgaaagtgtg     60
gcttatttct tgttgacagc cctattttaa aactaaatat cactaaaatt ataatgtttg    120
gtgaaaattg ttccaaaaag tcacaagttc gtgttttcat ggcacatttc aagcaacttt    180
taatatattt tttttccaga ctaccgagga aaaacttttta tttaaaaata cactgttgag   240
aatggtatat ttccatcata attttttacct accaaacgta ttgaaactgt ggaaaagtct   300
gtggaaaaaa tgccgaattt ccaaattaaa tgtgacttt tgtgaaaatt caagacgtta    360
tcgaagccat gtttgaaaaa gtttgcata tctaatatta tttttgagaa aacttgaagt    420
ttataaaact gttagattag ttgaaaacta accgtttcga aaattcaata atgaaatatc    480
tgttttcagg ttttcatttc ctctagttgc tcatttcaat atattttaat atcaaattct    540
actggaaagt atgtgtcatt tcttgttgac accactattt tcaaactaaa taataccac    600
gataattata tattttgcaa aaattgttca aaaagtatca agttttctcg ttcttggcat    660
atttcatgca atttgtaatt ctttttgtct cagttatgtc ataactttt ctaaaaatcc    720
taagttattc tagattattt gggagcaaac attttttagaa attcccaaag tagattaaca    780
aagaaaattc aaatataaat ctactggaca ttcaaagaaa agcacttaga caatttgaat    840
cgaattcctc aaattcttga actattttt agaggattc aattggacag aaagaatctc     900
aagcacttaa cgtcggcgga aatagttttt tttttcaaa aagagaccac cgcctttgct    960
agaaacgaaa attgcatgcg ttccattaaa taattcaatt catcgttatc accatccttc   1020
gtcgtcgtcg ttatcgtcag aaacagatag ggatgggtcg atacaaaaag aaagtggaca   1080
gttcttttct ctcactcttt ttctctttta caaatcacac ttgtttcgtc tcacacacgc   1140
tcacttcttg tctcttctcc caacagtcgt cgcaaaaccg tcaaaagcgt agcggctgtc   1200
gcgtcgcggt cgttcgtgtc tatgcatcac cgtttctagt gctctctaat tgtcccgccg   1260
tagcagtagc agcagtagca gcggcatggt ggggaccgca ctcctttatc ttttactctt   1320
actttgtgtg tgtgtatggg gggtgcgaga gaaagagata aaaagaaag aaagagagag    1380
tgtgtggttt ctgtgcttct gtgcactcca gagcctcgga tttcttttcc tatgaacttc   1440
atttctcgtc tccatcatca gaaggaagaa gaattcttca gaatcttgca cttgaagcgt   1500
tttctgccta tttattttct cctcccgagt tcatctctct attcgtcttt agcttaatcc   1560
attttattag gcacgcaccc gctccttggt tcaaccaaat gagaagatag aaaagatgga   1620
gcaacgcatc ccaaattgtg tgataggatt aaagtagtgt ggaagaaaaa aaatgcaga    1680
gtgagagaag gggcagtctt cttttccggt cttactaatc ctaacgtctt ctttttcctt   1740
cctatctctc atctctcaac ttctgaaata gttgagatga gtgatttcgt aagttcatta   1800
ttcttttttg tcagttttg cttatagttc ctacgggaat cattgtttct taaacatgct    1860
acttctttaa acaatttata tttaacaaag taaaattgaa cgtttttta aaactttct     1920
aactgaattt cgtaaattta tttgtttcct tgtgaaaaat gcttgtcagg aaaactttac   1980
ttctctacgt ctcaatctct gcaatctttt aacgagagat cggagaattt tgtattggaa   2040
```

-continued

```
aagtgaaaaa gaaaatgaa agagacccac tcgacactga gggcgaccga aagaaaccg      2100 acgaaaaaaa acgacgattc gagccatttg tcagcgacaa taagtggtcg ggtcgcacca      2160
ctgtccgccg tctcaccgat tttaacatta tattgtcccc cttttcttc atcgctttga       2220 aatcaatttt tgatgaagtg aagacctttt ttctcctggt ttttttttta ataattgcat      2280
taccccattt tttaaagttc aaaattactc aaactatttg aattcttctt tttttcaaat     2340
tgtaatgact cattctccgt cgtcttcaaa tagttactca ttccgactca ccacctagtt      2400
tattaacagg aaagttcatt cttttctat cttctcaatt attctcaagt agtcatcatc       2460
ggttttttat ttctttcctg gtagttactc tcctttatcg aaactttttt ttgaaaaaaa     2520
aaagaaacgg aattctgagt atgccgatag gcagagctgc tctttggcag tgctcccaca    2580
gaaatccttc tccacttcgt tttctcattt ccatctctat tttacatttt tccatattca     2640
actatgcgtc ttttttcaga aagggtaat gacggagtac aagcttgtgg tagttgaaga      2700
tggaggagtt ggtaaatcag cactcaccat tcaactcatc cagaatcact ttgtcgaaga      2760 atcgacccg accatagagg acagctacag aaagcaggtg agaaatcatt gggaacatcc      2820
gctacacaca tgtggtggga gcaaattgaa cgaaaatgat ggcatttgaa attgaacaaa    2880
aaaacgatga gtcagaagtt tggaagtttt ttgaaacaca tcgagctgtt taattgattc      2940
caaagacgaa taaatcgtgc tgaaacacga aaaattccga aattttcgaa aaaaaccaa       3000 ttttcgtgt tttggacacg acattataaa atggctggaa ctgaaaaaaaa tggctcgaat    3060 catgatttt cattgtcccc cgaaaattct cacaaaaaa aattggaaaa ccgaaaattt      3120 tagttttgc aaaaaccgga aaaattctga aaacactcca aaatcgatat ttctcagacg       3180
aatttcaata attcattcc gttttacgtt ttatacaaaa aacagaaatt tcacttttttt    3240 tttgagaaag ggcccaaaac ttttttttag atttttttgtt tttttaaagc aaatcgataa      3300
accagcatgc ctgctcgtgt cgtgtgagga gtataaattt ttttaaacgt atattcatct     3360
ttaaactctg aaattcagaa tattattgag ccctaatttt cagtgttttc atttgagttt     3420
ttaaccagta aaaatagttt ttcagttta aaaattgctc cgagagctag ttttaaata      3480 ttctaatttc aggttgtgat agacggtgag acatgcctcc tcgacatatt ggataccgcc     3540
ggacaagaag aatattcggc gatgcgtgat cagtacatga ggacaggcga aggatttctg      3600
ttggttttcg ccgtcaacga ggctaaatct ttcgagaatg tcgctaacta ccgcgagcag      3660
attcggaggg taaaggattc agatgatgtg agtttttttt gttgaaatta tcagtcaatg     3720
gttgaatatt tgtatttctt ctaggttcct atggtcttgg tagggaataa atgtgatttg      3780
tcatctcgat cagtcgactt ccgaacagtc agtgagacag caaagggtta cggtattccg      3840
aatgtcgaca catctgccaa aacgcgtatg ggagttgatg aagcatttta cacacttgtt     3900
agagaaattc gcaaggtaat ttttagtta aaaatttaaa ttaaaaataa tgttttaat     3960 gtacaattaa ggtacaaatt cagtcattat tatatgaaaa ttgaaagacg cgagattttg    4020
atattttcgc gccaaaaata cgacacccgg tctgttcgat ttgctccttc aaatattatg     4080
gtaactttat actgtcgtta cagcggaatt ttcatcaatt tttttaagtt ttcgatatta     4140
taaaaatatt taaaaacaca gcagttttaa taaatcggtg aaaattaccc cagaaacgaa     4200
atattaaagt tactgtattc tttaaaggcg cacatacgtt tgcattaac acaaattcat      4260 cgtgtcgaga ccgggcaccg catctttaat ttgaaaatcg ccaaatgttg catttgagta    4320
atacaaaaac gttgttttta aaaatttct gttttgtaaa gctctaaaat gttattattg     4380
```

-continued

| | | | | |
|---|---|---|---|---|
| ttatcaacag | tttcaagttt | ccatttttca | ctaaaaacga | aaaatgtaag | ttttttccgat | 4440 |
| atttcgaaac | aaaagctcaa | agttttggtc | attttcttaa | tttttaaaga | aaattatatg | 4500 |
| ttttctttttg | ttttttttct | caccagcatg | cacaaaatct | gataaaaaat | tgagttttat | 4560 |
| tgttaatttt | ctaaaaaaaa | ttttgatgac | accctagatt | gatatccgaa | agatttaata | 4620 |
| atgttttctt | tttatttcag | catcgtgagc | gtcacgacaa | taataagcca | caaagaaga | 4680 |
| agaagtgtca | aataatgtga | ttcagcgtcg | ggaattgccc | aatttcgcca | actcattttc | 4740 |
| agtcgtgtca | actcccaccc | aattatcctt | tctcgtactt | ttttggtaca | ttttcattat | 4800 |
| tcatttatct | gttttatctg | aaacttgtga | tcgatcctct | tccgcctcta | catactcttc | 4860 |
| gaatttccac | ctttttttct | ctatgcatcg | attgaacttg | ttctctcgtc | tgctcgtcat | 4920 |
| tatttttct | cctttttttt | cttcatcctt | cattctaatt | cctcatcttt | cgcttagccc | 4980 |
| aaatctccat | tcattcatag | gtgtcaaaac | tagctgtagt | gtgtgatcca | tatctaaaac | 5040 |
| atgcatccga | accccctcct | cgttccaaaa | ttggccaact | ctaccaaaaa | aaacatcgca | 5100 |
| ccatttttt | ttcactttct | ctgcatattt | tcagaatgtt | tgtattgctt | ttttgatgct | 5160 |
| ttattcccct | tcctcgtttt | catacaaatt | attggcctca | tctattttca | gaagttctct | 5220 |
| gaaaattaaa | ttcttttgca | tctgccggtc | gttccgttta | ttttttctct | gtttcctctc | 5280 |
| atttttgtca | agtaattatt | tctctttcat | taactataat | atagatacaa | ttagaccca | 5340 |
| tttctcatac | attttctgaa | catctgaaag | ttttgctcc | ctcgtattgc | attcattttt | 5400 |
| ctctattcct | ctacatttta | tagtcctatc | tgaatataat | attcctattc | ttttgatcaa | 5460 |
| gtttttatta | ttattttatt | ttcaaggaag | tattgcaatg | atataaattt | taaaagcta | 5520 |
| atattatttt | tttaaatcta | ttcaactata | ttttgttaat | ttcagtgtta | tattttgacc | 5580 |
| tcgccatcgg | agcatgattt | taaaaaaaac | taaatttaat | ttattagaat | gacgagaaaa | 5640 |
| aggaaaaatg | tagagtctga | tgagaatcct | ccagcgaaaa | actcatttga | aggatacgga | 5700 |
| tatgctgctg | ctgatgctga | gaagaagcca | caggaggaga | gaaacaattt | cagaactttt | 5760 |
| ctagccaaaa | atgaacgatt | tggaagtgga | aatcgaggtg | gaggaggtcg | tggaagagga | 5820 |
| ggagatggtg | gatttagaag | aaatgataga | ggtggacgtg | gtggtggtgg | aagaggattc | 5880 |
| ggtggtaaca | gagaattcag | tgccggagat | tttgagaagg | tttgtgtcag | atggtgtcgt | 5940 |
| gagtgatgta | gcgtctctgg | cttttttaaac | tcaaaattac | agaaaaagtt | tcgatatgtc | 6000 |
| gagttaaaaa | catttctaaa | atttgtatta | ttttgcaaaa | aataaaaaaa | agccgaatta | 6060 |
| ttttttgaatt | ttttagtcat | tttcctggac | aaaaaattgtt | caaaatgtgg | aattataggt | 6120 |
| tttagaccaa | tttcattttta | tcgaatttcg | ttcggatttt | cgaggtttct | ttccgaaaaa | 6180 |
| ctgtctgaaa | aaatgagcgc | gggaattcac | aaatatttca | gtattttttt | gaaattgaat | 6240 |
| tttaaaaaat | ttatattcga | tatattgaga | cttttttctg | tgaagaatcg | ataaaatgaa | 6300 |
| ctccaaagcg | ctccctaggc | aattaccaca | aaaacgtata | tatttattta | atttacagca | 6360 |
| atacggtcga | gttggcggcg | gtgatgcacg | gaattcagga | caaccggata | gctacgaca | 6420 |
| agctgattcg | gcttcattca | acgactctcg | accagatgga | gatggtcgtg | aatttccgaa | 6480 |
| agaaattgtt | ggttatctga | gaagtattga | acaaatcaag | aagaaagagg | gaaaaattga | 6540 |
| agattttatt | ctggaaaagt | gtgctgaaga | agttgttggc | caggagaaaa | ctcttctctc | 6600 |
| gtggacagaa | gcagccgttg | ttgttgaatc | tgtatttgga | agttgtccta | aaggagcagc | 6660 |
| tctcttcctt | tcatcgattt | ctcgtctcaa | gcataaaaca | ttagctgagc | tgattttcgg | 6720 |
| aggagctagt | gctaggacaa | ttgaaaattt | gatattctcg | atgtgcccaa | tcgccgaatc | 6780 |

```
agaacatgtg gagattcttc aaaaactagc aggaattctt atggataact gggcggatgc      6840
tgttacaaca caaccttcga gttttctgat tcgagctatt gtctgggtgt gttgtggatt      6900
gtcagcaagg ccaaaggttg gagaggaaaa gaaaagaaat tacaaaggac aagaaatgaa      6960
ggctagcttg aagaatgttt atgaaaaact tgcaatcttg gcattcgatg agaatcttaa      7020
taaaaccttt atggattctc cgattttgt gacactattt caagatttta ttgaagccga      7080
tgggctttgg ggagacaaaa gaggtgatga atatgtgaag aagaagctcg aaaaggaaga      7140
tattgaagga atctcgaagg catggtattc atcaaatgga tct                       7183
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 11

```
ttccaagagt ctctcatcgg                                                   20
```

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 12

```
atgaaatctc ataatgccca c                                                 21
```

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic

<400> SEQUENCE: 13

```
ctgtgataaa gtattcaatt tcac                                              24
```

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 14

```
gcatttcaaa tttttcagag c                                                 21
```

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic

<400> SEQUENCE: 15

```
tcatttgaag caaaatcccc c                                                 21
```

<210> SEQ ID NO 16
<211> LENGTH: 20
<212> TYPE: DNA

```
<213> ORGANISM: Artificial Sequence
<220> FEATURE:
<223> OTHER INFORMATION: Description of Artificial Sequence:  Synthetic

<400> SEQUENCE: 16
aactcaccaa tttcctcggg                                           20

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:  Synthetic

<400> SEQUENCE: 17
ggatcttgga catcaatcac c                                         21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:  Synthetic

<400> SEQUENCE: 18
gaaaacaagt tttgcaaccc g                                         21
```

What is claimed is:

1. An isolated nucleotide sequence encoding a suppressor-of-ras-8 (SUR-8) protein.

2. The isolated nucleotide sequence of claim 1, wherein said suppressor-of-ras-8 (SUR-8) protein comprises a protein selected from the group consisting of human, murine and *Caenorhabditis elegans* suppressor-of-ras-8 (SUR-8) proteins.

3. The isolated nucleotide sequence of claim 1, wherein said isolated nucleotide sequence is selected from the group consisting of SEQ ID NO: 1 SEQ ID NO: 5 and SEQ ID NO: 6.

4. A vector comprising said nucleotide sequence of claim 1.

5. A host cell transformed with said vector of claim 4.

6. The host cell of claim 5, wherein said cell is selected from the group consisting of bacteria, yeast, amphibian, and mammalian cells.

7. An isolated polynucleotide sequence selected from the group consisting of SEQ ID NO: 11, SEQ ID NO: 12, SEQ ID NO: 13, SEQ ID NO: 15, and SEQ ID NO: 18.

8. A method for detecting a polynucleotide encoding a suppressor-of-ras-8 (SUR-8) protein, comprising:
   a) providing:
      i) a biological sample suspected of containing a polynucleotide sequence encoding a suppressor-of-ras-8 (SUR-8) protein, and
      ii) a nucleotide sequence, wherein said nucleotide sequence is selected from the group consisting of SEQ ID NO: 11, SEQ ID NO: 12, SEQ ID NO: 13, SEQ ID NO: 14, SEQ ID NO: 15, SEQ ID NO: 16, SEQ ID NO: 17 and SEQ ID NO: 18; and
   b) hybridizing said nucleotide sequence to said polynucleotide sequence encoding said suppressor-of-ras-8 (SUR-8) protein under stringent conditions, wherein said conditions comprise 65° C., overnight incubation in 5×saline-sodium-phosphate-EDTA (SSPE) buffer, 5×Denhardt's solution and 0.5% sodium dodecyl sulfate (SDS).

9. The method of claim 8, further comprising the step of detecting said hybridization complex, wherein the presence of said hybridization complex correlates with the presence of said polynucleotide sequence in said biological sample.

10. The method of claim 8, wherein said polynucleotide sequence is amplified before said hybridizing step.

11. An isolated poly nucleotide sequence with 100% antiparallel complementarity to the nucleotide sequence of claim 1.

12. An isolated polynucleotide sequence with 100% antiparallel complementarity to the nucleotide sequence selected from the group consisting of SEQ ID NO: 11, SEQ ID NO: 12, SEQ ID NO: 13, SEQ ID NO: 15, and SEQ ID NO: 18.

* * * * *